(12) United States Patent
Schinazi et al.

(10) Patent No.: US 12,239,655 B2
(45) Date of Patent: Mar. 4, 2025

(54) COMBINED MODALITIES FOR NUCLEOSIDES AND/OR NADPH OXIDASE (NOX) INHIBITORS AS MYELOID-SPECIFIC ANTIVIRAL AGENTS

(71) Applicants: Raymond F. Schinazi, Atlanta, GA (US); Franck Amblard, Atlanta, GA (US); Christina Gavegnano, Atlanta, GA (US); Bryan Cox, Atlanta, GA (US); Seema Mengshetti, Atlanta, GA (US)

(72) Inventors: Raymond F. Schinazi, Atlanta, GA (US); Franck Amblard, Atlanta, GA (US); Christina Gavegnano, Atlanta, GA (US); Bryan Cox, Atlanta, GA (US); Seema Mengshetti, Atlanta, GA (US)

(73) Assignee: Emory University, Atlanta, GA (US)

( * ) Notice: Subject to any disclaimer, the term of this patent is extended or adjusted under 35 U.S.C. 154(b) by 255 days.

(21) Appl. No.: 16/958,572

(22) PCT Filed: Dec. 27, 2018

(86) PCT No.: PCT/US2018/067674
§ 371 (c)(1),
(2) Date: Jun. 26, 2020

(87) PCT Pub. No.: WO2019/133712
PCT Pub. Date: Jul. 4, 2019

(65) Prior Publication Data
US 2021/0060051 A1 Mar. 4, 2021

Related U.S. Application Data

(60) Provisional application No. 62/610,841, filed on Dec. 27, 2017.

(51) Int. Cl.
| | | |
|---|---|---|
| *A61K 31/7076* | (2006.01) | |
| *A61K 31/12* | (2006.01) | |
| *A61K 31/17* | (2006.01) | |
| *A61K 31/41* | (2006.01) | |
| *A61K 31/428* | (2006.01) | |
| *A61K 31/437* | (2006.01) | |
| *A61K 31/45* | (2006.01) | |
| *A61K 31/519* | (2006.01) | |
| *A61K 31/5415* | (2006.01) | |
| *A61K 31/69* | (2006.01) | |
| *A61K 31/7072* | (2006.01) | |
| *A61K 45/06* | (2006.01) | |
| *A61P 31/14* | (2006.01) | |
| *A61P 31/16* | (2006.01) | |
| *A61P 31/18* | (2006.01) | |
| *A61P 31/22* | (2006.01) | |

(Continued)

(52) U.S. Cl.
CPC .......... *A61K 31/7076* (2013.01); *A61K 31/12* (2013.01); *A61K 31/17* (2013.01); *A61K 31/41* (2013.01); *A61K 31/428* (2013.01); *A61K 31/437* (2013.01); *A61K 31/45* (2013.01); *A61K 31/519* (2013.01); *A61K 31/5415* (2013.01); *A61K 31/69* (2013.01); *A61K 31/7072* (2013.01); *A61K 45/06* (2013.01); *A61P 31/14* (2018.01); *A61P 31/16* (2018.01); *A61P 31/18* (2018.01); *A61P 31/22* (2018.01); *C07C 275/40* (2013.01); *C07D 275/04* (2013.01); *C07D 279/20* (2013.01); *C07D 417/04* (2013.01); *C07D 471/04* (2013.01); *C07H 19/10* (2013.01); *C07H 19/16* (2013.01)

(58) Field of Classification Search
CPC ........ A61K 31/70; A61K 31/16; A61K 31/12; A61K 31/17; A61K 31/41; A61K 31/428; A61K 31/417; A61K 31/45; A61K 31/519; A61K 31/5415; A61K 31/69; A61K 31/7072; A61P 31/22; A61P 31/14; A61P 31/18; C07C 275/40; C07D 275/04; C07D 279/20; C07D 417/04; C07D 471/04; C07H 19/10; C07H 19/16
See application file for complete search history.

(56) References Cited

U.S. PATENT DOCUMENTS

| | | | | |
|---|---|---|---|---|
| 6,423,327 B1 * | 7/2002 | Dobson, Jr. | ............. | A61P 43/00 |
| | | | | 424/447 |
| 9,981,968 B2 * | 5/2018 | Schiltz | ................... | A61P 35/00 |

(Continued)

FOREIGN PATENT DOCUMENTS

| | | |
|---|---|---|
| WO | 0069786 A1 | 11/2000 |
| WO | 2007020193 A2 | 2/2007 |

(Continued)

OTHER PUBLICATIONS

Nomura, Journal of Medicinal Chemistry, 1999, vol. 42, No. 15. (Year: 1999).*

(Continued)

*Primary Examiner* — Layla D Berry
(74) *Attorney, Agent, or Firm* — David S. Bradin; Maynard Nexsen PC

(57) ABSTRACT

Nucleoside compounds, which in some embodiments include an alkynyl substituent at the 4'-position, compositions and methods for treating or preventing HIV and other viral infections, particularly where the virus is present in macrophages, microglia, and primary myeloid cells, and eliminating and/or treating infection in patients infected by these viruses, are disclosed.

22 Claims, No Drawings
Specification includes a Sequence Listing.

(51) Int. Cl.
  *C07C 275/40* (2006.01)
  *C07D 275/04* (2006.01)
  *C07D 279/20* (2006.01)
  *C07D 417/04* (2006.01)
  *C07D 471/04* (2006.01)
  *C07H 19/10* (2006.01)
  *C07H 19/16* (2006.01)

(56) References Cited

U.S. PATENT DOCUMENTS

| | | | |
|---|---|---|---|
| 2002/0022722 A1* | 2/2002 | Ohrui | A61P 31/18 536/28.1 |
| 2013/0034521 A1* | 2/2013 | Butler | A61P 31/12 514/23 |
| 2016/0002252 A1 | 1/2016 | Schiltz et al. | |
| 2016/0220595 A1* | 8/2016 | Liotta | A61P 31/20 |

FOREIGN PATENT DOCUMENTS

| | | |
|---|---|---|
| WO | 2010015637 A1 | 2/2010 |
| WO | 2015038596 A1 | 3/2015 |

OTHER PUBLICATIONS

Shi, Bioorganic & Medicinal Chemistry Letters 21 (2011) 7094-7098. (Year: 2011).*
Wagner, Current HIV Research, 2011, 9, 209-222. (Year: 2011).*
Thenin-Houssier, Antimicrobial Agents and Chemotherapy Apr. 2016, vol. 60, No. 4, pp. 2195-2208. (Year: 2016).*
International Search Report and Written Opinion issued in counterpart PCT Application No. PCT/US2018/067674 dated Jun. 10, 2019 (eleven (11) pages).
Extended European Search Report issued in counterpart EP Application No. 18894881.4 dated Apr. 8, 2022 (sixteen (16) pages).
Kodama E-I et al. 2001. "4'-Ethynyl Nucleoside Analogs: Potent Inhibitors of Multidrug-Resistant Human Immunodeficiency Virus Variants In Vitro." Antimicrobial Agents and Chemotherapy, vol. 45, Issue 5, May 1, 2001, pp. 1539-1546.

* cited by examiner

COMBINED MODALITIES FOR NUCLEOSIDES AND/OR NADPH OXIDASE (NOX) INHIBITORS AS MYELOID-SPECIFIC ANTIVIRAL AGENTS

ACKNOWLEDGMENT OF GOVERNMENT RIGHTS

Certain embodiments of the invention described herein were made with government support through NIH Grant Number 1RO1MH100999. The U.S. Government has certain rights in the invention.

FIELD OF THE INVENTION

The present invention is directed to compounds, methods and compositions for treating or preventing HIV. More specifically, the invention describes certain nucleoside and nucleotide analogs along with NADPH Oxidase (NOX) inhibitors, pharmaceutically acceptable salts, or other derivatives thereof, and the use thereof in the treatment of HIV, especially in myeloid cells including macrophages.

BACKGROUND OF THE INVENTION

Macrophages are non-dividing cells that are unique from lymphocytes due to multiple factors including: 1) non-dividing phenotype, 2) low dNTP levels, 3) similar ratios of dNTP/rNTP, 3) unique receptor expression profile, 4) antigen presenting and phagocytic capacity as part of the innate immune response.

Macrophages are a systemic viral reservoir for HIV, and unlike lymphocytes, demonstrate suboptimal accumulation of antiviral agents at intracellular concentrations which efficiently eliminate ongoing HIV infection (see, for example, Gavegnano et al., "Cellular pharmacology and potency of HIV-1 nucleoside analogs in primary human macrophages, Antimicrob Agents Chemother., 57(3):1262-9 (2013); Gavegnano et al., "The Impact of Macrophage Nucleotide Pools on HIV-1 Reverse Transcription, Viral Replication, and the Development of Novel Antiviral Agents, Mol Biol Int. 2012:625983 (2012); Kennedy et al., "Ribonucleoside triphosphates as substrate of human immunodeficiency virus type 1 reverse transcriptase in human macrophages," J. Biol. Chem. 10; 285(50):39380-91 (2010); and Gavegnano and Schinazi, "Antiretroviral therapy in macrophages: implication for HIV eradication," Antivir. Chem. Chemother. 20(2):63-78 (2009)).

NADPH Oxidases (NOX) are a family of enzymes that generate reactive oxygen species that are highly expressed in macrophages, but low or absent in all other cell types (see, for example, Salmen and Berrueta, "Immune Modulators of HIV Infection: The Role of Reactive Oxygen Species." J. Clin. Cell. Immunol. 3:2 (2012) and Zhang et al., "Akt/Nox2/NF-jB signaling pathway is involved in Tat-induced HIV-1 long terminal repeat (LTR) transactivation," Archives of Biochemistry and Biophysics, 505 266-272 (2011)).

NOX are multi-subunit enzymes composed of membrane-bound cytochrome b558 and three cytosolic protein subunits, p47phox, p67phox, and the GTPase Rac. There are seven isoforms of NOX enzymes including NOXI, NOX2, NOX3, NOX4, NOX5, DUOXI and DUOX2. Several viral proteins have been shown to interact with components of the NOX system. For HIV-1, A specific physical association between HIV-1 Nef (amino acids 105-109) and the p22-phox component (amino acids 126-129) of the NADPH oxidase complex is demonstrated by biochemistry and computer analysis. HIV-1 Tat increases phosphorylation of the NADPH oxidase subunit p47(phox) and causes its rapid redistribution to membrane ruffles in human endothelial cells. HIV-1 gp120 binding to CXCR4 induces NADPH oxidase-mediated production of superoxide radicals in neurons, which is involved in the activation of neutral sphingomyelinase. The 3S motif of HIV-1 gp41 stimulates ROS production by NADPH oxidase. HIV-1 Tat-induced glutamate release is mediated through p38 and p42/44 MAPK and through NADPH oxidase and the x(c)(−) cystine-glutamate antiporter (xCT). Blockade of NOX signaling in macrophages results in down-regulation of HIV or virally induced inflammatory events that promote infection either directly or indirectly. Blockade of NOX signaling also inhibits virally induced inflammatory events that contribute to non-AIDS related morbidity and mortality, and HIV-associated dementias and neurocognitive impairments originating from macrophages/myeloid cells.

It would be advantageous to provide new antiviral compositions, and methods of treatment, particularly to treat HIV residing in the macrophages. The present invention provides such agents, compositions and methods.

SUMMARY OF THE INVENTION

The present invention relates to compounds, methods and compositions for treating or preventing HIV and/or other viral infections in a host. The methods involve administering a therapeutically or prophylactically-effective amount of at least one compound described herein to treat or prevent an infection by, or an amount sufficient to reduce the biological activity of, HIV-1 or other viral infections which target macrophages, including, but not limited to, Chikungunya, Mayaro, Yellow Fever, Zika, Dengue, HIV-2, HTLV-1 and Japanese Encephalitis viruses.

In one embodiment, the invention relates to methods of using potent, selective antiviral agents to target HIV and other viral infections in macrophages, microglia, and primary myeloid cells, and thus help eliminate and/or treat infection in patients infected by these viruses.

In one aspect of this embodiment, the compounds used include one or more of the specific nucleoside inhibitors described herein. In another aspect of this embodiment, the compounds used are NOX inhibitors. In a third aspect of this embodiment, the compounds used include both the specific nucleoside inhibitors described herein, and NOX inhibitors. Both types of compounds exploit unique myeloid/macrophage-specific characteristics as described herein to confer potent, selective inhibition of HIV and other viral infections in macrophages/myeloid cells. In another embodiment, the invention relates to pharmaceutical compositions including one or more of the compounds described herein, in combination with a pharmaceutically acceptable carrier or excipient. These compositions can be used to treat a host infected with HIV or other viral infections, to prevent one of these infections, and/or to reduce the biological activity of one of these viruses. In one aspect of this embodiment, the treatment, prevention, and/or reduction of the biological activity occurs, at least in part, within the macrophages. The compositions can include a combination of one or more of the compounds described herein, with other antiviral compounds or biological agents, including anti-HIV compounds and biological agents, such as Nucleoside Reverse Transcriptase Inhibitors (NRTIs), Non-nucleoside Reverse Transcriptase Inhibitors (NNRTIs), Fusion Inhibitors, Entry Inhibitors, CCR5 co-receptor antagonist and HIV integrase strand transfer inhibitors, anti-inflammatories including Jak inhibitors, including, but not limited to tofacitinib, baricitinib, ruxolitinib, upadacitinib other immunomodulators, dasatinib, MAPK inhibitors, mTOR inhibitors, β-catenin inhibitors, interferon inhibitors, interferon, HDAC inhibitors, PKC agonists, TLR4 agonists, or other reactivation agents for HIV infection and latency.

In yet another embodiment, the present invention relates to processes for preparing the specific nucleoside compounds described herein.

In some embodiments, the compounds described herein are deuterated at one or more positions. Where the compounds are nucleosides, deuteration can be present in one or more positions on the sugar moiety of the compounds, the base portion of the compounds, and/or the prodrug portion of the compounds, at any position other than the 2'-position.

The present invention will be better understood with reference to the following Detailed Description.

DETAILED DESCRIPTION

The compounds described herein show inhibitory activity against HIV in cell-based assays. Therefore, the compounds can be used to treat or prevent a HIV in a host, or reduce the biological activity of the virus. The host can be a mammal, and in particular, a human, infected with HIV or other viral infections that target macrophages including but not limited to Chikungunya, Mayaro, Yellow Fever, Zika, or Japanese Encephalitis viruses. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, $SF_5$, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "fatty alcohol" as used herein refers to straight-chain primary alcohols with between 4 and 26 carbons in the chain, preferably between 8 and 26 carbons in the chain, and most preferably, between 10 and 22 carbons in the chain. The precise chain length varies with the source. Representative fatty alcohols include lauryl, stearyl, and oleyl alcohols. They are colourless oily liquids (for smaller carbon numbers) or waxy solids, although impure samples may appear yellow. Fatty alcohols usually have an even number of carbon atoms and a single alcohol group (—OH) attached to the terminal carbon. Some are unsaturated and some are branched. They are widely used in industry. As with fatty acids, they are often referred to generically by the number of carbon atoms in the molecule, such as "a C12 alcohol", that is an alcohol having 12 carbons, for example dodecanol.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human being. Veterinary applications, in certain indications, however, are clearly contemplated by the present invention (such as for use in treating chimpanzees).

The term nucleoside also includes ribonucleosides, and representative ribonucleosides are disclosed, for example, in the Journal of Medicinal Chemistry, 43(23), 4516-4525 (2000), Antimicrobial Agents and Chemotherapy, 45(5), 1539-1546 (2001), and PCT WO 2000069876.

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically-acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compounds

The nucleoside compounds described herein are of one of the following formulas:

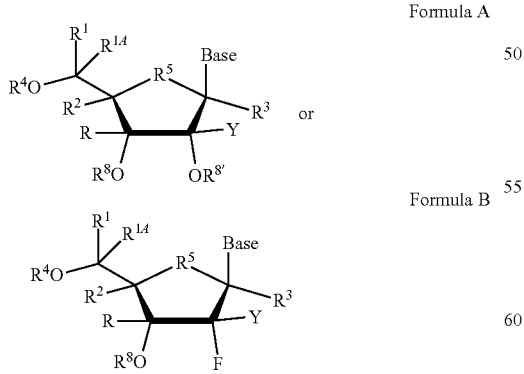

or a pharmaceutically acceptable salt or prodrug thereof, wherein:

Y is H, $C_{1-6}$ alkyl, $C_{1-6}$ haloalkyl, $C_{2-6}$ alkenyl, $C_{2-6}$ alkynyl, R is selected from the group consisting of H, substituted or unsubstituted $C_{1-6}$ alkyl, $C_{1-6}$ haloalkyl, $C_{1-6}$ alkoxy, substituted or unsubstituted $C_{2-6}$ alkenyl, substituted or unsubstituted $C_{2-6}$ alkynyl, substituted or unsubstituted $C_{3-6}$ cycloalkyl, aryl, heteroaryl, heterocyclic, alkylaryl, arylalkyl, hydroxyl, nitro, cyano, cyanoalkyl, azido, azidoalkyl, formyl, hydrazino, OR', SR', COOR', COR', OCOR', NHCOR', N(COR')COR', SCOR', OCOOR', and NHCOOR', wherein each R' is independently H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, wherein the groups can be substituted with one or more substituents selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, $R^1$ is and $R^{1A}$ are, independently, H, $CH_3$, $CH_2F$, $CHF_2$, or $CF_3$, wherein, when $R^1$ is Me, the carbon to which it is attached may be wholly or partially R or S or any mixture thereof, or R and R can combine to form a $C_{3-7}$ cycloalkyl ring;

$R^2$ is H, CN, $N_3$, F, substituted or unsubstituted $C_{1-8}$ alkyl, substituted or unsubstituted $C_{2-8}$ alkenyl or substituted or unsubstituted $C_{2-8}$ alkynyl;

$R^4$ is H, $P(O)R^6R^7$, or a mono-, di-, or triphosphate, wherein, when chirality exists at the phosphorous center of $R^4$, it may be wholly or partially $R_p$ or $S_p$ or any mixture thereof, $R^5$ is O, $CH_2$, S, Se, CHF, $CF_2$, or $C=CH_2$, $R^3$ is H, substituted or unsubstituted $C_{1-8}$ alkyl, substituted or unsubstituted $C_{2-8}$ alkenyl, substituted or unsubstituted $C_{2-8}$ alkynyl, CN or $N_3$ when $R^5$ is O, and $R^3$ is selected from the group consisting of H, CN, substituted or unsubstituted $(C_{1-8})$alkyl, substituted or unsubstituted $(C_{2-8})$alkenyl, substituted or unsubstituted $(C_{2-8})$alkynyl, O—$(C_{1-8})$ alkyl and $N_3$ when $R^5$ is $CH_2$, CHF, $CF_2$, or $C=CH_2$, $R^8$ and $R^{8'}$ are independently selected from the group consisting of H, $C(O)(C_{1-8})$alkyl, $C(O)(C_{1-8})$ branched alkyl, $C(O)NH(C_{1-8})$alkyl, $C(O)NH(C_{1-8})$ branched alkyl, $C(O)$aryl $C(O)(C_{1-8})$alkyl-aryl, $C(O)NH(C_{1-8})$alkyl-aryl $C(O)O(C_{1-8})$alkyl, $C(O)O(C_1$-8) branched alkyl, and $C(O)O(C_{1-8})$alkyl-aryl, or $OR^{8'}$ as it appears in Formulas A is an ester derived from an alpha amino acid, $R^6$ and $R^7$ are independently selected from the group consisting of:

(a) $OR^{15}$ where $R^{15}$ selected from the group consisting of H,

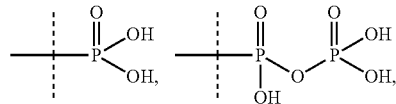

Li, Na, K, substituted or unsubstituted $C_{1-20}$alkyl, substituted or unsubstituted $C_{3-6}$cycloalkyl, $C_{1-4}$(alkyl)aryl, benzyl, $C_{1-6}$ haloalkyl, $C_{2-3}$(alkyl)O$C_{1-20}$alkyl,

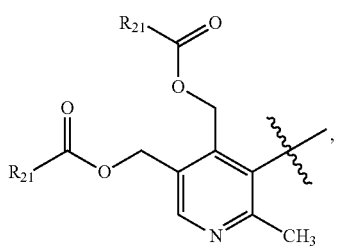

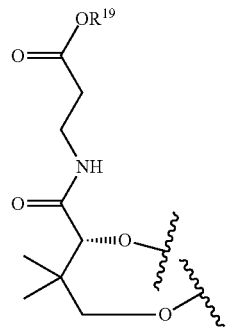

(d) $R^6$ and $R^7$ can come together to form a ring where $R^{19}$ is H, $C_{1-20}$ alkyl, $C_{1-20}$ alkenyl, the carbon chain derived from a fatty alcohol or $C_{1-20}$ alkyl optionally substituted with a $C_{1-6}$alkyl, alkoxy, di($C_{1-6}$alkyl)-amino, fluoro, $C_{3-10}$ cycloalkyl, cycloalkyl-$C_{1-6}$alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$alkyl, alkoxy, di($C_{1-6}$alkyl)-amino, fluoro, or $C_{3-10}$ cycloalkyl;

(e) $R^6$ and $R^7$ can come together to form a ring selected from the group consisting of

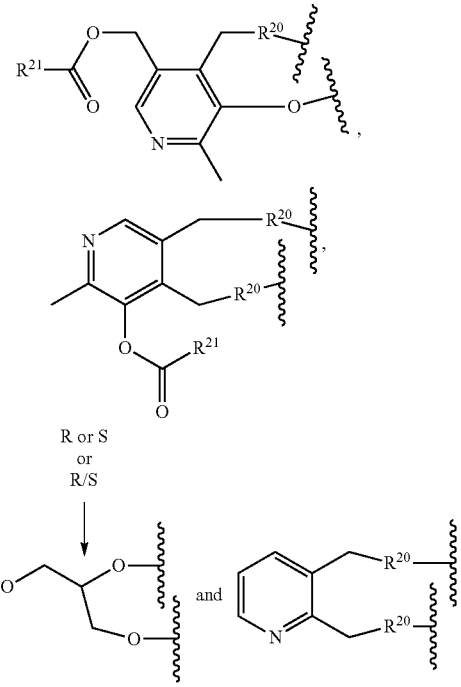

aryl, and heteroaryl, such as phenyl and pyridinyl, wherein aryl and heteroaryl are optionally substituted with zero to three substituents independently selected from the group consisting of $(CH_2)_{0-6}CO_2R^{16}$ and $(CH_2)_{0-6}CON(R^{16})_2$;

where $R^{16}$ is independently H, substituted or unsubstituted $C_{1-20}$ alkyl, the carbon chain derived from a fatty alcohol or $C_{1-20}$ alkyl substituted with a $C_{1-6}$ alkyl, $C_{1-6}$ alkoxy, di($C_{1-6}$ alkyl)-amino, fluoro, $C_{3-10}$ cycloalkyl, cycloalkyl-$C_{1-6}$ alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, alkoxy, di($C_{1-6}$ alkyl)-amino, fluoro, $C_{3-10}$ cycloalkyl, or cycloalkyl;

(b)

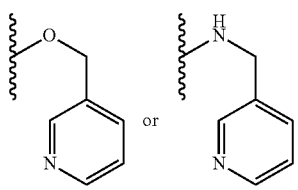 [SMILES: *OCc1cccnc1 ; *NCc1cccnc1]

(c) the ester of a D- or L-amino acid

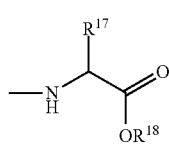

where $R^{17}$ is restricted to those occurring in natural L-amino acids, and $R^{18}$ is H, $C_{1-20}$ alkyl, the carbon chain derived from a fatty alcohol or $C_{1-20}$ alkyl optionally substituted with a $C_{1-6}$ alkyl, alkoxy, di($C_{1-6}$alkyl)-amino, fluoro, $C_{3-10}$ cycloalkyl, cycloalkyl-$C_{1-6}$ alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$alkyl, alkoxy, di($C_{1-6}$alkyl)-amino, fluoro, $C_{3-10}$ cycloalkyl, or cycloalkyl;

where
$R^{20}$ is O or NH, and
$R^{21}$ is selected from the group consisting of H, substituted or unsubstituted $C_{1-20}$ alkyl, substituted or unsubstituted $C_{1-20}$ alkenyl, the carbon chain derived from a fatty acid, and $C_{1-20}$ alkyl optionally substituted with a $C_{1-6}$alkyl, alkoxy, di($C_{1-6}$alkyl)-amino, fluoro, $C_{3-10}$ cycloalkyl, cycloalkyl-$C_{1-6}$ alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$alkyl, alkoxy, di($C_{1-6}$alkyl)-amino, fluoro, $C_{3-10}$ cycloalkyl, or cycloalkyl, Base is selected from the group consisting of:

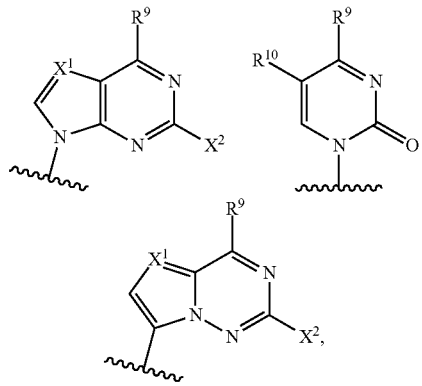

$X^1$ is CH, C—($C_{1-6}$)alkyl, C—($C_{2-6}$)alkenyl, C—($C_{2-6}$)alkynyl, C—($C_{3-7}$)cycloalkyl, C—($C_{1-6}$) haloalkyl, C—($C_{1-6}$)hydroxyalkyl, C—$OR^{22}$, C—N $(R^{22})_2$, C-halo, C—CN or N, $R^{22}$ is independently H, $(C_{1-10})$alkyl, $(C_{1-10})$haloalkyl or $(C_{3-7})$cycloalkyl, $R^9$ is OH, $NH_2$, halo (i.e., F, Cl, Br, or I), $O(C_{1-10})$alkyl, $O(C_{3-7})$cycloalkyl, $NH(C_{1-10})$alkyl, $N((C_{1-10})$alkyl$)_2$, $NH(C_{3-7})$cycloalkyl, $NH(CO)(C_{1-20})$alkyl, $NH(CO)O(C_{1-20})$alkyl, NHOH, $NHO(CO)(C_{1-20})$alkyl, $NHO(CO)NH(C_{1-20})$alkyl, $R^{10}$ is H, F or $CH_3$ and $X^2$ is H, F, Cl, Br, I, $(C_{1-6})$alkyl, $(C_{2-6})$alkenyl, $(C_{2-6})$alkynyl, C—$(C_{3-7})$cycloalkyl, C—$(C_{1-6})$ haloalkyl, $(C_{1-6})$haloalkyl, $(C_{3-7})$cycloalkyl, $(C_{1-6})$hydroxyalkyl, $OR^{22}$, $SR^{22}$, $N(R^{22})_2$, $NHC(O)OR^{22}$, $NHC(O)N(R^{22})_2$, $NHC(O)R^{22}$, CN or $NH_2$;

or Base is

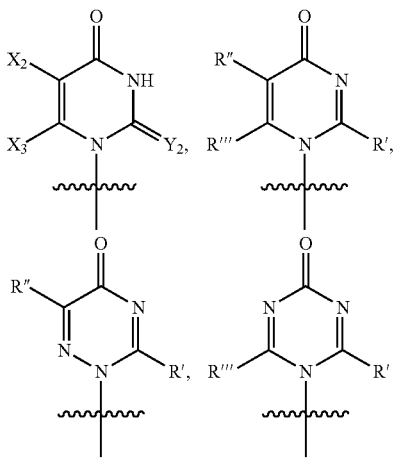

wherein:
each R', R'', and R''', are independently selected from the group consisting of H, OH, substituted or unsubstituted $C_{1-6}$ alkyl, substituted or unsubstituted $C_{2-6}$ alkenyl, substituted or unsubstituted $C_{2-6}$ alkynyl, $C_{3-6}$ cycloalkyl, Br-vinyl, —O—$C_{1-6}$ alkyl, O—$C_{2-6}$ alkenyl, O—$C_{2-6}$ alkynyl, O-aryl, O-aralkyl, —O-acyl, O—$C_{3-6}$ cycloalkyl, $NH_2$, $NHC_{1-6}$ alkyl, N-di-$C_{1-6}$-alkyl, NH-acyl, N-aryl, N-aralkyl, $NHC_{3-6}$ cycloalkyl, SH, S—$C_{1-6}$ alkyl, S-acyl, S-aryl, S—$C_{3-6}$ cycloalkyl, S-aralkyl, F, Cl, Br, I, CN, COOH, $CONH_2$, $CO_2C_{1-6}$ alkyl, $CONHC_{1-6}$ alkyl, CON-di-$C_{1-6}$ alkyl, OH, $CF_3$, $CH_2OH$, $(CH_2)_mOH$, $(CH_2)_mNH_2$, $(CH_2)_mCO_2H$, $(CH_2)_mCN$, $(CH_2)_mNO_2$, and $(CH_2)_mCONH_2$; m is 0 or 1;

$X_2$ is H, straight chained, branched or cyclic optionally substituted alkyl, $CH_3$, $CF_3$, $C(Y_3)_3$, 2-Br-ethyl, $CH_2F$, $CH_2Cl$, $CH_2CF_3$, $CF_2CF_3$, $C(Y_3)_2C(Y_3)_3$, $CH_2OH$, optionally substituted alkenyl, optionally substituted alkynyl, COOH, $COOR^{1B}$, COO-alkyl, COO-aryl, CO-Oalkoxyalkyl, $CONH_2$, $CONHR^{1B}$, $CON(R^{1B})_2$, chloro, bromo, fluoro, iodo, CN, $N_3$, OH, $OR^{1B}$, $NH_2$, $NHR^{1B}$, $NR^{1B}_2$, $SR^{1B}$ each $X_3$ is independently a straight chained, branched or cyclic optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y_3)^3$, 2-Br-ethyl, $CH_2F$, $CH_2Cl$, $CH_2CF_3$, $CF_2CF_3$, $C(Y_3)_2C(Y_3)_3$, optionally substituted $C_{2-6}$ alkenyl, $C_{2-6}$ haloalkenyl, Br-vinyl, optionally substituted alkynyl, $C_{2-6}$ haloalkynyl, $N_3$, CN, —C(O)OH, —C(O)$OR^{1B}$, —C(O)O($C_{1-6}$ alkyl), —C(O)$NH_2$, —C(O)$NHR^{1B}$, —C(O)NH($C_{1-6}$ alkyl), —C(O)N($R^{1B})_2$, —C(O)N ($C_{1-6}$ alkyl$)_2$, OH, $OR^{1B}$, —O(acyl), —O($C_{1-6}$ acyl), —O(alkyl), —O($C_{1-6}$ alkyl), —O($C_{2-6}$ alkenyl), —O($C_{2-6}$ alkynyl), —O(aralkyl), —O(cycloalkyl), S(acyl), —S($C_{1-6}$ acyl), —S($R^{1B}$), —S($C_{1-6}$ alkyl), —S(alkenyl), —S($C_{2-6}$ alkynyl), —S(aralkyl), —S($C_{3-6}$ cycloalkyl), chloro, bromo, fluoro, iodo, $NH_2$, —NH($C_{1-6}$ alkyl), —$NHR^{1B}$, —$NR^{1B}_2$, —NH (acyl), —N($C_{1-6}$ alkyl$)_2$, —NH(alkenyl), —NH (alkynyl), —NH(aralkyl), —NH(cycloalkyl), or —N(acyl$)_2$;

each $Y_2$ is independently O, S, Se, NH, or $NR^{1B}$;
each $Y_3$ is independently H, F, Cl, Br, or I; and
each $R^{1B}$ is independently hydrogen, acyl, alkyl, $C_{1-6}$ alkyl, $C_{2-6}$ alkenyl, $C_{2-6}$ alkynyl, or $C_{3-6}$ cycloalkyl;
wherein, in each occurrence, $C_{1-6}$ alkyl, $C_{2-6}$ alkenyl, or $C_{2-6}$ alkynyl, are optionally substituted with from 1-3 substituents selected from the group consisting of halogen (fluoro, chloro, bromo or iodo), hydroxyl, nitrile, amino, alkylamino, arylamino, alkoxy, thioalkoxy, aryloxy, nitro, cyano, sulfonic acid, sulfate, phosphonic acid, phosphate, or phosphonate,
deuterated analogs thereof,
and pharmaceutically-acceptable salts or prodrugs thereof.

In one embodiment, the compounds have the formula:

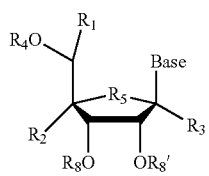

or pharmaceutically-acceptable salts or prodrugs thereof.

In some embodiments of these compounds, $R_2$ is $C_{2-8}$ alkynyl, such as $R_2$ is ethynyl. In one embodiment, $R_4$ is a phosphoramidate prodrug, a phosphonate prodrug, or a mono-, di- or triphosphate. In another embodiment, $R_{15}$ is phenyl or pyridinyl. In another embodiment, the compounds are deuterated at one or more positions on the base or the sugar. In another embodiment, one or more of $R_1$, $R_2$, $R_3$, $R_4$, R or Y, are H. In another embodiment, Y is H or Me. In another embodiment, and/or one or both of $R_8$ and $R_{8'}$ are H. Each combination of these embodiments is within the scope of the invention, as are pharmaceutically-acceptable salts and prodrugs of each of these combinations.

Specific nucleoside compounds have one of the following formulas:

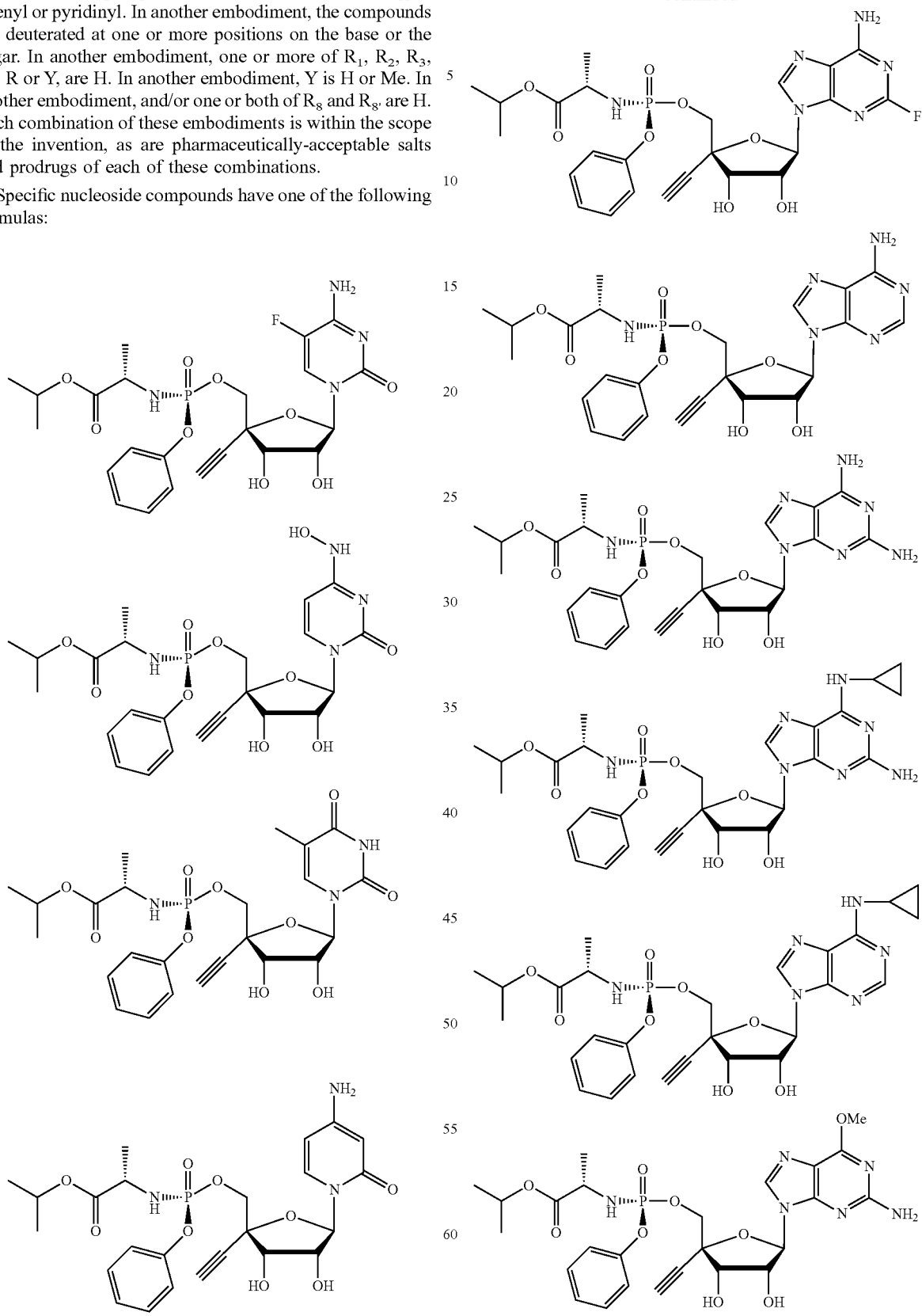

-continued
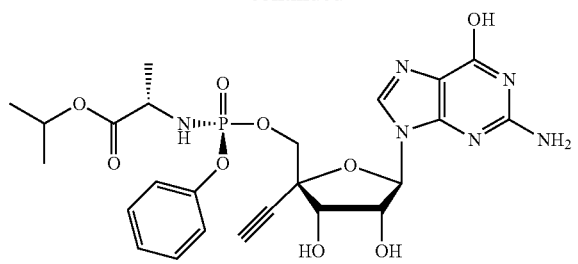
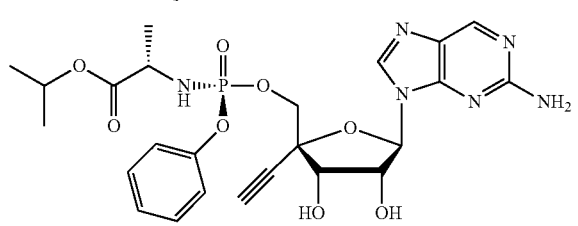
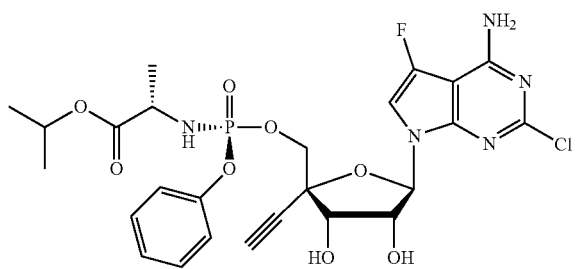
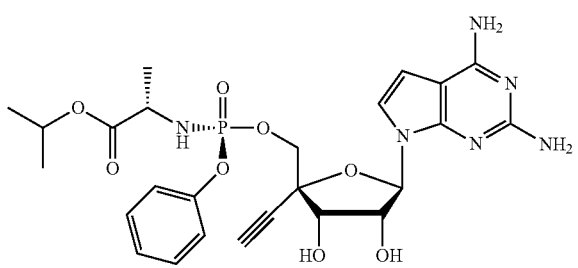
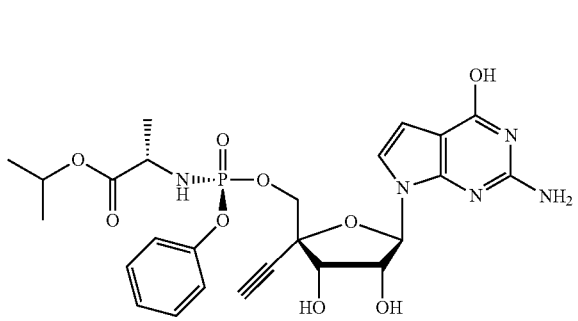
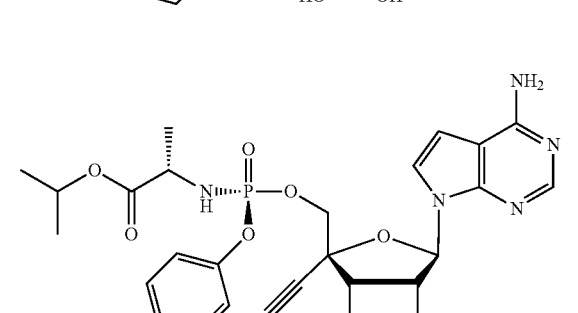
-continued
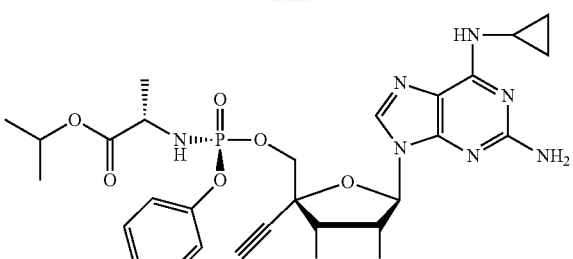
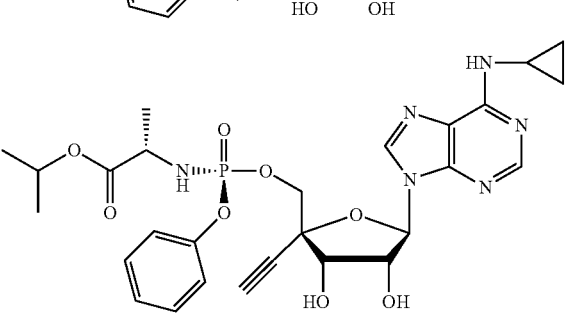
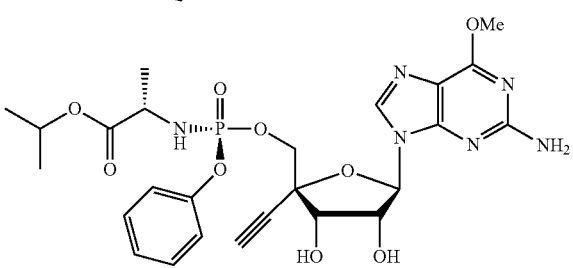
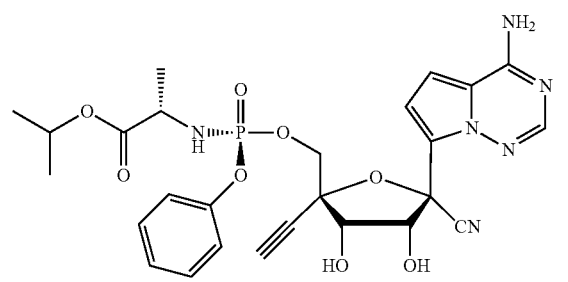
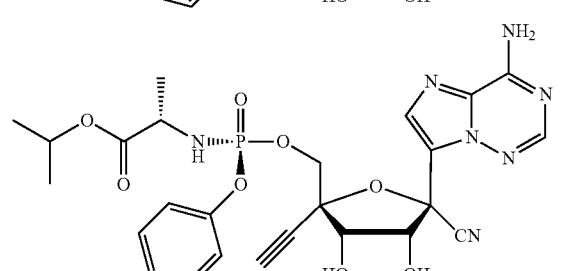
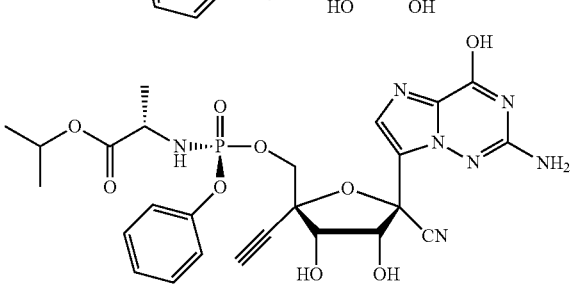

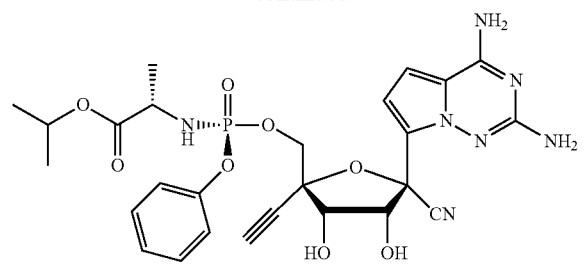
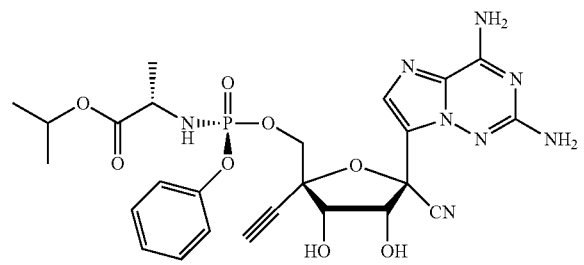
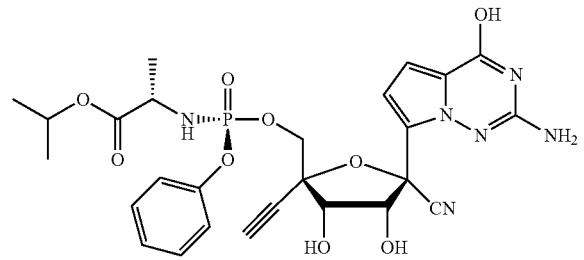
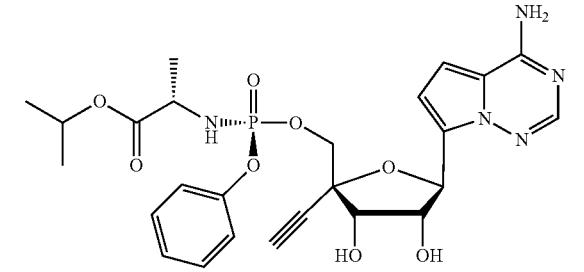
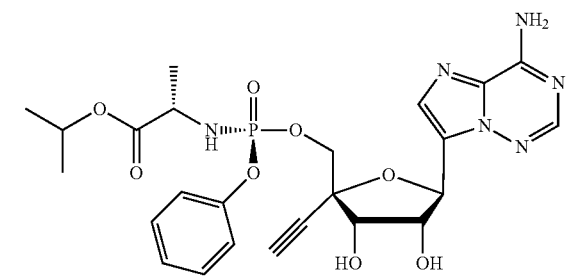
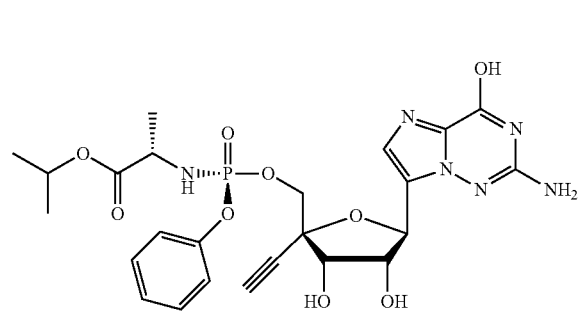
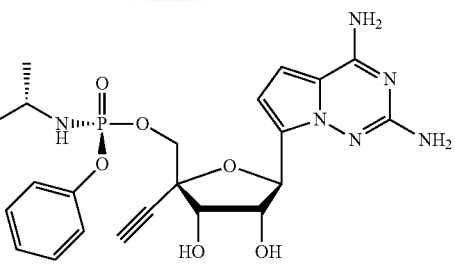
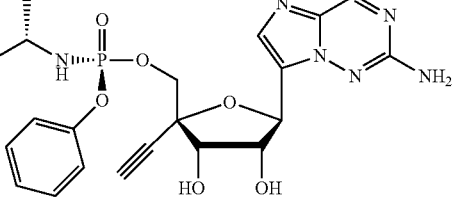
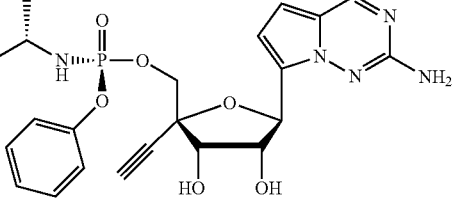
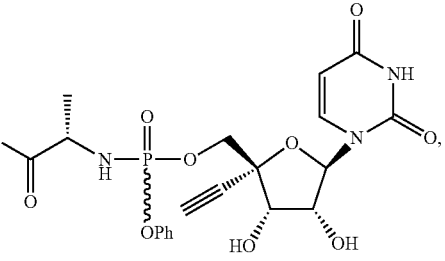
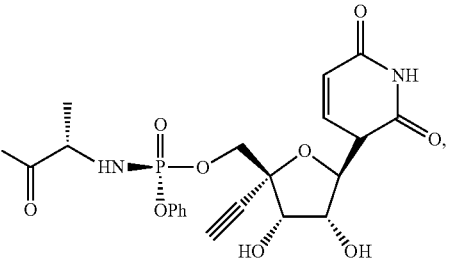
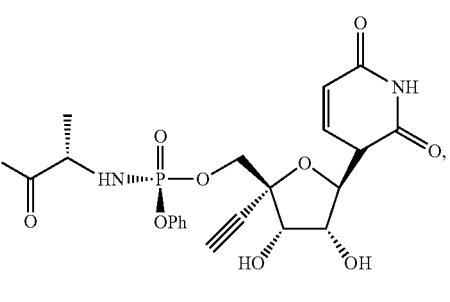

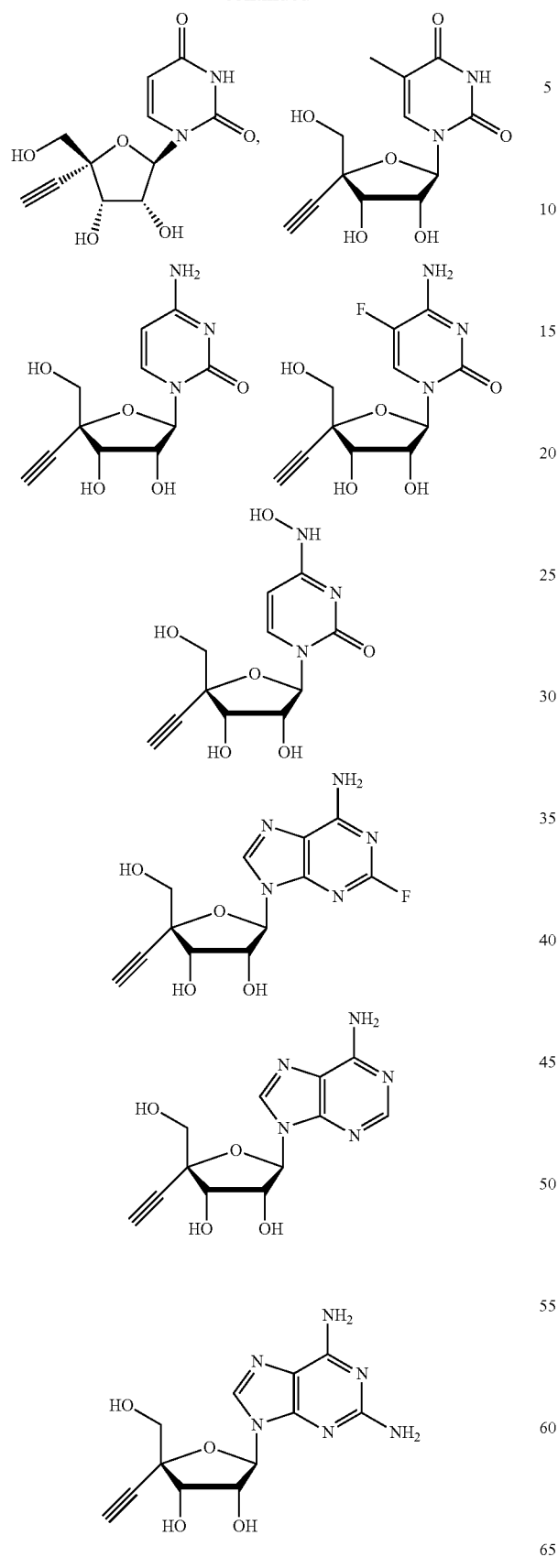
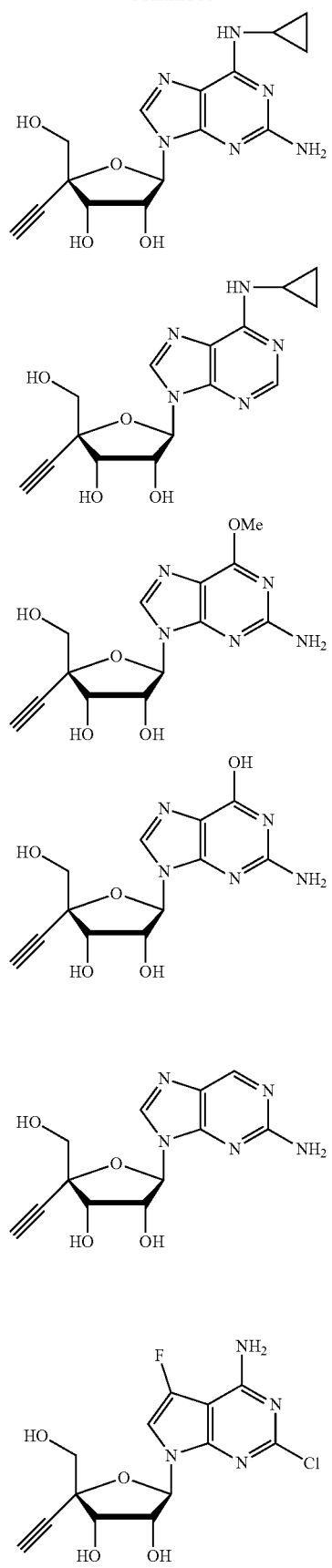

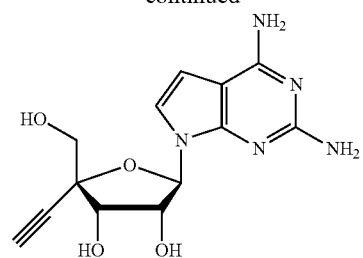
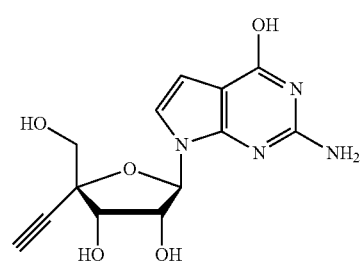
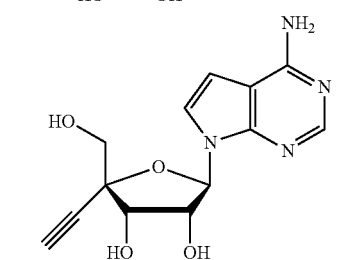
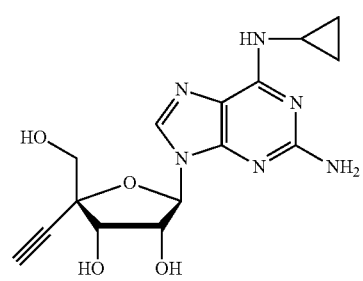
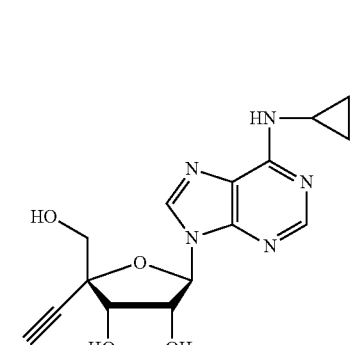
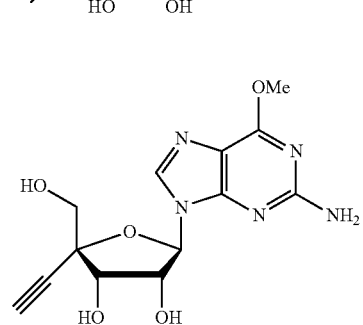
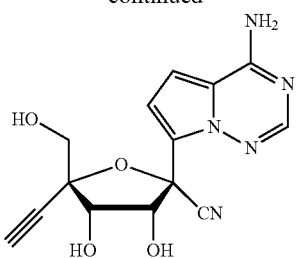
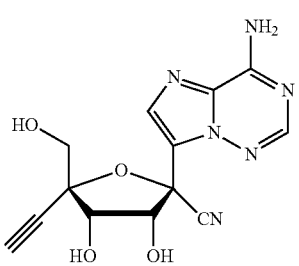
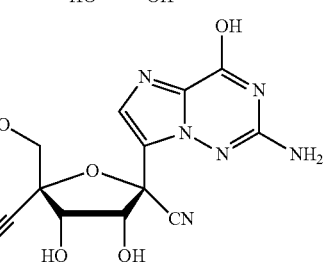
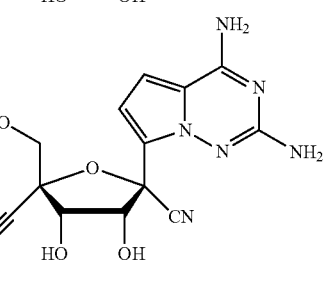
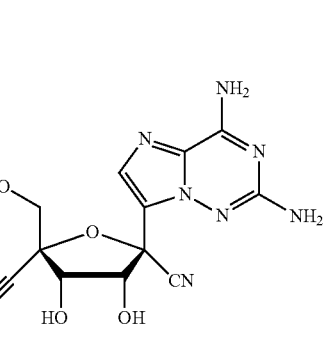
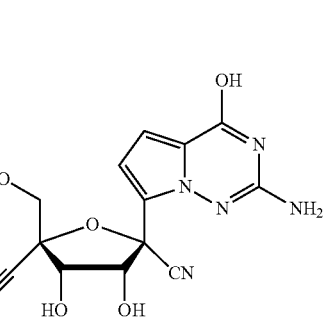

23
-continued

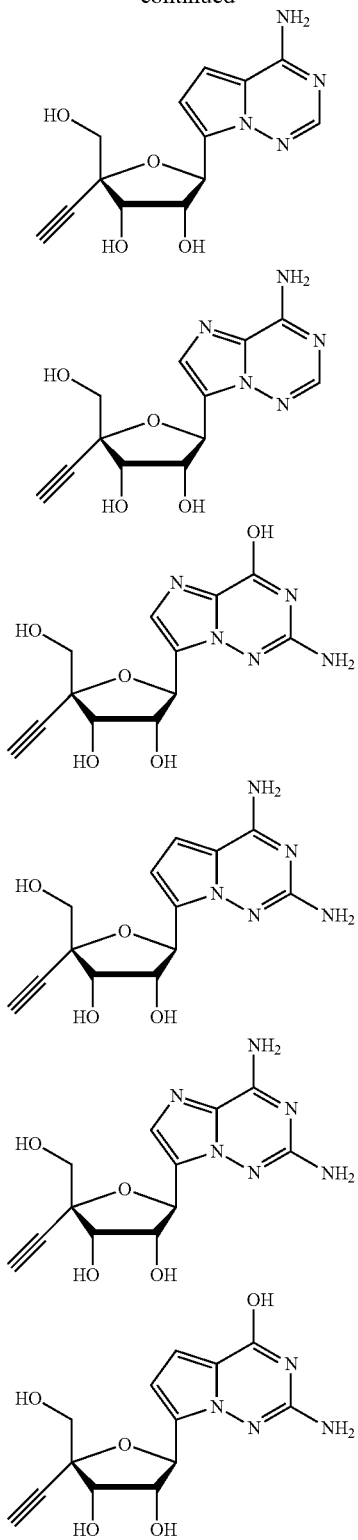

deuterated analogs thereof,
or a pharmaceutically acceptable salt or prodrug thereof.

24

A specific sub-formula is shown below:

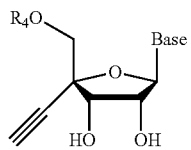

(A)

deuterated analogs thereof,
or a pharmaceutically-acceptable salts or prodrug thereof,
where $R^4$ and Base are as defined above.

A specific compound has the following formula:

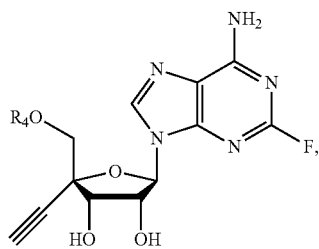

deuterated analogs thereof, or a pharmaceutically acceptable salt or prodrug thereof.

These compounds can be present in the β-D or β-L configuration.

The NOX inhibitors as used herein can be any suitable NOX inhibitor.

Representative NOX inhibitors include AEBSF, Apocyanin, DPI, GK-136901, ML171, Plumbagin, S17834, VAS2870, VAS3947, GKT-831, GKT771, GTL003 or amido thiadiazole derivatives thereof, as described in AU2015365465, EP20140198597; and WO2015/59659, Schisandrin B, as described in CN104147001 and CN20131179455), bi-aromatic and tri-aromatic compounds described in U.S. Publication No. 2015045387, GB 20110016017, and WO201200725, methoxyflavone derivatives described in JP 2015227329, JP 20140097875, and JP 20150093939, peptides, such as NOX2ds-tat and PR-39, as described in U.S. Publication No. 2015368301, TN 2015000295, U.S. Publication No. 201514689803, U.S. Publication No. 201462013916, PCT WO 201450063, and EP 20130150187, piperazine derivatives described in U.S. Publication No. 2014194422, U.S. Pat. No. 9,428,478, U.S. Publication No. 201214123877, U.S. Publication No. 201161496161, and PCT WO 2012US41988, pyrazole derivatives disclosed in KR101280198, KR20110025151, and KR20090082518, pyrazoline dione derivatives disclosed in HK1171748, PCT WO201054329, and EP 20090171466, pyrazolo piperidine derivatives disclosed in KR20130010109, KR20130002317, EP20100153927, PCT WO201150667, EP20100153929, and PCT WO2011IB50668, pyrazolo pyridine derivatives described in KR20170026643, HK1158948, HK1141734, HK1159096, HK1159092, EP20080164857, PCT WO200954156, PCT WO200954150, EP20080164853, PCT WO200853390, U.S. Publication No. 20070896284, EP20070109555, PCT WO 200954148, EP20080164847, PCT WO200954155, and EP20080164849, quinazoline and quinoline derivatives disclosed in EP2886120, U.S. Publication No. 2014018384, U.S. Publication No. 20100407925, EP20110836947, GB20110004600, and PCT WO 201250586, tetrahydroindole derivatives disclosed in U.S.

Publication No. 2010120749, U.S. Pat. No. 8,288,432, U.S. Publication No. 20080532567, EP20070109561, U.S. Publication No. 20070908414, and PCT WO 200853704, tetrahydroisoquinoline derivatives disclosed in U.S. Publication No. 2016083351, U.S. Publication No. 201414888390, U.S. Publication No. 201361818726, and PCT WO 201436402, Scopoletin, described in TW201325588 and TW20110147671, and 2,5-disubstituted benzoxazole and benzothiazole derivatives disclosed in TW201713650 and PCT WO 201554662.

Representative NOX inhibitors also include those disclosed in PCT WO2011062864. In one embodiment, the compound has one the following formulas:

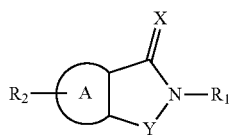

Formula I wherein,

A is a monocyclic or bicyclic aromatic or non-aromatic ring having 5-12 atoms in the ring, wherein the ring optionally has one or more heteroatoms selected from C, O, S, N, and combinations thereof;

$R_1$ is selected from the group consisting of hydrogen, hydroxyl, halogen, alkyl, alkoxy, aryl, alkylaryl, heteroaryl, alkylheteroaryl, heterocyclyl, and alkylheterocyclyl;

$R_2$ is selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, ether, alkylthio, sulfonyl, sulfonamido, ketone, aldehyde, ester, heterocyclyl, aromatic or heteroaromatic moieties, –CF3, and —CN;

X is O, S, or $NR_3$, wherein $R_3$ is OH, alkyl, or substituted or unsubstituted aryl; and Y is C, O, N, $NR_4$, S and Se;

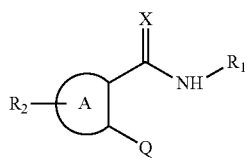

Formula II wherein,

A is a monocyclic or bicyclic aromatic or non-aromatic ring having 5-12 atoms in the ring, wherein the ring optionally has one or more heteroatoms selected from C, O, S, N, and combinations thereof;

$R_1$ is selected from the group consisting of hydrogen, hydroxyl, halogen, alkyl, alkoxy, aryl, alkylaryl, heteroaryl, alkylheteroaryl, heterocyclyl, and alkylheterocyclyl;

$R_2$ is selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, ether, alkylthio, sulfonyl, sulfonamido, ketone, aldehyde, ester, heterocyclyl, aromatic or heteroaromatic moieties, –CF3, and —CN;

X is O, S, or $NR_3$, wherein $R_3$ is OH, alkyl, or substituted or unsubstituted aryl; and Q is alky, hydroxy, ether, ester, carboxylic acid, $NR_4$, $SR_5$, and Se, wherein $R_4$ is H, alkyl, or L-glutathione;

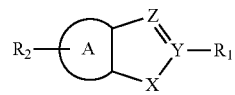

Formula III wherein,

A is a monocyclic or bicyclic aromatic or non-aromatic ring having 5-12 atoms in the ring, wherein the ring optionally has one or more heteroatoms selected from C, O, S, N, and combinations thereof;

$R_1$ is selected from the group consisting of hydrogen, hydroxyl, halogen, alkyl, alkoxy, aryl, alkylaryl, heteroaryl, alkylheteroaryl, heterocyclyl, and alkylheterocyclyl;

$R_2$ is selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, ether, alkylthio, sulfonyl, sulfonamido, ketone, aldehyde, ester, heterocyclyl, aromatic or heteroaromatic moieties, —CF3, and —CN;

X is C, O, N, and $NR_4$, S, and Se; and

Y is O or $NR_3$, wherein $R_3$ is OH, alkyl, or aryl; and

Z is CH, $CH_2$, or N; and

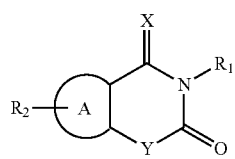

Formula IV wherein,

A is a monocyclic or bicyclic aromatic or non-aromatic ring having 5-12 atoms in the ring, wherein the ring optionally has one or more heteroatoms selected from C, O, S, N, and combinations thereof;

$R_1$ is selected from the group consisting of hydrogen, hydroxyl, halogen, alkyl, alkoxy, aryl, alkylaryl, heteroaryl, alkylheteroaryl, heterocyclyl, and alkylheterocyclyl;

$R_2$ is selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, ether, alkylthio, sulfonyl, sulfonamido, ketone, aldehyde, ester, heterocyclyl, aromatic or heteroaromatic moieties, —CF3, and —CN;

X is O, S, or $NR_3$, wherein $R_3$ is OH, alkyl, or substituted or unsubstituted aryl; and Y is C, O, N, $NR_4$, S or Se, deuterated analogs thereof, or pharmaceutically-acceptable salts or prodrugs thereof.

In certain embodiments, X is O. In certain embodiments, Y is S, N, or Se or Y is S or N. In certain embodiments, A is substituted or unsubstituted phenyl or the phenyl group is substituted with one or more halogen atoms or the phenyl group is substituted with one or more fluorine atoms. In certain embodiments, $R_1$ is aryl optionally substituted with one or more substituents or $R_1$ is substituted or unsubstituted phenyl, thiazolyl, or thiadiazolyl. In certain embodiments $R_1$ is aryl optionally substituted with one or more substituents.

In certain embodiments $R_1$ is aryl or heteroaryl, wherein the aryl or heteroaryl are optionally substituted with alkyl, alkoxy, halogen, cyano, alkylthio, hydroxyalkyl, alkanoyl, alkylcarbonate ester, alkyl carbamoyl amide, aryl, or heterocyclyl wherein these substituents are optionally substituted with alkyl, alkoxy, halogen, cyano, alkylthio, hydroxyalkyl, alkanoyl, alkylcarbonate ester, alkyl carbamoyl amide, aryl, or heterocyclyl.

In certain embodiments, Q is selected from the group consisting of alky, hydroxy, ether, ester, carboxylic acid, $NR_4$, $SR_5$, and Se, wherein $R_4$ is H or alkyl and $R_5$ is H, alkyl, or L-glutathione.

Exemplary Nox inhibitors are listed below:
2-phenylbenzo[d]isothiazol-3(2H)-one,
2-(4-methoxyphenyl)benzo[d]isothiazol-3(2H)-one,
2-(benzo[d][1,3]dioxol-5-yl)benzo[d]isothiazol-3(2H)-one,
2-(2,4-dimethylphenyl)benzo[d]isothiazol-3(2H)-one,
2-(4-fluorophenyl)benzo[d]isothiazol-3(2H)-one,
2-(2,4-dimethylphenyl)-5-fluorobenzo[d]isothiazol-3(2H)-one,
5-fluoro-2-(4-fluorophenyl)benzo[d]isothiazol-3(2H)-one,
2-(2-chloro-6-methylphenyl)-5-fluorobenzo[d]isothiazol-3(2H)-one,
5-fluoro-2-phenylbenzo[d]isothiazol-3(2H)-one,
2-(benzo[d][1,3]dioxol-5-yl)-5-fluorobenzo[d]isothiazol-3(2H)-one,
methyl 4-(3-oxobenzo[d]isothiazol-2(3H)-yl)benzoate,
methyl 4-(5-fluoro-3-oxobenzo[d]isothiazol-2(3H)-yl)benzoate,
ethyl 4-(3-oxobenzo[d]isothiazol-2(3H)-yl)benzoate,
tert-butyl 4-(3-oxobenzo[d]isothiazol-2(3H)-yl)benzoate,
methyl 2-methoxy-4-(3-oxobenzo[d]isothiazol-2(3H)-yl)benzoate,
methyl 3-chloro-4-(3-oxobenzo[d]isothiazol-2(3H)-yl)benzoate,
4-(3-oxobenzo[d]isothiazol-2(3H)-yl)benzonitrile,
methyl 2-(3-oxobenzo[d]isothiazol-2(3H)-yl)benzoate,
2-(4-acetylphenyl)benzo[d]isothiazol-3(2H)-one,
2-(4-nitrophenyl)benzo[d]isothiazol-3(2H)-one,
2-(4-hydroxyphenyl)benzo[d]isothiazol-3(2H)-one,
methyl 6-(3-oxobenzo[d]isothiazol-2(3H)-yl)nicotinate,
6-(3-oxobenzo[d]isothiazol-2(3H)-yl)nicotinonitrile,
2-(4-(hydroxymethyl)phenyl)benzo[d]isothiazol-3(2H)-one,
2-benzylbenzo[d]isothiazol-3(2H)-one,
N-methyl-4-(3-oxobenzo[d]isothiazol-2(3H)-yl)benzamide,
2-(4-hydroxyphenyl)benzo[d]isothiazol-3(2H)-one,
2-(2,4-dimethylphenyl)-1-methyl-1H-indazol-3(2H)-one,
2-(4-fluorophenyl)-1-methyl-1H-indazol-3 (2H)-one,
2-(2,4-dimethylphenyl)-1H-indazol-3(2H)-one,
1-methyl-2-phenyl-1H-indazol-3 (2H)-one,
2-(1,3,4-thiadiazol-2-yl)benzo[d]isothiazol-3(2H)-one,
2-(5-phenyl-1,3,4-thiadiazol-2-yl)benzo[d]isothiazol-3(2H)-one,
2-(5-(ethylthio)-1,3,4-thiadiazol-2-yl)benzo[d]isothiazol-3(2H)-one,
2-(5-(methylthio)-1,3,4-thiadiazol-2-yl)benzo[d]isothiazol-3(2H)-one,
5-fluoro-2-(1,3,4-thiadiazol-2-yl)benzo[d]isothiazol-3(2H)-one,
2-(5-(tert-butyl)-1,3,4-thiadiazol-2-yl)benzo[d]isothiazol-3(2H)-one,
2-(5-(4-bromophenyl)-1,3,4-thiadiazol-2-yl)benzo[d]isothiazol-3(2H)-one
2-(4-methylthiazol-2-yl)benzo[d]isothiazol-3(2H)-one,
2-(4,5-dimethylthiazol-2-yl)benzol[d]isothiazol-3(2H)-one,
2-(benzo[d][1,3]dioxol-5-yl)-4,5-difluorobenzo[d][1,2]selenazol-3(2H)-one,
2-(benzo[d][1,3]dioxol-5-yl)-5-fluorobenzo[d][1,2]selenazol-3(2H)-one,
2-(2,3-dihydrobenzo[b][1,4]dioxin-6-yl)-5-fluorobenzo[d][1,2]selenazol-3(2H)-2-(4-(1,3-dioxolan-2-yl)phenyl)benzo[d][1,2]selenazol-3(2H)-one,
2-(benzo[d][1,3]dioxol-5-yl)-6,7-dimethoxybenzo[d][1,2]selenazol-3(2H)-one,
methyl 4-(3-oxobenzo[d][1,2]selenazol-2(3H)-yl)benzoate,
methyl 4-(3-oxoisothiazolo[5,4-b]pyridin-2(3H)-yl)benzoate, and
methyl 4-(3-oxoisothiazol-2(3H)-yl)benzoate, and pharmaceutically acceptable salts and prodrugs thereof.

Additional representative NOX inhibitors include:

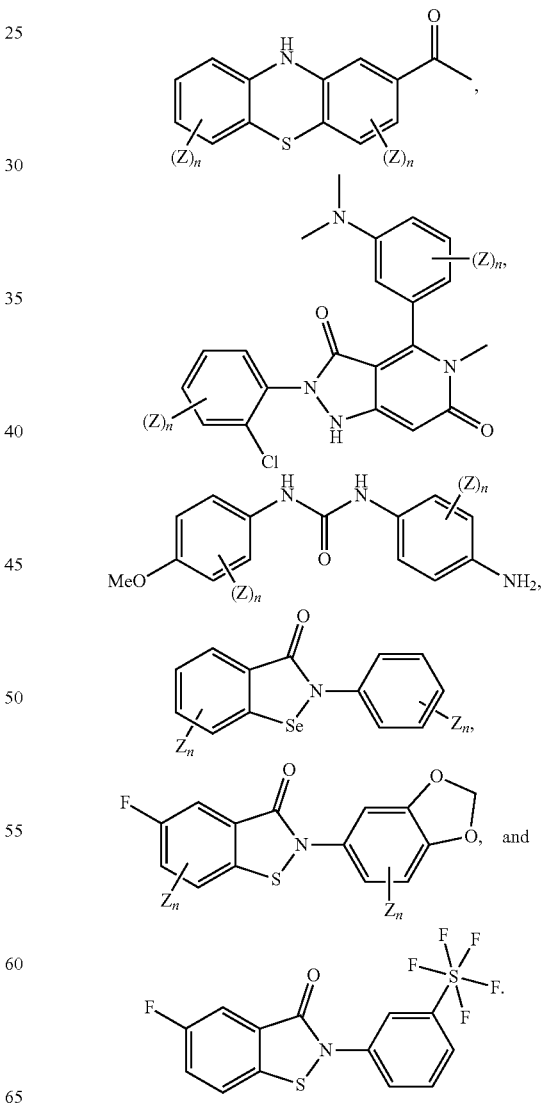

wherein
- Z is selected from the group consisting of $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, heterocyclic, alkylaryl, arylalkyl, hydroxyl, nitro, cyano, cyanoalkyl, azido, azidoalkyl, formyl, hydrazino, halo (F, Cl, Br, or 1), OR', NHR', SR', S(O)R', S(O)$_2$R', S(O)$_2$NHR', S(O)$_2$N(R')R', SF$_5$, COOR', COR', OCOR', NHCOR', N(COR')COR', SCOR', OCOOR', and NHCOOR', wherein each R' is independently H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, wherein the groups can be substituted with one or more substituents as defined above,
- and n is an integer from 0-4,
- or a pharmaceutically acceptable salt or prodrug thereof.

Specific examples of these compounds include

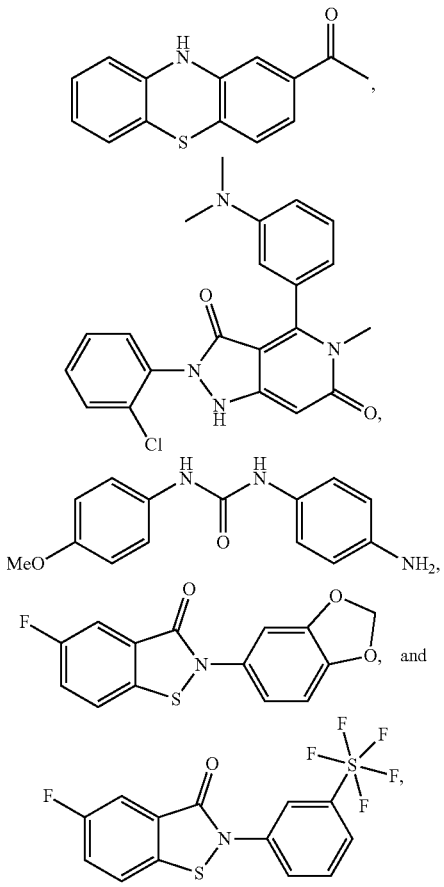

deuterated analogs thereof, or a pharmaceutically acceptable salt or prodrug thereof.

In one embodiment, the NOX inhibitor is Ebselen, Neopterin, APBA, Diapocynin, or a deuterated analog thereof, or a pharmaceutically-acceptable salt or prodrug thereof.

In another embodiment, the NOX compounds are those disclosed in PCT WO 2010/035221, which discloses pyrazolo pyridine derivatives according to Formula (I):

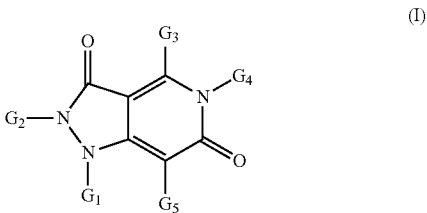

wherein G$_1$ is selected from the group consisting of H; optionally substituted acyl; optionally substituted acyl, $C_{1-6}$ alkyl; optionally substituted alkyl, such as aminocarbonyl alkyl (e.g. phenylacetamide), optionally substituted $C_{3-8}$-cycloalkyl alkyl, optionally substituted heterocycloalkyl alkyl, optionally substituted arylalkyl, such as optionally substituted phenyl alkyl, like optionally substituted phenyl methyl (e.g. phenyl methyl or 3-methyl phenyl methyl or 4-fluorobenzyl or 2-chlorobenzyl or 4-chlorobenzyl or 4-methyl benzyl or 4-bromobenzyl); and optionally substituted heteroaryl alkyl, such as optionally substituted pyridine alkyl like pyridine-2-yl methyl;

G$_2$ is selected from the group consisting of H; optionally substituted $C_{1-6}$ alkyl, such as optionally substituted methyl (e.g. methyl); optionally substituted $C_{2-6}$ alkenyl; optionally substituted $C_{2-6}$ alkynyl; optionally substituted aryl such as optionally substituted phenyl (e.g. phenyl or 4-fluorophenyl or 4-methoxyphenyl or 4-nitrophenyl or 2-chlorophenyl or 3-chlorophenyl or 2-methyl phenyl or 4-(trifluoromethyl) phenyl or 4-(trifluoromethoxy) phenyl or 2,5-difluorophenyl or 2,5-dichlorophenyl or 2-methoxyphenyl or 4-(benzyloxy) phenyl or 3-benzonitrile or 3-phenyl acetamide or 2-chloro-4-fluorophenyl or 3-chloro-4-fluorophenyl or 3,4-dichlorophenyl or 2,3-dichlorophenyl or 2-(benzyloxy)phenyl); optionally substituted $C_{1-6}$ alkyl aryl; optionally substituted aryl $C_{1-6}$ alkyl such as optionally substituted benzyl (e.g. benzyl); optionally substituted heteroaryl such as optionally substituted benzothiazolyl (e.g. 1,3-benzothiazol-2-yl) or optionally substituted pyridinyl (e.g. pyridin-2-yl or (4-methyl piperazin-1-yl)-sulfonylpyridine-2-yl) or optionally substituted thiazolyl (e.g. 4-phenyl-1,3-thiazol-2-yl) or optionally substituted (1,2,4) triazolo(4,3-b)pyridazin-6-yl; optionally substituted $C_{1-6}$ alkyl heteroaryl; optionally substituted heteroaryl $C_{1-6}$ alkyl; optionally substituted $C_{2-6}$ alkenyl aryl; optionally substituted aryl $C_{2-6}$ alkenyl; optionally substituted $C_{2-6}$ alkenyl heteroaryl; optionally substituted heteroaryl $C_{2-6}$ alkenyl; optionally substituted $C_{3-8}$-cycloalkyl such as optionally substituted cyclohexyl (e.g. cyclohexyl); optionally substituted heterocycloalkyl; optionally substituted $C_{1-6}$ alkyl $C_{3-8}$-cycloalkyl; optionally substituted $C_{3-8}$-cycloalkyl $C_{1-6}$ alkyl; optionally substituted $C_{1-6}$ alkyl heterocycloalkyl and optionally substituted heterocycloalkyl $C_{1-6}$ alkyl;

G$_3$ is selected from the group consisting of H; optionally substituted amino; optionally substituted aminoalkyl such as benzyl(methyl)amino methyl; optionally substituted aminocarbonyl; optionally substituted alkoxy; optionally substituted alkoxy $C_{1-6}$ alkyl such as optionally substituted methoxy $C_{1-6}$ alkyl like optionally substituted methoxy methyl (e.g. 4-methoxy methyl), optionally substituted phenoxy $C_{1-6}$ alkyl like optionally substituted phenoxy ethyl (e.g. 3,4-difluorophenoxy)ethyl) or like optionally substituted benzyloxy methyl (e.g. 3-methoxy benzyl); optionally substituted acyl; optionally substituted $C_{1-6}$ alkyl such as methyl, ethyl, butyl; optionally substituted $C_{2-6}$ alkenyl; optionally substituted $C_{2-6}$ alkynyl; optionally substituted aryl such as optionally substituted phenyl (e.g. phenyl or 3-chlorophenyl or 4-chlorophenyl or 2-chlorophenyl or 3-dimethylamino phenyl or 3-morpholin-4-ylphenyl or 2-fluorophenyl); optionally substituted $C_{1-6}$ alkyl aryl; optionally substituted aryl $C_{1-6}$ alkyl such as optionally substituted phenyl $C_{1-6}$ alkyl like optionally substituted benzyl (e.g. 3-methoxy benzyl); optionally substituted heteroaryl; optionally substituted $C_{1-6}$ alkyl heteroaryl; optionally substituted heteroaryl $C_{1-6}$ alkyl; optionally substituted $C_{2-6}$ alkenyl aryl; optionally substituted aryl $C_{2-6}$ alkenyl; optionally substituted $C_{2-6}$ alkenyl heteroaryl; optionally substituted heteroaryl $C_{2-6}$ alkenyl; optionally substituted $C_{3-8}$-cycloalkyl; optionally substituted heterocycloalkyl such as optionally substituted piperidine (e.g. methyl piperidine-1-carboxylate); optionally substituted $C_{1-6}$ alkyl $C_{3-8}$-cycloalkyl; optionally substituted $C_{3-8}$-cycloalkyl $C_{1-6}$alkyl; optionally substituted $C_{1-6}$alkyl heterocycloalkyl and optionally substituted heterocycloalkyl $C_{1-6}$ alkyl such as optionally substituted morpholinyl $C_{1-6}$ alkyl (e.g. morpholin-4ylmethyl);

$G_4$ is selected from the group consisting of —$NR^2$—C(O)—$R^1$ and —$(CHR^3)_m$—$(CH_2)_n$—$R^4$;

$R^1$ is selected from the group consisting of H; optionally substituted amino; —$NR^5R^6$; optionally substituted alkoxy; optionally substituted alkoxy $C_{1-6}$ alkyl such as optionally substituted methoxy (e.g. 4-fluorophenoxy methyl); optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$alkyl; optionally substituted $C_{3-8}$-cycloalkyl; optionally substituted $C_{1-6}$ alkyl $C_3$-8-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl;

$R^2$ is selected from H; optionally substituted alkoxy $C_{1-6}$ alkyl; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$alkyl; optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$alkyl; optionally substituted heterocycloalkyl; optionally substituted $C_{1-6}$ alkyl heterocycloalkyl; optionally substituted heterocycloalkyl $C_{1-6}$ alkyl;

$R^3$ is selected from the group consisting of H; halogen; optionally substituted alkoxy; optionally substituted alkoxy $C_{1-6}$ alkyl; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl; optionally substituted $C_{3-8}$-Cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl;

$R^4$ is selected from the group consisting of H; —C(O)$R^7$; -A-B; —$CHR^8R^9$ and —$(CH_2)_q$-E;

$R^5$ and $R^6$ are independently selected from the group consisting of H; optionally substituted alkoxy $C_{1-6}$ alkyl; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl such as optionally substituted pyridin $C_{1-6}$ alkyl (e.g. pyridine-2-yl-methyl); optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl or —$NR^5R^6$ form together an optionally substituted ring selected from optionally substituted heteroaryl and optionally substituted heterocycloalkyl such as an optionally substituted morpholinyl (e.g. 2-morpholin-4-yl) or an optionally substituted piperazinyl (e.g. 4-methylpiperazin-1-yl or 4-benzylpiperazin-lyl);

$R^7$ is selected from the group consisting of optionally substituted amino; optionally substituted alkoxy such as methoxy; optionally substituted aminoalkyl; optionally substituted alkoxy $C_{1-6}$ alkyl; optionally substituted $C_{1-6}$ alkyl; optionally substituted $C_{2-6}$ alkenyl; optionally substituted $C_{2-6}$ alkynyl; —$NR^5R^6$; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl; optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl such as optionally substituted piperazine (e.g. 4-methylpiperazin-1-yl); optionally substituted $C_{1-6}$ alkyl heterocycloalkyl; and optionally substituted heterocycloalkyl $C_{1-6}$ alkyl;

$R^8$ and $R^9$ are independently selected from the group consisting of optionally substituted aryl such as an optionally substituted phenyl (e.g. phenyl); optionally substituted heteroaryl; optionally substituted $C_{3-8}$-cycloalkyl such as optionally substituted cyclohexyl (e.g. cyclohexyl) and optionally substituted heterocycloalkyl, such as an optionally substituted morpholinyl (e.g. 2-morpholin-4-yl);

$R^{10}$ is selected from H; hydroxyl; optionally substituted amino $C_{1-6}$ alkyl; optionally substituted alkoxy $C_{1-6}$ alkyl; optionally substituted aryl such as optionally substituted phenyl (e.g. phenyl); optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl; optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl;

$R^{11}$ and $R^{12}$ are independently selected from the group consisting of H; optionally substituted acyl such as optionally substituted acetyl (e.g. acetyl); optionally substituted $C_{1-6}$ alkyl such as optionally substituted methyl (e.g. methyl) or optionally substituted ethyl (e.g. ethyl); optionally substituted $C_{2-6}$ alkenyl; optionally substituted $C_{2-6}$ alkynyl; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl;

optionally substituted heteroaryl $C_{1-6}$ alkyl; optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl or —NR$^{11}$R$^{12}$ form together an optionally substituted ring selected from an optionally substituted heteroaryl and optionally substituted heterocycloalkyl such as an optionally substituted morpholinyl (e.g. 2-morpholin-4-yl), optionally substituted pyrrolidinyl (e.g. 6-pyrrolidin-lyl), optionally substituted piperazinyl (e.g. 4-methylpiperazin-1-yl);

R$^{13}$ is selected from the group consisting of optionally substituted aryl such as optionally substituted phenyl (e.g. phenyl); optionally substituted heteroaryl; optionally substituted $C_{3-8}$-cycloalkyl and optionally substituted heterocycloalkyl such as an optionally substituted piperazin (e.g. 4-methyl piperazin) or optionally substituted morpholinyl (e.g. 6-morpholin-4-yl);

R$^{14}$, R$^{15}$ and R$^{16}$ are independently selected from the group consisting of H and optionally substituted $C_{1-6}$ alkyl such as optionally substituted methyl (e.g. methyl) or optionally substituted ethyl (e.g. ethyl);

R$^{17}$ is selected from the group consisting of optionally substituted $C_{1-6}$ alkyl such as optionally substituted methyl (e.g. methyl); optionally substituted $C_{2-6}$ alkenyl; optionally substituted $C_{2-6}$ alkynyl; optionally substituted aryl such as optionally substituted phenyl (e.g. 4-fluorophenyl); optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl; optionally substituted $C_{3-8}$-cycloalkyl; optionally substituted $C_{1-6}$ alkyl $C_{3-8}$-cycloalkyl; optionally substituted $C_{3-8}$-cycloalkyl $C_{1-6}$ alkyl; optionally substituted heterocycloalkyl; optionally substituted $C_{1-6}$ alkyl heterocycloalkyl; and optionally substituted heterocycloalkyl $C_{1-6}$ alkyl;

A is selected from the group consisting of optionally substituted aryl, such as optionally substituted phenyl (e.g. phenyl, methoxy phenyl) and optionally substituted heteroaryl such as optionally substituted pyridine (e.g. pyridin-2-yl);

B is selected from the group consisting of —OR$^{10}$, —NR$^{11}$R$^{12}$ and —(CH$_2$)$_p$—R$^{13}$;

E is selected from the group consisting of optionally substituted $C_{3-8}$-cycloalkyl, such as optionally substituted cyclohexyl (e.g. cyclohexyl); optionally substituted $C_{2-6}$ alkynyl, such as optionally substituted propynyl (e.g. 3-phenylprop-2-yn-1-yl); —NR$^{14}$R$^{15}$; —(CH$_2$)$_r$—OR$^{15}$ and —NR$^{16}$C(O)—R$^{17}$;

m, n, p and q are integers from 0 to 5;

r is an integer from 3 to 5;

G$^5$ is selected from the group consisting of H; optionally substituted $C_{1-6}$ alkyl; optionally substituted $C_{2-6}$ alkenyl; optionally substituted $C_{2-6}$ alkynyl; optionally substituted aryl; optionally substituted $C_{1-6}$ alkyl aryl; optionally substituted aryl $C_{1-6}$ alkyl; optionally substituted heteroaryl; optionally substituted $C_{1-6}$ alkyl heteroaryl; optionally substituted heteroaryl $C_{1-6}$ alkyl; optionally substituted $C_{2-6}$ alkenyl aryl; optionally substituted aryl $C_{2-6}$ alkenyl; optionally substituted $C_{2-6}$ alkenyl heteroaryl; optionally substituted heteroaryl $C_{2-6}$ alkenyl; optionally substituted $C_{3-8}$-cycloalkyl; optionally substituted heterocycloalkyl; optionally substituted $C_{1-6}$ alkyl $C_{3-8}$-cycloalkyl; optionally substituted $C_{3-8}$-cycloalkyl $C_{1-6}$ alkyl; optionally substituted $C_{1-6}$ alkyl heterocycloalkyl and optionally substituted heterocycloalkyl $C_{1-6}$ alkyl; as well as pharmaceutically acceptable salts and pharmaceutically active derivative thereof.

In another embodiment, the pyrazolo pyridine derivative according to Formula (I) is not 1H-Pyrazolo[4,3-c]pyridine-3,6(2H,5H)-dione, 5-(3,3-diphenylpropyl)-4-methyl-2-phenyl-(RN 1010935-27-9).

In another embodiment, the pyrazolo pyridine derivative according to Formula (I) is not 1H-Pyrazolo[4,3-c]pyridine-3,6(2H,5H)-dione, 5-(3,3-diphenylpropyl)-4-methyl-2-phenyl-(RN 1010935-27-9) or 1H-Pyrazolo[4,3-c]pyridine-3,6(2H,5H)-dione, 5-cyclopropyl-4-methyl-2-(4-nitrophenyl)-(RN 1010882-92-4).2013/068972.

In still another embodiment, the compounds are NOX inhibitors disclosed in PCT WO 2013/068972, which are selected from the group consisting of:

4-(2-fluoro-4-methoxyphenyl)-2-(2-methoxyphenyl)-5-(pyridin-3-ylmethyl)-1H-pyrazolo[4,3-c]pyridine-3,6(2H,5H)-dione;

2-(2-chlorophenyl)-4-(4-methoxyphenyl)-5-(pyrazin-2-ylmethyl)-1H-pyrazolo[4,3-c]pyridine-3,6(2H,5H)-dione;

4-(4-chlorophenyl)-2-(2-methoxyphenyl)-5-(pyrazin-2-ylmethyl)-1H-pyrazolo[4,3-c]pyridine-3,6(2H,5H)-dione;

2-(2-chlorophenyl)-4-(2-fluoro-4-methoxyphenyl)-5-[(1-methyl-1H-pyrazol-3-yl) methyl]-1H-pyrazolo[4,3-c]pyridine-3,6(2H,5H)-dione;

4-(2-fluoro-5-methoxyphenyl)-2-(2-methoxyphenyl)-5-(pyridin-3-ylmethyl)-1H-pyrazolo[4,3-c]pyridine-3,6(2H,5H)-dione;

2-(2-chlorophenyl)-5-[(2-methoxypyridin-4-yl)methyl]-4-methyl-1H-pyrazolo[4,3-c] pyridine-3,6(2H,5H)-dione;

2-(2-methoxyphenyl)-4-methyl-5-(pyridin-3-ylmethyl)-1H-pyrazolo [4,3-c]pyridine-3,6(2H,5H)-dione;

4-(4-chloro-2-fluorophenyl)-2-(2-methoxyphenyl)-5-(pyridin-3-ylmethyl)-1H-pyrazolo[4,3-c]pyridine-3,6(2H,5H)-dione;

4-(5-chloro-2-fluorophenyl)-2-(2-chlorophenyl)-5-(pyridin-3-ylmethyl)-1H-pyrazolo [4,3-c]pyridine-3,6(2H,5H)-dione;

2-(2-chlorophenyl)-5-[(6-methoxypyridin-3-yl)methyl]-4-methyl-1H-pyrazolo[4,3-c]pyridine-3,6 (2H,5H)-dione;

4-(4-chloro-2-fluorophenyl)-2-(2-chlorophenyl)-5-(pyridin-3-ylmethyl)-1H-pyrazolo [4,3-c]pyridine-3,6(2H,5H)-dione;

4-(5-chloro-2-fluorophenyl)-2-(2-chlorophenyl)-5-(pyridin-4-ylmethyl)-1H-pyrazolo [4,3-c]pyridine-3,6(2H,5H)-dione;

4-(2-fluoro-5-methoxyphenyl)-2-(2-methoxyphenyl)-5-[(1-methyl-1H-pyrazo-1-3-yl) methyl]-1H-pyrazolo[4,3-c]pyridine-3,6(2H,5H)-dione;

4-(5-chloro-2-fluorophenyl)-2-(2-methoxyphenyl)-5-(pyridin-3-ylmethyl)-1H-pyrazolo[4,3-c]pyridine-3,6(2H, 5H)-dione;

2-(2-chlorophenyl)-4-methyl-5-(pyridin-3-ylmethyl)-1H-pyrazolo[4,3-c]pyridine-3,6 (2H,5H)-dione;

2-(2-chlorophenyl)-4-(4-chlorophenyl)-5-(pyrazin-2-ylmethyl)-1H-pyrazolo[4,3-c]pyridine-3,6 (2H,5H)-dione;

2-(2-chlorophenyl)-4-(2-fluorophenyl)-5-(pyridin-3-ylmethyl)-1H-pyrazolo[4,3-c]pyridine-3,6(2H,5H)-dione;

2-(2-chlorophenyl)-4-(4-chlorophenyl)-5-(pyridin-4-ylmethyl)-1H-pyrazolo[4,3-c]pyridine-3,6(2H,5H)-dione;

4-(4-chloro-2-fluorophenyl)-2-(2-chlorophenyl)-5-(pyridin-4-ylmethyl)-1H-pyrazolo [4,3-c]pyridine-3,6(2H,5H)-dione;

2-(2-methoxyphenyl)-4-(3-methoxyphenyl)-5-[(1-methyl-1H-pyrazo-1-3-yl)methyl]-1H-pyrazolo[4,3-c]pyridine-3,6(2H,5H)-dione;

2-(2-chlorophenyl)-4-(2-fluoro-4-methoxyphenyl)-5-(pyridin-3-ylmethyl)-1H-pyrazolo[4,3-c]pyridine-3,6(2H,5H)-dione;

4-(2-fluoro-4-methoxyphenyl)-2-(2-methoxyphenyl)-5-[(1-methyl-1H-pyrazo-1-3-yl) methyl]-1H-pyrazolo[4,3-c]pyridine-3,6(2H,5H)-dione;

2-(2-methoxyphenyl)-4-(4-methoxyphenyl)-5-[(1-methyl-1H-pyrazo-1-3-yl)methyl]-1H-pyrazolo[4,3-c]pyridine-3,6(2H,5H)-dione;

2-(2-methoxyphenyl)-4-(3-methoxyphenyl)-5-(pyridin-3-ylmethyl)-1H-pyrazolo[4,3-c] pyridine-3,6(2H,5H)-dione;

2-(2-chlorophenyl)-4-(4-chlorophenyl)-5-(pyridin-3-ylmethyl)-1H-pyrazolo[4,3-c]pyridine-3,6(2H,5H)-dione;

4-(4-chloro-2-fluorophenyl)-2-(2-chlorophenyl)-5-[(2-methoxypyridin-4-yl)methyl]-1H-pyrazolo[4,3-c]pyridine-3,6(2H,5H)-dione;

2-(2-chlorophenyl)-4-(2-fluoro-4-methoxyphenyl)-5-(pyridin-4-ylmethyl)-1H-pyrazolo[4,3-c]pyridine-3,6(2H,5H)-dione;

2-(2-chlorophenyl)-4-(2,6-difluorophenyl)-5-(pyridin-4-ylmethyl)-1H-pyrazolo[4,3-c]pyridine-3,6(2H,5H)-dione;

2-(2-chlorophenyl)-4-(2-fluorophenyl)-5-(pyridin-4-ylmethyl)-1H-pyrazolo[4,3-c]pyridine-3,6(2H,5H)-dione;

2-(2-chlorophenyl)-4-methyl-5-[(1-methyl-1H-pyrazol-3-yl)methyl]-1H-pyrazolo[4,3-c] pyridine-3,6(2H,5H)-dione;

4-(3-chloro-2-fluorophenyl)-2-(2-chlorophenyl)-5-(pyridin-4-ylmethyl)-1H-pyrazolo [4,3-c]pyridine-3,6(2H,5H)-dione;

2-(2-chlorophenyl)-5-methyl-4-[3-(methylamino)phenyl]-1H-pyrazolo [4,3-c]pyridine-3,6(2H,5H)-dione;

2-(2-methoxyphenyl)-4-(4-methoxyphenyl)-5-(pyridin-3-ylmethyl)-1H-pyrazolo[4,3-c] pyridine-3,6(2H,5H)-dione;

2-(2-chlorophenyl)-4-(2-fluorophenyl)-5-(pyridin-2-ylmethyl)-1H-pyrazolo[4,3-c]pyridine-3,6(2H,5H)-dione;

2-(2-chlorophenyl)-4-(2,5-difluorophenyl)-5-(pyridin-4-ylmethyl)-1H-pyrazolo[4,3-c]pyridine-3,6(2H,5H)-dione;

2-(2-chlorophenyl)-4-(4-chlorophenyl)-5-(1,3-thiazol-2-ylmethyl)-1H-pyrazolo[4,3-c]pyridine-3,6(2H,5H)-dione;

2-(2-chlorophenyl)-4-[3-(dimethylamino)phenyl]-5-[(1-methyl-1H-pyrazol-3-yl) methyl]-1H-pyrazolo[4,3-c] pyridine-3,6(2H,5H)-dione;

2-(2-chlorophenyl)-4-(3,5-dichlorophenyl)-5-(pyridin-4-ylmethyl)-1H-pyrazolo[4,3-c]pyridine-3,6(2H,5H)-dione;

4-(3-chloro-2-fluorophenyl)-2-(2-chlorophenyl)-5-(pyridin-3-ylmethyl)-1H-pyrazolo [4,3-c]pyridine-3,6(2H,5H)-dione;

2-(2-chlorophenyl)-4-[3-(dimethylamino)phenyl]-5-(pyridin-3-ylmethyl)-1H-pyrazolo [4,3-c]pyridine-3,6(2H,5H)-dione;

2-(2-chlorophenyl)-4-(2,6-difluorophenyl)-5-(pyridin-3-ylmethyl)-1H-pyrazolo[4,3-c]pyridine-3,6(2H,5H)-dione;

4-(2-fluoro-5-methoxyphenyl)-2-(2-methoxyphenyl)-5-(pyrazin-2-ylmethyl)-1H-pyrazolo[4,3-c]pyridine-3,6(2H,5H)-dione;

2-(2-chlorophenyl)-4-(2,5-difluorophenyl)-5-(pyridin-3-ylmethyl)-1H-pyrazolo[4,3-c]pyridine-3,6(2H,5H)-dione; and 2-(2-chlorophenyl)-4-[3-(dimethylamino)phenyl]-5-[(1-methyl-1H-pyrazol-3-yl) methyl]-1H-pyrazolo[4,3-c] pyridine-3,6(2H,5H)-dione.

In a further embodiment, the compounds are Ebsalen analogs having the following formula:

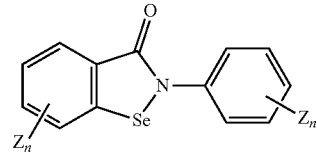

where Z and n are as defined elsewhere herein, and R is selected from the group consisting of H, substituted or unsubstituted $C_{1-6}$ alkyl, $C_{1-6}$ haloalkyl, $C_{1-6}$ alkoxy, substituted or unsubstituted $C_{2-6}$ alkenyl, substituted or unsubstituted $C_{2-6}$ alkynyl, substituted or unsubstituted $C_{3-6}$ cycloalkyl, aryl, heteroaryl, heterocyclic, alkylaryl, or arylalkyl, wherein the aryl, alkenyl, alkynyl, cycloalkyl, heteroaryl, heterocyclic alkylaryl or arylalkyl groups can optionally be substituted with a group selected from the group consisting of hydroxyl, halogen, amino, alkylamino, arylamino, alkoxy, aryloxy, nitro, cyano, sulfonic acid, sulfate, phosphonic acid, phosphate, phosphonate, nitro, cyano, cyanoalkyl, azido, azidoalkyl, formyl, hydrazino, OR', SR', COOR', COR', OCOR', NHCOR', N(COR')COR', SCOR', OCOOR', and NHCOOR', wherein each R' is independently H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl.

These Ebsalen analogs can generally be prepared using the following synthesis:

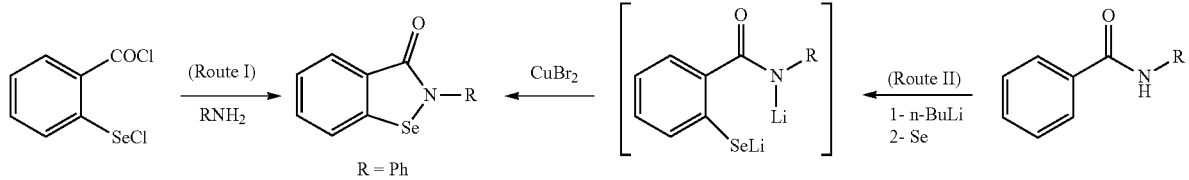

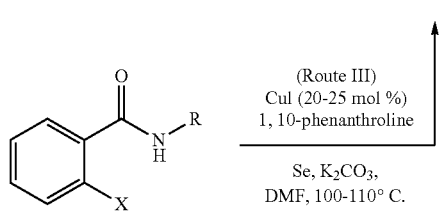

X = Cl, Br, I (Route III)
CuI (20-25 mol %)
1, 10-phenanthroline

Se, K₂CO₃,
DMF, 100-110° C.

Where Z is present on one or both of the aromatic rings, it can be present on the starting material, or added after the final coupling step which forms the N—Se bond.

In another embodiment, the compounds have the following formula:

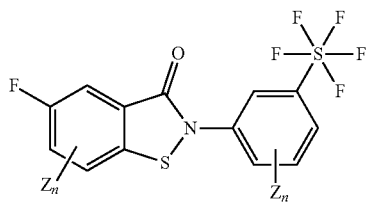

where Z and N are as defined elsewhere herein. These compounds can be prepared using the following synthetic strategy:

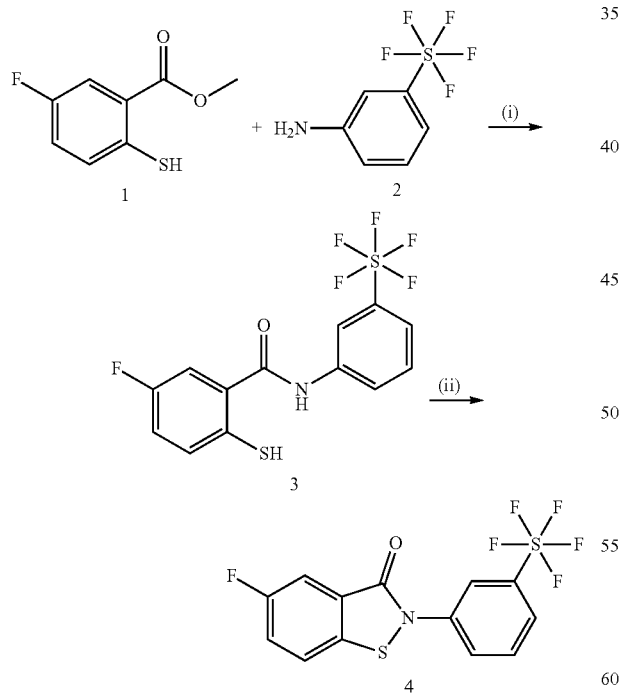

(i) AlMe₃, DCM, reflux, overnight, 64%
(ii) PIFA, DCM, TFA, 0° C. to rt, 12 h, 55%.

Where Z is present on one or both of the aromatic rings, it can be present on the starting material, or added after the final coupling step which forms the N—S bond.

III Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.
i) physical separation of crystals: a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization: a technique whereby the individual enantiomers are separately crystallized from a solution of the racemate, possible only if the latter is a conglomerate in the solid state;
iii) enzymatic resolutions: a technique whereby partial or complete separation of a racemate by virtue of differing rates of reaction for the enantiomers with an enzyme;
iv) enzymatic asymmetric synthesis: a synthetic technique whereby at least one step of the synthesis uses an enzymatic reaction to obtain an enantiomerically pure or enriched synthetic precursor of the desired enantiomer;
v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;
vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts. For certain transdermal applications, it can be preferred to use fatty acid salts of the compounds described herein. The fatty acid salts can help penetrate the stratum corneum. Examples of suitable salts include salts of the compounds with stearic acid, oleic acid, lineoleic acid, palmitic acid, caprylic acid, and capric acid.

Pharmaceutically acceptable salts can be obtained using standard procedures well known in the art, for example by reacting a sufficiently basic compound such as an amine with a suitable acid, affording a physiologically acceptable anion. In those cases where a compound includes multiple amine groups, the salts can be formed with any number of the amine groups. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Methods of Treatment

There is a broad consensus that macrophages resist HIV-1 infection much better than CD4+ T cells. Among other reasons, this is due to the presence of the recently identified host cell restriction factor SamHD1, which is strongly expressed in cells of the myeloid lineage.

Hosts, including but not limited to humans infected with HIV or other viral infections that infect macrophages can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, transdermally, subcutaneously, or topically, in liquid or solid form.

The nucleoside compounds described herein can be used to treat or prevent HIV, or reduce the activity of HIV in a host, particularly the HIV located in the macrophages. As discussed in more detail below, the compounds can be administered in combination or alternation with other antiviral compounds, such as other anti-HIV compounds, including HAART therapy, as well as the NOX inhibitors described herein.

The nicotinamide adenine dinucleotide phosphate oxidase (NADPH Oxidase, NOX) inhibitors can treat or prevent infections by HIV or other viruses that target (and thus infect) the macrophages, or reduce the activity of these viruses, when an effective amount of the active compound or a pharmaceutically acceptable prodrug or salt thereof is administered to a patient in need of treatment thereof, optionally in the presence of a pharmaceutically acceptable carrier or diluent.

Representative viral infections include viruses from the arenavirus, herpesviridae, filoviridae, rhabdoviridae, coronaviridae, paramyxoviridae, polyomaviridae, picornaviridae, bunyaviridae, caliciviridae, flaviviridae, hepadnaviridae, orthomyxoviridae, retroviridae, and togaviridae families. For example, the arenavirus can be Junin, Machupo, Guanarito, Lassa, or Lujo viruses, the herpesviridae virus can be human herpesvirus 1, 2, 3, 4, 5, 6, 7, or 8, the filoviridae virus can be ebolavirus or Marburg virus, the rhabdoviridae can be the rabies virus or the Australian bat lyssavirus, the coronaviridae virus can be the human coronavirus 229E or human coronavirus NL63, the paramyxoviridae virus can be mumps rubulavirus, the polyomaviridae virus can be the JC virus or the BK virus, the picornaviridae virus can be foot-and-mouth disease virus, enterovirus68, enterovirus 71, enterovirus C (poliovirus) or rhinovirus, the bunyaviridae virus can be hanta virus, rift valley fever virus, or crimean-congo hemorrhagic fever virus, the caliciviridae virus is Norwalk virus or norovirus, the flaviviridae virus can be Dengue virus, Deer-tick encephalitis virus, japanese encephalitis virus, murray valley encephalitis virus, omsk hemorrhagic fever virus, Powassan virus, St. Louis encephalitis virus, ticket-borne encephalitis virus, west nile virus, yellow fever virus, zika virus, or hepatitis C, the hepadnaviridae virus can be hepatitis B; the orthomyxoviridae virus can be influenza A, influenza B, or influenza C; the retroviridae virus can be human immunodeficiency virus 1, human immunodeficiency virus 2, or human T-lymphotrophic virus; and the togaviridae virus can be chikungunya virus, mayaro virus, sindbis virus, or venezuelan equine encephalitis virus.

Various nanoparticle formulations are described herein, and, depending on the particle size, ligands such as antibodies or polyethylene glycol chains attached to the nanoparticles, the therapy can be specifically delivered to various organs, including the lungs, liver, and brain. This can be particularly important in delivering drugs to the macrophages, where the particles are of a size that enables them to be phagocytosed by the macrophages, and phagocytosis can assist in delivering the drugs inside the macrophages. The liver is a major source of macrophages, so targeted delivery to the liver can be beneficial. It is also useful to deliver agents in a form which enables them to cross the blood-brain barrier, so as to treat macrophages present in the brain.

VI. Combination or Alternation Therapy

In one embodiment, the compounds of the invention can be employed together with at least one other antiviral agent, selected from the group consisting of Nucleoside Reverse Transcriptase Inhibitors (NRTIs), Nonnucleoside Reverse Transcriptase Inhibitors (NNRTIs), Fusion Inhibitors, Entry Inhibitors, CCR5 co-receptor antagonist and HIV integrase strand transfer inhibitors, anti-inflammatories including Jak inhibitors including but not limited to tofacitinib, baricitinib, ruxolitinib, or other immunomodulators, dasatinib, MAPK inhibitors, mTOR inhibitors, β-catenin inhibitors, interferon inhibitors, interferon, HDAC inhibitors, PKC agonists, TLR4 agonists, or other reactivation agents for HIV infection and latency.

For example, when used to treat or prevent HIV infection, the active compound or its prodrug or pharmaceutically acceptable salt can be administered in combination or alternation with another anti-HIV including, but not limited to, those described below. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

TABLE 1

FDA-Approved multi class combination products used in the Treatment of HIV Infection.

| Brand | Generic Name |
| --- | --- |
| Atripla | efavirenz, emtricitabine and tenofovir disoproxil fumarate |
| Complera | emtricitabine, rilpivirine, and tenofovir disoproxil fumarate |
| Evotaz | atazanavir sulfate, combicistat |
| Prezcobix | cobicistat, darunavir ethanolate |
| Stribild | elvitegravir, cobicistat, emtricitabine, tenofovir disoproxil fumarate |

TABLE 2

FDA-Approved Nucleoside Reverse Transcriptase Inhibitors (NRTIs) used in the Treatment of HIV Infection.

| Brand Name | Generic Name |
| --- | --- |
| Combivir | lamivudine and zidovudine |
| Emtriva | emtricitabine, FTC |
| Epivir | lamivudine, 3TC |
| Epzicom | abacavir and lamivudine |
| Hivid | zalcitabine, dideoxycytidine, ddC (no longer marketed) |
| Retrovir | zidovudine, azidothymidine, AZT, ZDV |
| Trizivir | abacavir, zidovudine, and lamivudine |
| Truvada | tenofovir disoproxil fumarate and emtricitabine |
| Videx EC | enteric coated didanosine, ddI EC |
| Videx | didanosine, dideoxyinosine, ddI |
| Viread | tenofovir disoproxil fumarate, TDF |
| Zerit | stavudine, d4T |
| Ziagen | abacavir sulfate, ABC |

TABLE 3

FDA-Approved Nonnucleoside Reverse Transcriptase Inhibitors (NNRTIs) used in the Treatment of HIV Infection.

| Brand Name | Generic Name |
| --- | --- |
| Edurant | rilpivirine |
| Intelence | etravirine |
| Rescriptor | delavirdine, DLV |
| Sustiva | efavirenz, EFV |
| Viramune (Immediate Release) | nevirapine, NVP |
| Viramune XR (Extended Release) | nevirapine, NVP |

TABLE 4

FDA-Approved Protease Inhibitors (PIs) used
in the Treatment of HIV Infection.

| Brand Name | Generic Name |
| --- | --- |
| Agenerase | amprenavir, APV (no longer marketed) |
| Aptivus | tipranavir, TPV |
| Crixivan | indinavir, IDV, |
| Fortovase | saquinavir (no longer marketed) |
| Invirase | saquinavir mesylate, SQV |
| Kaletra | lopinavir and ritonavir, LPV/RTV |
| Lexiva | Fosamprenavir Calcium, FOS-APV |
| Norvir | ritonavir, RTV |
| Prezista | darunavir |
| Reyataz | atazanavir sulfate, ATV |
| Viracept | nelfinavir mesylate, NFV |

TABLE 5

FDA-Approved Fusion Inhibitors used
in the Treatment of HIV Infection.

| Brand Name | Generic Name |
| --- | --- |
| Fuzeon | enfuvirtide, T-20 |

TABLE 6

FDA-Approved Entry Inhibitors-CCR5 co-receptor antagonist
used in the Treatment of HIV Infection.

| Brand Name | Generic Name |
| --- | --- |
| Selzentry | maraviroc |

TABLE 7

FDA-Approved HIV integrase strand transfer inhibitors
used in the Treatment of HIV Infection.

| Brand Name | Generic Name |
| --- | --- |
| Isentress | raltegravir |
| Tivicay® | dolutegravir |
| Vitekta | elvitegravir |

Additional compounds which can be used in combination therapy include:
EFdA, Anti-inflammatories including Jak inhibitors including but not limited to tofacitinib, dasatinib, MAPK inhibitors, mTOR inhibitors, β-catenin inhibitors, interferon inhibitors, interferon, HDAC inhibitors, PKC agonists, TLR4 agonists, or other reactivation agents for HIV infection and latency.

VIII. Pharmaceutical Compositions

Hosts, including but not limited to humans, infected with HIV or the other viruses described herein can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 600 mg, preferably 70 to 600 mg of active ingredient per unit dosage form. An oral dosage of 5-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is that described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring. Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions. In one embodiment, controlled release nanoparticulate formulations comprise a nanoparticulate active agent to be administered and a rate-controlling polymer which prolongs the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions can comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxy-poly-(glycidol), SA9OHCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid) (PLGA)-nanoparticles are known to target the liver when given by intravenous (IV) or subcutaneously (SQ).

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Nonionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Certain nanoformulations can enhance the absorption of drugs by releasing drug into the lumen in a controlled manner, thus reducing solubility issues. The intestinal wall is designed to absorb nutrients and to act as a barrier to pathogens and macromolecules. Small amphipathic and lipophilic molecules can be absorbed by partitioning into the lipid bilayers and crossing the intestinal epithelial cells by passive diffusion, while nanoformulation absorption may be more complicated because of the intrinsic nature of the intestinal wall. The first physical obstacle to nanoparticle oral absorption is the mucus barrier which covers the luminal surface of the intestine and colon. The mucus barrier contains distinct layers and is composed mainly of heavily glycosylated proteins called mucins, which have the potential to block the absorption of certain nanoformulations. Modifications can be made to produce nanoformulations with increased mucus-penetrating properties (Ensign et al., "Mucus penetrating nanoparticles: biophysical tool and method of drug and gene delivery," Adv Mater 24: 3887-3894 (2012)).

Once the mucus coating has been traversed, the transport of nanoformulations across intestinal epithelial cells can be regulated by several steps, including cell surface binding, endocytosis, intracellular trafficking and exocytosis, resulting in transcytosis (transport across the interior of a cell) with the potential involvement of multiple subcellular structures. Moreover, nanoformulations can also travel between cells through opened tight junctions, defined as paracytosis. Non-phagocytic pathways, which involve clathrin-mediated and caveolae-mediated endocytosis and macropinocytosis, are the most common mechanisms of nanoformulation absorption by the oral route.

Non-oral administration can provide various benefits, such as direct targeting to the desired site of action and an extended period of drug action. Transdermal administration has been optimized for nanoformulations, such as solid lipid nanoparticles (SLNs) and NEs, which are characterized by good biocompatibility, lower cytotoxicity and desirable drug release modulation (Cappel and Kreuter, "Effect of nanoparticles on transdermal drug delivery. J Microencapsul 8: 369-374 (1991)). Nasal administration of nanoformulations allows them to penetrate the nasal mucosal membrane, via a transmucosal route by endocytosis or via a carrier- or receptor-mediated transport process (Illum, "Nanoparticulate systems for nasal delivery of drugs: a real improvement over simple systems?" J. Pharm. Sci 96: 473-483 (2007)), an example of which is the nasal administration of chitosan nanoparticles of tizanidine to increase brain penetration and drug efficacy in mice (Patel et al., "Improved transnasal transport and brain uptake of tizanidine HCl-loaded thiolated chitosan nanoparticles for alleviation of pain," J. Pharm. Sci 101: 690-706 (2012)). Pulmonary administration provides a large surface area and relative ease of access. The mucus barrier, metabolic enzymes in the tracheobronchial region and macrophages in the alveoli are typically the main barriers for drug penetration. Particle size is a major factor determining the diffusion of nanoformulation in the bronchial tree, with particles in the nano-sized region more likely to reach the alveolar region and particles with diameters between 1 and 5 m expected to deposit in the bronchioles (Musante et al., "Factors affecting the deposition of inhaled porous drug particles," J Pharm Sci 91: 1590-1600 (2002)). A limit to absorption has been shown for larger particles, presumably because of an inability to cross the air-blood barrier. Particles can gradually release the drug, which can consequently penetrate into the blood stream or, alternatively, particles can be phagocytosed by alveolar macrophages (Bailey and Berkland, "Nanoparticle formulations in pulmonary drug delivery," Med. Res. Rev., 29: 196-212 (2009)).

Certain nanoformulations have a minimal penetration through biological membranes in sites of absorption and for these, i.v. administration can be the preferred route to obtain an efficient distribution in the body (Wacker, "Nanocarriers for intravenous injection—The long hard road to the market," Int. J. Pharm., 457: 50-62., 2013).

The distribution of nanoformulations can vary widely depending on the delivery system used, the characteristics of the nanoformulation, the variability between individuals, and the rate of drug loss from the nanoformulations. Certain nanoparticles, such as solid drug nanoparticles (SDNs), improve drug absorption, which does not require them to arrive intact in the systemic circulation. Other nanoparticles survive the absorption process, thus altering the distribution and clearance of the contained drug.

Nanoformulations of a certain size and composition can diffuse in tissues through well-characterized processes, such as the enhanced permeability and retention effect, whereas others accumulate in specific cell populations, which allows one to target specific organs. Complex biological barriers can protect organs from exogenous compounds, and the blood-brain barrier (BBB) represents an obstacle for many therapeutic agents. Many different types of cells including endothelial cells, microglia, pericytes and astrocytes are present in the BBB, which exhibits extremely restrictive tight junctions, along with highly active efflux mechanisms, limiting the permeation of most drugs. Transport through the BBB is typically restricted to small lipophilic molecules and nutrients that are carried by specific transporters. One of the most important mechanisms regulating diffusion of nanoformulations into the brain is endocytosis by brain capillary endothelial cells.

Recent studies have correlated particle properties with nanoformulation entry pathways and processing in the human BBB endothelial barrier, indicating that uncoated nanoparticles have limited penetration through the BBB and that surface modification can influence the efficiency and mechanisms of endocytosis (Lee et al., "Targeting rat antimouse transferrin receptor monoclonal antibodies through blood-brain barrier in mouse," J. Pharmacol. Exp. Ther. 292: 1048-1052 (2000)). Accordingly, surface-modified nanoparticles which cross the BBB, and deliver one or more of the compounds described herein, are within the scope of the invention.

Macrophages in the liver are a major pool of the total number of macrophages in the body. Kupffer cells in the liver possess numerous receptors for selective phagocytosis of opsonized particles (receptors for complement proteins and for the fragment crystallizable part of IgG). Phagocytosis can provide a mechanism for targeting the macrophages, and providing local delivery (i.e., delivery inside the macrophages) of the compounds described herein (TRUE?).

Nanoparticles linked to polyethylene glycol (PEG) have minimal interactions with receptors, which inhibits phagocytosis by the mononuclear phagocytic system (Bazile et al., "Stealth Me.PEG-PLA nanoparticles avoid uptake by the mononuclear phagocytes system," J. Pharm. Sci. 84: 493-498 (1995)).

Representative nanoformulations include inorganic nanoparticles, SDNs, SLNs, NEs, liposomes, polymeric nanoparticles and dendrimers. The compounds described herein can be contained inside a nanoformulation, or, as is sometimes the case with inorganic nanoparticles and dendrimers, attached to the surface. Hybrid nanoformulations, which contain elements of more than one nanoformulation class, can also be used.

SDNs are lipid-free nanoparticles, which can improve the oral bioavailability and exposure of poorly water-soluble drugs (Chan, "Nanodrug particles and nanoformulations for drug delivery," Adv. Drug. Deliv. Rev. 63: 405 (2011)). SDNs include a drug and a stabilizer, and are produced using 'top-down' (high pressure homogenization and wet milling) or bottom-up (solvent evaporation and precipitation) approaches.

SLNs consist of a lipid (or lipids) which is solid at room temperature, an emulsifier and water. Lipids utilized include, but are not limited to, triglycerides, partial glycerides, fatty acids, steroids and waxes. SLNs are most suited for delivering highly lipophilic drugs.

Liquid droplets of less than a 1000 nm dispersed in an immiscible liquid are classified as NEs. NEs are used as carriers for both hydrophobic and hydrophilic agents, and can be administered orally, transdermally, intravenously, intranasally, and ocularly. Oral administration can be preferred for chronic therapy, and NEs can effectively enhance oral bioavailability of small molecules, peptides and proteins.

Polymeric nanoparticles are solid particles typically around 200-800 nm in size, which can include synthetic and/or natural polymers, and can optionally be pegylated to minimize phagocytosis. Polymeric nanoparticles can increase the bioavailability of drugs and other substances, compared with traditional formulations. Their clearance depends on several factors, including the choice of polymers (including polymer size, polymer charge and targeting ligands), with positively charged nanoparticles larger than 100 nm being eliminated predominantly via the liver (Alexis et al., Factors affecting the clearance and biodistribution of polymeric nanoparticles. Mol Pharm 5: 505-515 (2008)).

Dendrimers are tree-like, nanostructured polymers which are commonly 10-20 nm in diameter.

Liposomes are spherical vesicles which include a phospholipid bilayer. A variety of lipids can be utilized, allowing for a degree of control in degradation level. In addition to oral dosing, liposomes can be administered in many ways, including intravenously (McCaskill et al., 2013), transdermally (Pierre and Dos Santos Miranda Costa, 2011), intravitreally (Honda et al., 2013) and through the lung (Chattopadhyay, 2013). Liposomes can be combined with synthetic polymers to form lipid-polymer hybrid nanoparticles, extending their ability to target specific sites in the body. The clearance rate of liposome-encased drugs is determined by both drug release and destruction of liposomes (uptake of liposomes by phagocyte immune cells, aggregation, pH-sensitive breakdown, etc.) (Ishida et al., "Liposome clearance," Biosci Rep 22: 197-224 (2002)).

One of more of these nanoparticulate formulations can be used to deliver the active agents described herein to the macrophages, across the blood brain barrier, and other locations as appropriate.

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:
DMSO dimethylsulfoxide
EtOAc ethyl acetate
h hour
Liq. liquid
M molar
MeOH Methanol
min minute
rt or RT room temperature
TBAF Tetrabutylammonium fluoride
THF tetrahydrofuran IX. General Methods for Preparing Active Compounds Methods for the facile preparation of active compounds are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 1 is a synthetic approach to nucleosides 3. (Base and other variables listed in the Scheme are as defined in active compound section)

Scheme 2 is an alternate synthetic approach to nucleosides 3. (Base and other variables listed in the Scheme are as defined in active compound section)

Schemes 3 and 4 are generalized schemes for preparing 4'-ethynyl uracil and ribo thymidine compounds.

Schemes 5-11 are generalized schemes for preparing 4'-C-Ethynyl-β-D-arabino- and 4'-C-Ethynyl-2'-deoxy-β-D-ribo-pentofuranosylpyrimidines and -purines.

Scheme 12 is a synthetic approach to 4'-Ethynyl-2-Fluoro-Adenosine (7)

Scheme 13 is a synthetic approach to Compound 4 (the Ebsalen analog with $SF_5$ substitution).

Compounds of Formula A can be prepared by first preparing nucleosides 1, which in turn can be accomplished by one of ordinary skill in the art, using methods outlined in: (a) Rajagopalan, P.; Boudinot, F. D; Chu, C. K.; Tennant, B. C.; Baldwin, B. H.; Antiviral Nucleosides: Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, GA, USA, pp: 319-37 d) Handbook of Nucleoside Synthesis: Vorbruggen H. & Ruh-Pohlenz C. John Wiley & sons 2001), and by general Schemes 1-2. Specifically, nucleosides 3 can be prepared by coupling sugar 1 with a protected, silylated or free nucleoside base in the presence of Lewis acid such as TMSOTf. Deprotection of the 3'- and 5'-hydroxyls gives nucleoside 3.

Analogous compounds of Formula B can be prepared using compounds like Compound 1, but with a fluorine rather than OPr at the 2'-position. Representative synthetic methods are described, for example, in U.S. Pat. No. 8,716,262.

Scheme 1

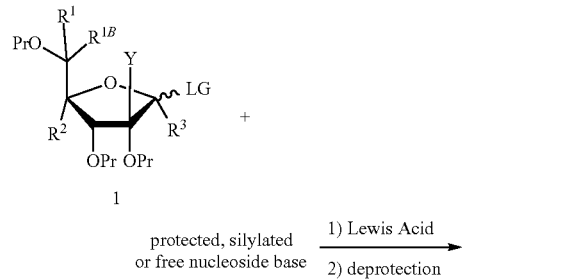

nucleoside base may contain suitable protection;
Pr = protection;
LG = OCOalkyl, OCOaryl, OCOalkylaryl;
$R^1$, $R^{1B}$, $R^2$, $R^3$, and Y are as defined in active compound section Similarly, compounds like Compound 1, but with a Y substituent at the 2'-position and/or an R substituent at the 3'-position, can be used to prepare nucleosides similar to Compound 3, but with Y or R substitution at the 2'- and/or 3'-positions, respectively.

Also, analogous compounds where the oxygen in the sugar ring is replaced with one of the other variables defined by $R^5$ can also be prepared.

Scheme 2 A Synthetic Approach to Nucleosides 3. (Base are as Defined in Active Compound Section)

In the schemes described herein, if a nucleoside base includes functional groups that might interfere with, or be decomposed or otherwise converted during the coupling steps, such functional groups can be protected using suitable protecting groups. After the coupling step, protected functional groups, if any, can be deprotected.

Alternatively, nucleosides 3 can be prepared from 1'-halo, 1'-sulfonate or 1'-hydroxy compounds 2. For the case of 1'-halo or 1'-sulfonate a protected or free nucleoside base in the presence of a base such as triethyl amine or sodium hydride followed by deprotection would give nucleosides 3. For the case of 1'-hydroxy a protected or free nucleoside base in the presence of a Mitsunobu coupling agent such as diisopropyl azodicarboxylate followed by deprotection would give nucleosides 3.

Analogous compounds of Formula B can be prepared using compounds like Compound 1, but with a fluorine rather than OPr at the 2'-position. Representative synthetic methods are described, for example, in U.S. Pat. No. 8,716,262.

Scheme 2 An alternate synthetic approach to nucleoside 3. (Base, $R^1$,$R^{1B}$,$R^2$, and $R^3$ are as defined in active compound section)

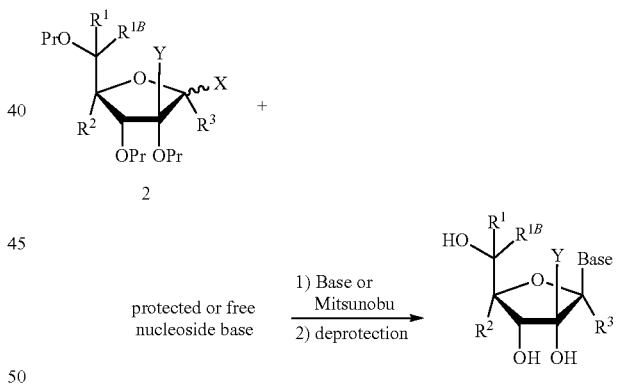

nucleoside base may contain suitable protection;
Pr = protection;
X = halogen, sulfonate or OH;
$R^1$, $R^{1B}$,$R^2$,$R^3$, and Y are as defined in active compound section Similarly, compounds like Compound 2, but with a Y substituent at the 2'-position and/or an R substituent at the 3'-position, can be used to prepare nucleosides similar to Compound 3, but with Y or R substitution at the 2'- and/or 3'-positions, respectively.

Also, analogous compounds where the oxygen in the sugar ring is replaced with one of the other variables defined by $R^5$ can also be prepared.

In the case of C-nucleosides prepared from bases: 1)
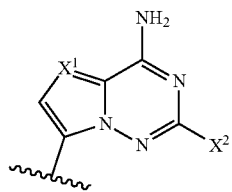
and 2)
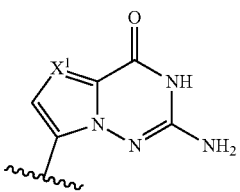
methods outlined in WO09132123, WO09132135, WO2011150288 and WO2011035250 can be used.
A more specific approach to forming 4'-ethynyl uracil and 2'-ribo thymidine compounds is provided below in Scheme 3:
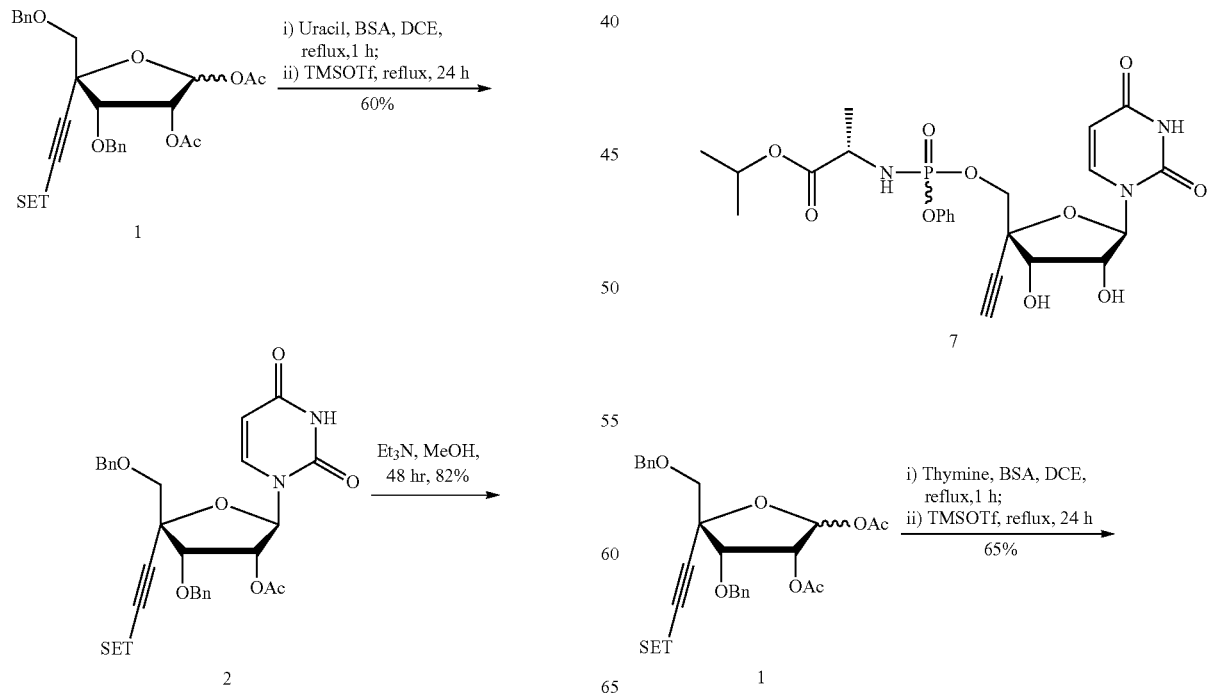
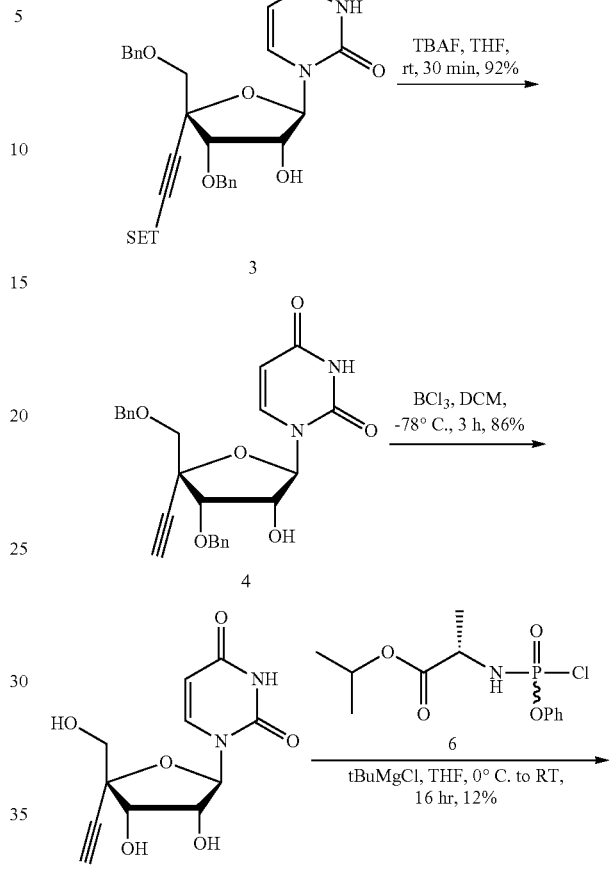

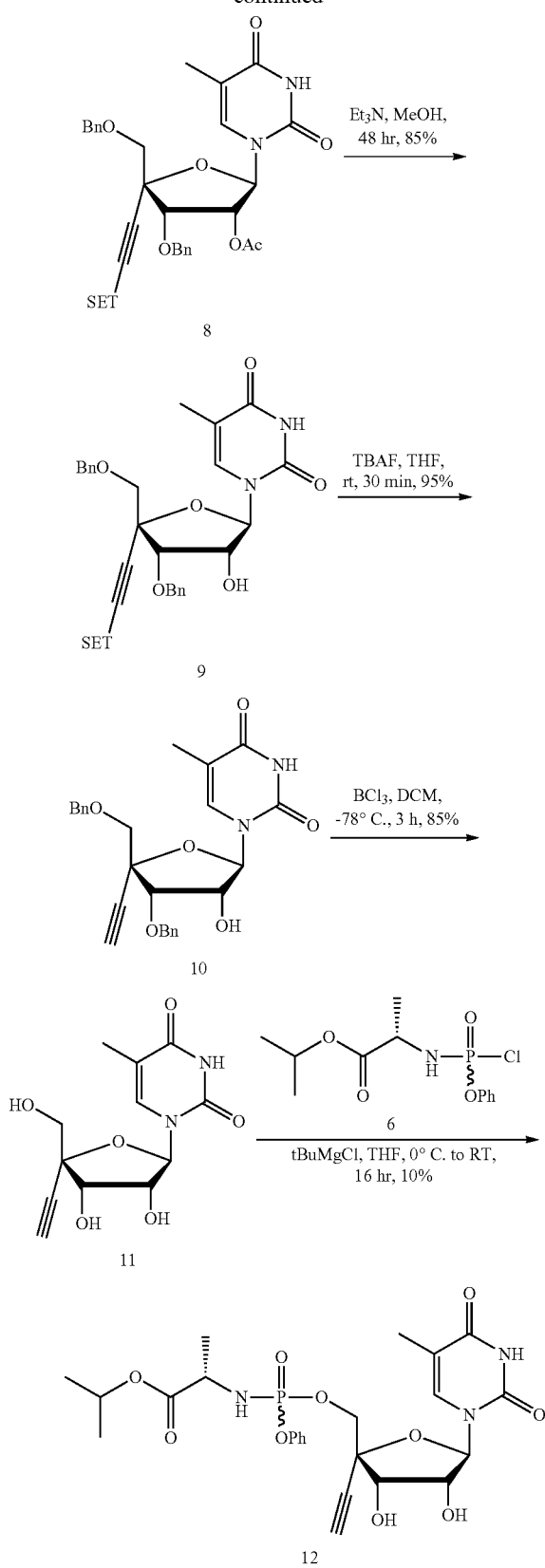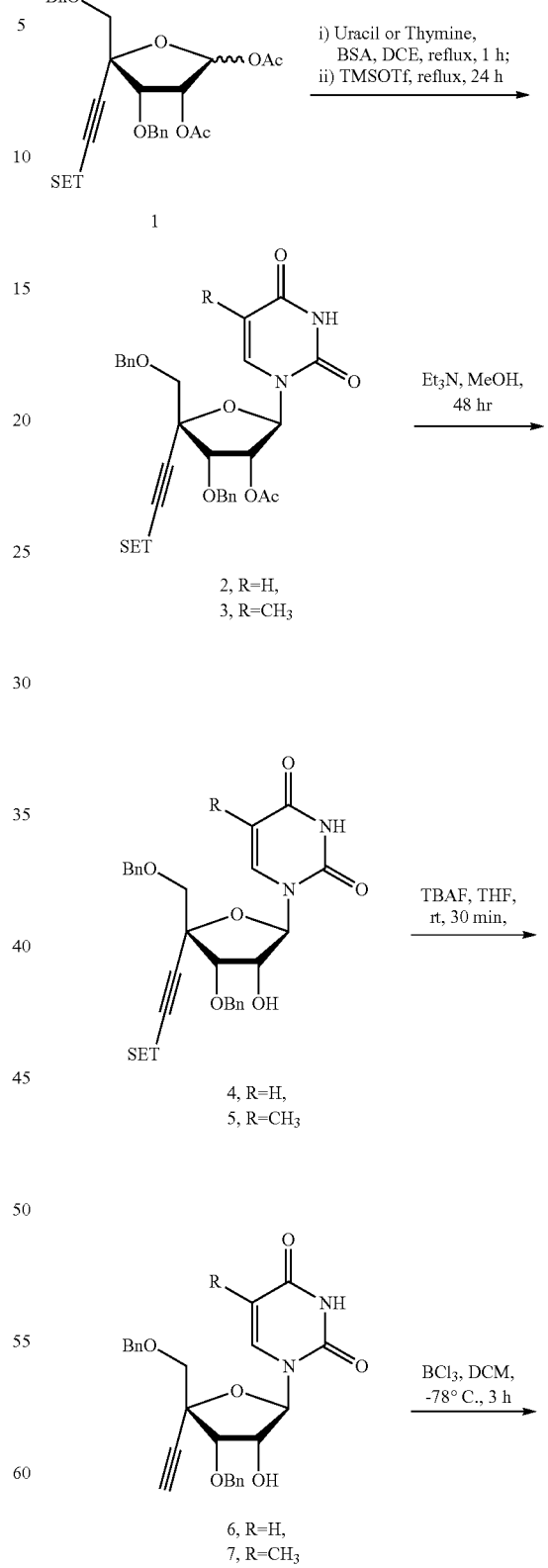
Another general scheme for making these compounds is provided below in Scheme 4:

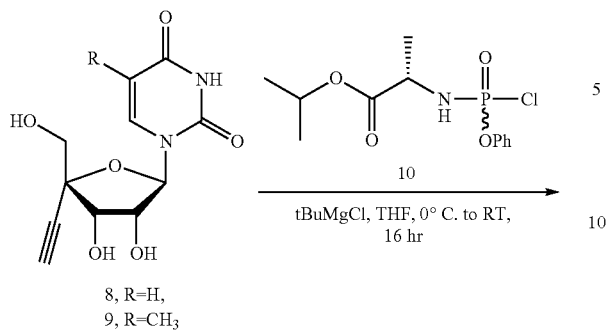

8, R=H,
9, R=CH₃

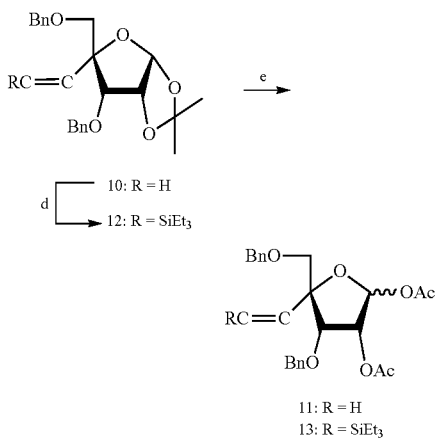

10: R = H
12: R = SiEt₃

11: R = H
13: R = SiEt₃ a Reagents:
(a) (CoCl)₂, DMSO, Et₃N, CH₂Cl₂;
(b) CBr₄, PPh₃, CH₂Cl₂;
(c) n-BuLi, THF;
(d) n-BuLi, THF, then Et₃SiCl;
(e) 1. 70% AcOH, TFA, 2. Ac₂O, pyridine.

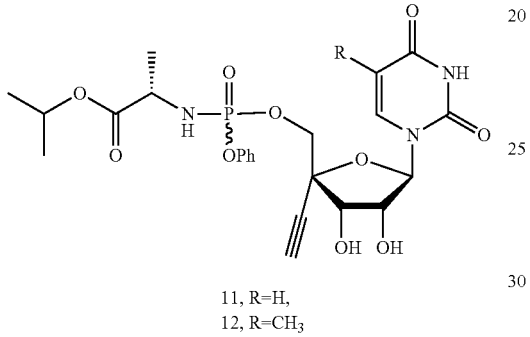

11, R=H,
12, R=CH₃

Additional syntheses of 4'-ethynyl compounds are disclosed, for example, in Ohrui, et al., "Syntheses of 4'-C-Ethynyl-β-D-arabino- and 4'-C-Ethynyl-2-deoxy-β-D-ribopentofuranosylpyrimidines and -purines and Evaluation of Their Anti-HIV Activity," J. Med. Chem. 2000, 43, 4516-4525.

Scheme 6

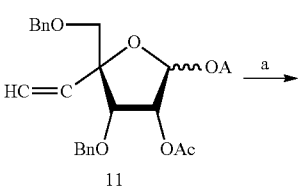

11

Scheme 5

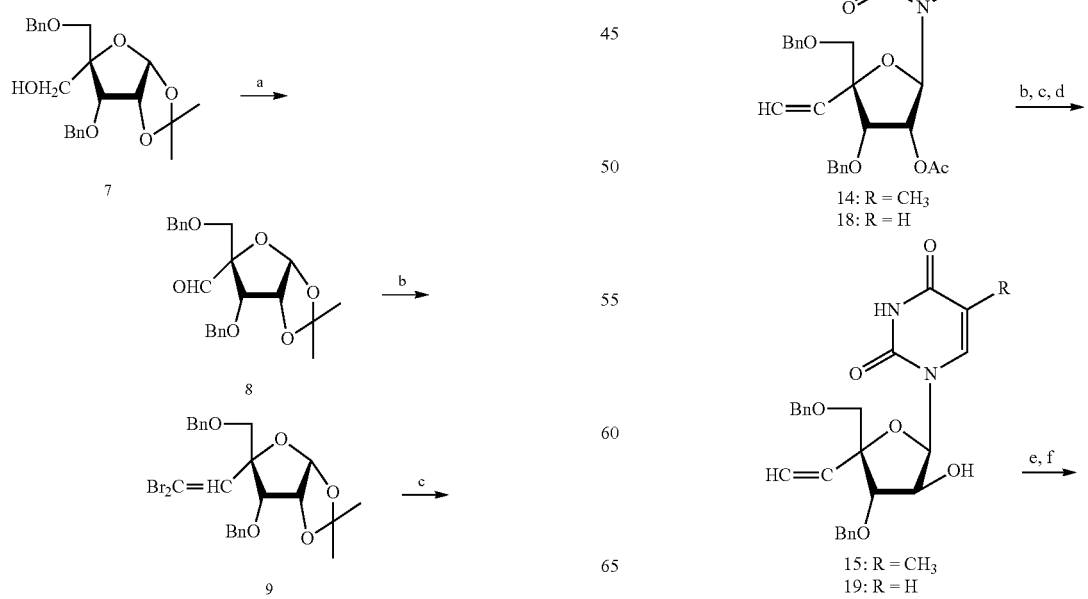

14: R = CH₃
18: R = H

15: R = CH₃
19: R = H

-continued

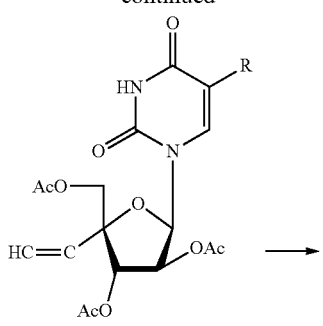

16: R = CH₃
20: R = H

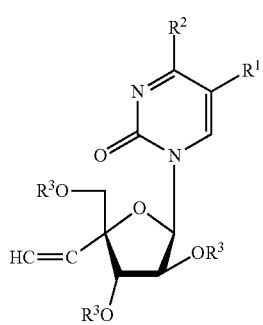

g ⎡ 16: R¹ = CH₃, R² = OH, R³ = Ac
  ⎣→ 17: R¹ = CH₃, R² = OH, R³ = H h ⎡ 20: R¹ = H, R² = OH, R³ = Ac
i ⎣→ 21: R¹ = H, R² = triazolo, R³ = Ac
   → 22: R¹ = H, R² = NH₂, R³ = H ᵃReagents:
(a) silylated base, TMSOTf, 1,2-DCE;
(b) NaOH (aq), MeOH;
(c) MsCl, pyridine;
(d) NaOH (aq), THF;
(e) BBr₃, CH₂Cl₂;
(f) Ac₂O, pyridine;
(g) MeONa, MeOH;
(h) 1,2,4-triazole, Cl₂P(dO)—OC₆H₄Cl, pyridine;
(i) NH₄OH, dioxane.

Scheme 7

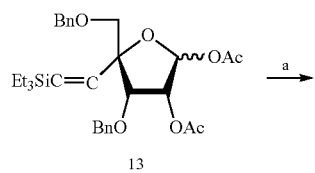

13

-continued

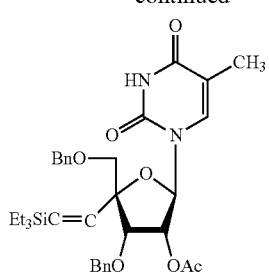

b ⎡ 23: R = Ac
c ⎣→ 24: R = OH
     → 25: R = C(=S)OPh

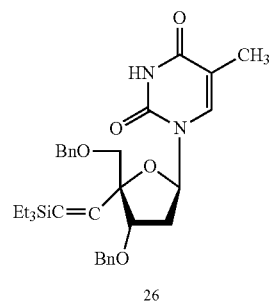

26

ᵃReagents:
(a) silylated thymine, TMSOTf, 1,2-DCE;
(b) Et₃N, MeOH;
(c) ClC(dS)OPh, DMAP, MeCN;
(d) n-Bu₃SnH, AIBN, toluene.

Scheme 8

13 —a→

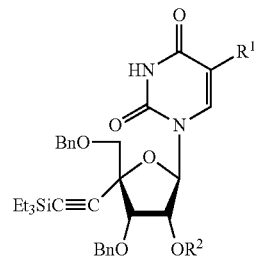

b ⎡ 23: R¹ = CH₃, R² = Ac
  ⎣→ 23: R¹ = CH₃, R² = H b ⎡ 31: R¹ = C₂H₅, R² = Ac
  ⎣→ 32: R¹ = C₂H₅, R² = H b ⎡ 37: R¹ = H, R² = Ac
  ⎣→ 38: R¹ = H, R² = H b ⎡ 43: R¹ = F, R² = Ac
  ⎣→ 44: R¹ = F, R² = H

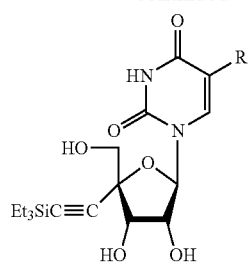

27: R = CH₃
33: R = C₂H₅
39: R = H
45: R = F

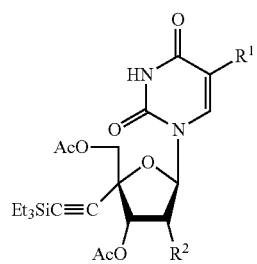

e ⎰ 26: R¹ = CH₃, R² = Br
  ⎱→ 29: R¹ = CH₃, R² = H
e ⎰ 34: R¹ = C₂H₅, R² = Br
  ⎱→ 35: R¹ = C₂H₅, R² = H
e ⎰ 40: R¹ = H, R² = Br
  ⎱→ 41: R¹ = H, R² = H
e ⎰ 46: R¹ = F, R² = Br
  ⎱→ 47: R¹ = F, R² = H

ᵃReagents:
(a) silylated base, TMSOTf, 1,2-DCE;
(b) Et₃N, MeOH;
(c) BCl₃, CH₂Cl₂;
(d) AcBr, MeCN;
(e) n-Bu₃SnH, AIBN, toluene;
(f) NaOH(aq), MeOH.

Scheme 9

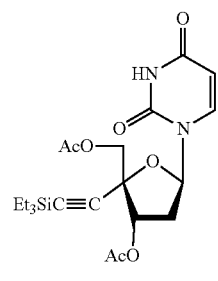

41

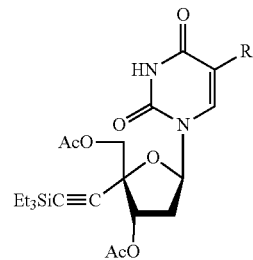

49: R = Cl
51: R = Br
53: R = I

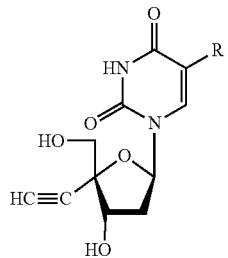

50: R = Cl
52: R = Br
54: R = I

ᵃReagents:
(a) LiCl, CAN, AcOH-MeCN;
(b) LiBr, CAN, MeCN;
(c) I₂, CAN, MeCN;
(d) NaOH(aq), MeOH.

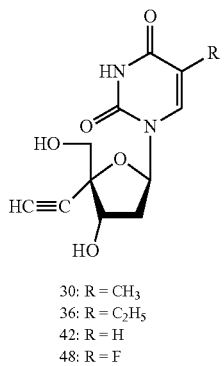

30: R = CH₃
36: R = C₂H₅
42: R = H
48: R = F

Scheme 10

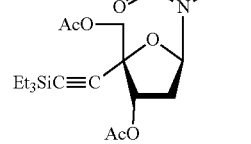

29: R = CH₃
41: R = H
47: R = F
49: R = Cl
51: R = Br
53: R = I

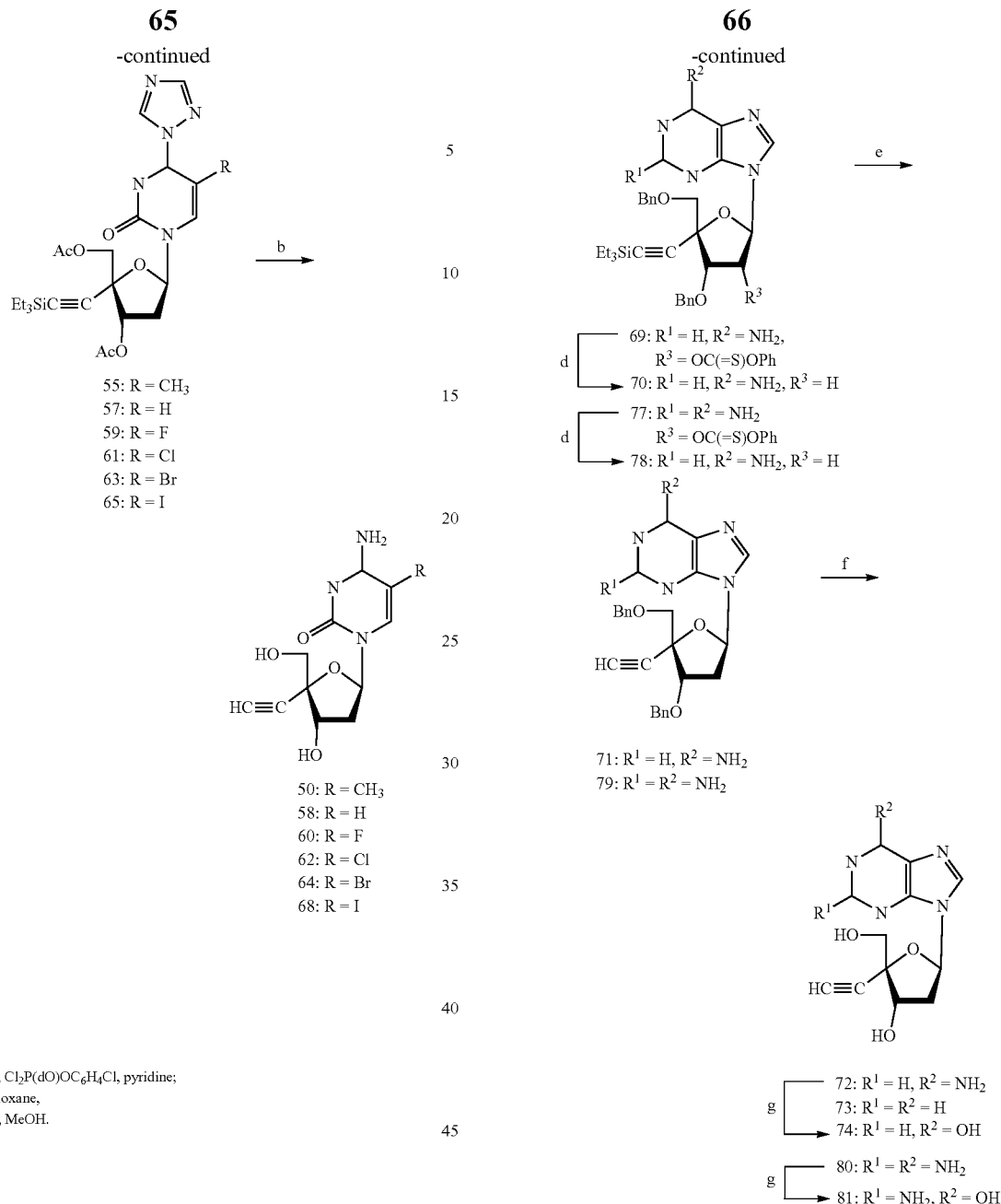

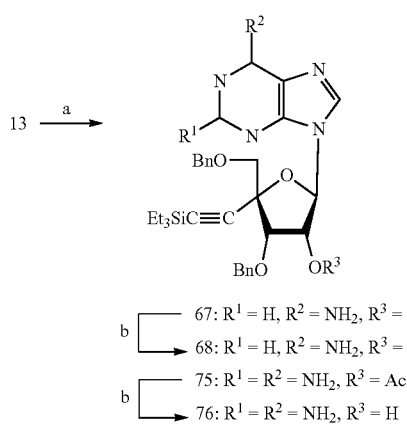

Incorporation of Deuterium:

It is expected that single or multiple replacement of hydrogen with deuterium (carbon-hydrogen bonds to carbon-deuterium bond) at site(s) of metabolism in the sugar portion of a nucleoside antiviral agent will slow down the rate of metabolism. This can provide a relatively longer half-life, and slower clearance from the body. The slow metabolism of a therapeutic nucleoside is expected to add extra advantage to a therapeutic candidate, while other physical or biochemical properties are not affected. Intracellular hydrolysis or deuterium exchanges my result in liberation of deuterium oxide ($D_2O$).

Methods for incorporating deuterium into amino acids, phenol, sugars, and bases, are well known to those of skill in the art. Representative methods are disclosed in U.S. Pat. No. 9,045,521.

A large variety of enzymatic and chemical methods have been developed for deuterium incorporation at both the sugar and nucleoside stages to provide high levels of deuterium incorporation (D/H ratio). The enzymatic method of deuterium exchange generally has low levels of incorporation. Enzymatic incorporation has further complications due to cumbersome isolation techniques which are required for isolation of deuterated mononucleotide blocks. Schmidt et al., Ann. Chem. 1974, 1856; Schmidt et al., Chem. Ber., 1968, 101, 590, describes synthesis of 5',5'-$^2H_2$-adenosine which was prepared from 2',3'-O-isopropylideneadenosine-5'-carboxylic acid or from methyl-2,3-isopropylidene-beta-D-ribofuranosiduronic acid, Dupre, M. and Gaudemer, A., Tetrahedron Lett. 1978, 2783. Kintanar, et al., Am. Chem. Soc. 1998, 110, 6367 reported that diastereoisomeric mixtures of 5'-deuterioadenosine and 5'(R/S)-deuteratedthymidine can be obtained with reduction of the appropriate 5'-aldehydes using sodium borodeuteride or lithium aluminum deuteride (98 atom % $^2H$ incorporation). Berger et al., Nucleoside & Nucleotides 1987, 6, 395 described the conversion of the 5'-aldehyde derivative of 2'deoxyguanosine to 5' or 4'-deuterio-2'-deoxyguanosine by heating the aldehyde in $^2H_2O$/pyridine mixture (1:1) followed by reduction of the aldehyde with $NaBD_4$.

Ajmera et al., Labelled Compd. 1986, 23, 963 described procedures to obtain 4'-deuterium labeled uridine and thymidine (98 atom % $^2H$). Sinhababu, et al., J. Am. Chem. Soc. 1985, 107, 7628) demonstrated deuterium incorporation at the C3' (97 atom % $^2H$) of adenosine during sugar synthesis upon stereoselective reduction of 1,2:5,6-di-O-isopropylidene-β-D-hexofuranos-3-ulose to 1,2:5,6-di-O-isopropylidene-3-deuterio-β-D-ribohexofuranose using sodium borodeuteride and subsequently proceeding further to the nucleoside synthesis. Robins, et al., Org. Chem. 1990, 55, 410 reported synthesis of more than 95% atom $^2H$ incorporation at C3' of adenosine with virtually complete stereoselectivity upon reduction of the 2'-O-tert-butyldimethylsilyl (TBDMS) 3-ketonucleoside by sodium borodeuteride in acetic acid. David, S. and Eustache, J., Carbohyd. Res. 1971, 16, 46 and David, S. and Eustache, J., Carbohyd. Res. 1971, 20, 319 described syntheses of 2'-deoxy-2'(S)-deuterio-uridine and cytidine. The synthesis was carried out by the use of 1-methyl-2-deoxy-2'-(S)-deuterio ribofuranoside.

Radatus, et al., J. Am. Chem. Soc. 1971, 93, 3086 described chemical procedures for synthesizing 2'-monodeuterated (R or S)-2'-deoxycytidines. These structures were synthesized from selective 2-monodeuterated-2-deoxy-D-riboses, which were obtained upon stereospecific reduction of a 2,3-dehydro-hexopyranose with lithium aluminum deuteride and oxidation of the resulting glycal. Wong et al. J. Am. Chem. Soc. 1978, 100, 3548 reported obtaining deoxy-1-deuterio-D-erythro-pentose, 2-deoxy-2(S)-deuterio-D-erythro-pentose and 2-deoxy-1,2(S)-dideuterio-D-erythro-pentose from D-arabinose by a reaction sequence involving the formation and $LiAlD_4$ reduction of ketene dithioacetal derivatives.

Pathak et al. J., Tetrahedron 1986, 42, 5427) reported stereospecific synthesis of all eight 2' or 2'-deuterio-2'-deoxynucleosides by reductive opening of appropriate methyl 2,3-anhydro-beta-D-ribo or beta-D-lyxofuranosides with $LiAlD_4$. Wu et al. J. Tetrahedron 1987, 43, 2355 described the synthesis of all 2',2"-dideuterio-2'-deoxynucleosides, for both deoxy and ribonucleosides, starting with oxidation of C2' of sugar and subsequent reduction with $NaBD_4$ or $LiAlD_4$ followed by deoxygenation by tributyltin deuteride. Roy et al. J. Am. Chem. Soc. 1986, 108, 1675, reported 2',2'-dideuterio-2'-deoxyguanosine and thymidine can be prepared from 2-deoxyribose 5-phosphate using 2-deoxyribose 5-phosphate aldolase enzyme in $^2H_2O$ achieving some 90 atom % deuteration. Similarly, the synthesis of 4',5',5'-$^2H_3$-guanosine can be carried out.

Therefore, it is clear that each position of the sugar residue can be selectively labeled.

A useful alternative method of stereospecific deuteration was developed to synthesize polydeuterated sugars. This method employed exchange of hydrogen with deuterium at the hydroxyl bearing carbon (i.e. methylene and methine protons of hydroxyl bearing carbon) using deuterated Raney nickel catalyst in $^2H_2O$.

Various techniques are available to synthesize fully deuterated deoxy and ribonucleosides. Thus in one method, exchange reaction of deuterated Raney nickel-$^2H_2O$ with sugars, a number of deuterated nucleosides specifically labeled at 2', 3' and 4' positions were prepared. The procedure consisted of deuteration at 2', 3' and 4' positions of methyl beta-D-arabinopyranoside by Raney nickel-$^2H_2O$ exchange reaction followed by reductive elimination of '2-hydroxyl group by tributyltin deuteride to give methyl beta-D-2',2',3',4'-$^2H_4$-2-deoxyribopyranoside, which was converted to methyl beta-D-2',2',3',4'-$^2H_4$-2-deoxyribofuranoside and glycosylated to give various 2',2',3',4'-$^2H_4$-nucleosides (>97 atom % $^2H$ incorporation for H3' & H4'.

The synthesis of deuterated phenols is described, for example, in Hoyer, H. (1950), Synthese des pan-Deutero-o-nitro-phenols. Chem. Ber., 83: 131-136. This chemistry can be adapted to prepare substituted phenols with deuterium labels. Deuterated phenols, and substituted analogs thereof, can be used, for example, to prepare phenoxy groups in phosphoramidate prodrugs.

The synthesis of deuterated amino acids is described, for example, in Matthews et al., Biochimica et Biophysica Acta (BBA)—General Subjects, Volume 497, Issue 1, 29 Mar. 1977, Pages 1-13. These and similar techniques can be used to prepare deuterated amino acids, which can be used to prepare phosphoramidate prodrugs of the nucleosides described herein.

One method for synthesizing a deuterated analog of the compounds described herein involves synthesizing a deuterated ribofuranoside with a 4'-alkynyl substitution; and attaching a nucleobase to the deuterated ribofuranoside to form a deuterated nucleoside. A prodrug, such as a phosphoramidate prodrug, can be formed by modifying the 5' —OH group on the nucleoside. Where a deuterated phenol and/or deuterated amino acid is used, one can prepare a deuterated phosphoramidate prodrug.

Another method involves synthesizing a ribofuranoside with 4'-alkynyl substitution, and attaching a deuterated nucleobase to form a deuterated nucleoside. This method can optionally be performed using a deuterated furanoside to provide additional deuteration. As with the method described above, the nucleoside can be converted into a prodrug form, which prodrug form can optionally include additional deuteration.

A third method involves synthesizing a ribofuranoside with 4'-alkynyl substitution, attaching a nucleobase to form a nucleoside, and converting the nucleoside to a phosphoramidate prodrug using one or both of a deuterated amino acid or phenol analog in the phosphoramidate synthesis.

Accordingly, using the techniques described above, one can provide one or more deuterium atoms in the sugar, base, and/or prodrug portion of the nucleoside compounds described herein.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee, WI) and EMD Chemicals Inc. (Gibbstown, NJ). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, GA). Analytic TLC was performed on Whatman LK6F silica gel plates, and preparative TLC on Whatman PK5F silica gel plates. Column chromatography was carried out on Silica Gel or via reverse-phase high performance liquid chromatography.

Example 1

The techniques shown below in connection with Compounds 1-4 can be used to prepare other compounds described herein which include different bases than 2-Fluoro adenine. That is, the following intermediate can be used to attach different bases, which would then be used in place of Compound 1 in Scheme 1:

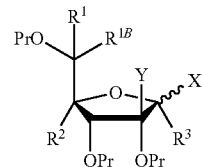

Analogous compounds can be used to prepare the compounds of Formula (B), where a fluorine atom is present at the 2'-position, rather than the O—Pr moiety.

Compound 7 is a common intermediate to a number of compounds described herein. Starting from Compounds 5, 6, or 7, a variety of different prodrugs can be attached to the 5'-OH position. Further, analogs of Compounds 1, 2, 4, 5, or 6 can be prepared, with different functionality at the 1', 3', 4', and 5'-positions, and used as intermediates to prepare additional compounds.

EXPERIMENTAL

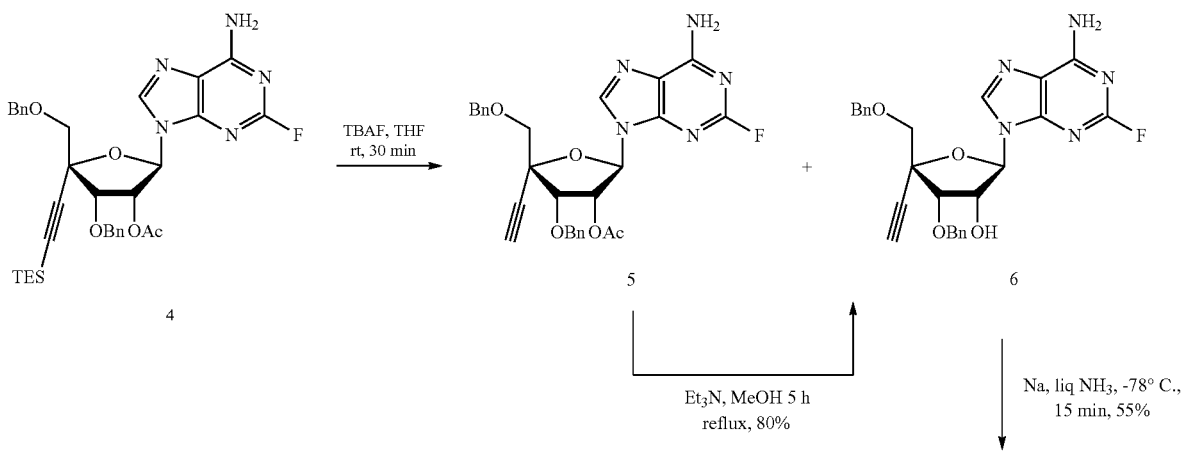

Scheme 12. Synthesis of 4'-Ethynyl-2-Fluoro-Adenosine (7)

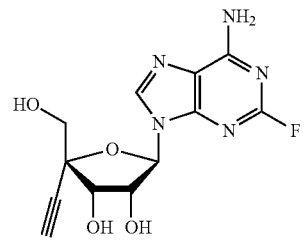

7

(2R,3R,4S,5R)-2-(6-amino-2-fluoro-9H-purin-9-yl)-4-(benzyloxy)-5-((benzyloxy)methyl)-5-(((triethylsilyl)ethynyl)tetrahydrofuran-3-yl acetate (4) was synthesized according to procedures reported in *Org. Lett.* 2015, 17, 828-831.

(2R,3R,4S,5R)-2-(6-amino-2-fluoro-9H-purin-9-yl)-4-(benzyloxy)-5-((benzyloxy)methyl)-5-ethynyltetrahydrofuran-3-yl acetate (5) and (2R,3R,4S,5R)-2-(6-amino-2-fluoro-9H-purin-9-yl)-4-(benzyloxy)-5-((benzyloxy)methyl)-5-ethynyltetrahydrofuran-3-ol (6)

To a stirred solution of compound 4 (0.490 g, 0.76 mmol) in THF (2 mL) was added dropwise a solution of TBAF (1M in THF, 1.51 mL, 1.51 mmol) at 0° C. The reaction is stirred at 0° C. for 30 min. The reaction was quenched with few drops of methanol. The reaction mixture was concentrated and the residue was purified by flash chromatography (dichloromethane-methanol) to obtain compound 5 (0.184 g, 45%) and compound 6 (0.117 g, 31%) as white solids.

Compound 5: $^1$H NMR (400 MHz, Chloroform-d) δ 7.92 (s, 1H), 7.23-7.41 (m, 10H), 6.25 (d, J=4.2 Hz, 1H), 5.78 (bs, 2H), 5.70 (dd, J=5.8, 4.2 Hz, 1H), 4.64-4.75 (m, 3H), 4.51 (d, J=11.9 Hz, 1H), 4.44 (d, J=11.9 Hz, 1H), 3.78 (d, J=10.8 Hz, 1H), 3.62 (d, J=10.8 Hz, 1H), 2.72 (s, 1H), 2.12 (s, 3H). $^{19}$F NMR (377 MHz, Chloroform-d) δ -51.54. LR-MS calculated for $C_{28}H_{26}FN_5O_5$ 531.19, found 531.00.

Compound 6: $^1$H NMR (400 MHz, Chloroform-d) δ 7.88 (s, 1H), 7.24-7.42 (m, 10H), 6.04 (d, J=4.6 Hz, 1H), 5.76 (bs, 2H), 4.92 (d, J=11.4 Hz, 1H), 4.67-4.73 (m, 2H), 4.48-4.58 (m, 3H), 3.80 (d, J=10.6 Hz, 1H), 3.69 (d, J=10.6 Hz, 1H), 3.20 (d, J=7.2 Hz, 1H), 2.74 (s, 1H). $^{19}$F NMR (377 MHz, Chloroform-d) δ -51.78. LR-MS calculated for $C_{26}H_{24}FN_5O_4$ 489.18, found 490.5.

(2R,3S,4R,5R)-5-(6-amino-2-fluoro-9H-purin-9-yl)-2-ethynyl-2-(hydroxymethyl)tetrahydrofuran-3,4-diol or [4'-Ethynyl-2-Fluoro-Adenosine] (7)

Method A: Compound 6 (0.117 g, 0.239 mmol) was dissolved in 1 mL of dry THF and then cooled to -78° C. Ammonia gas was condensed in the same flask to collect 5-7 ml of liq. NH$_3$. Small pieces of Na metal (26 mg, 1.196 mmol) were added portion wise at -78° C. After 15 min at this temperature, the dry ice bath was removed and the reaction was quenched slowly with solid NH$_4$Cl (100 mg) at 0° C. The reaction mixture was warmed to room temperature and stirred for an additional 1 h to remove NH$_3$. The residue was diluted with methanol and filtered. The filtrate was concentrated and the residue was purified by flash column chromatography (dichloromethane-methanol) to obtain compound 7 (40 mg, 55% yield) as a white solid. $^1$H NMR (400 MHz, DMSO-d$_6$) δ 8.34 (s, 1H), 7.96 (bs, 2H), 5.86 (d, J=6.7 Hz, 1H, H1'), 5.49 (m, 3H, 3'-OH, 2'-OH, 3'-OH), 4.68 (q, J=6.6 Hz, 1H), 4.21 (t, J=5.7 Hz, 1H), 3.67 (dd, J=11.9, 5.3 Hz, 1H, 5'), 3.60-3.55 (m, 1H, 5''), 3.53 (s, 1H, ethynyl-H). $^{19}$F NMR (377 MHz, DMSO-d$_6$) δ -53.33. $^{13}$C NMR (101 MHz, DMSO-d$_6$) δ 159.01 (d, J=204.3 Hz), 158.14 (d, J=21.3 Hz), 151.10 (d, J=20.2 Hz), 140.49, 117.91 (d, J=4.0 Hz). 87.56, 85.01, 81.86, 79.42, 73.25, 71.75, 66.21. LR-MS—calculated for $C_{12}H_{12}FN_5O_4$, 309.08 found 310.4.

Method B: A solution of compound 5 (0.184 g, 0.346 mmol) in methanol (5 mL) containing 5% triethylamine was refluxed for 5 hours. Solvents were evaporated and the crude residue (0.135 g, 80% yield) used as such in the benzyl deprotection step (Method A) to obtain compound 7.

Example 2

Additional synthetic examples are provided below.

Synthesis of 4'-C-Ethynyluridine

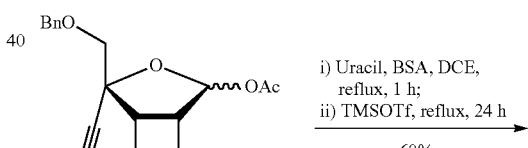

1

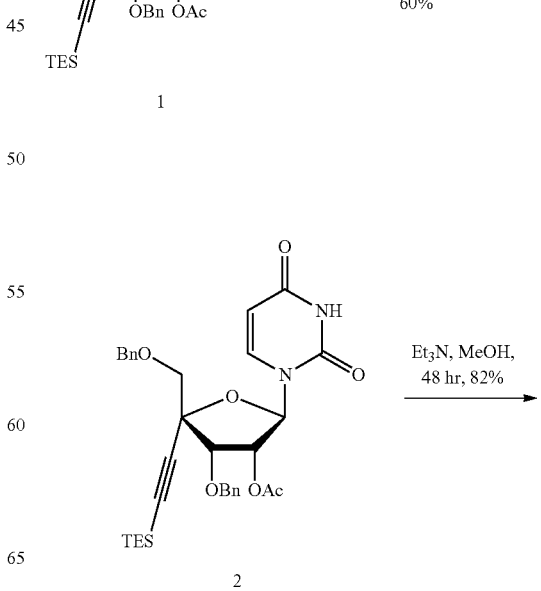

2

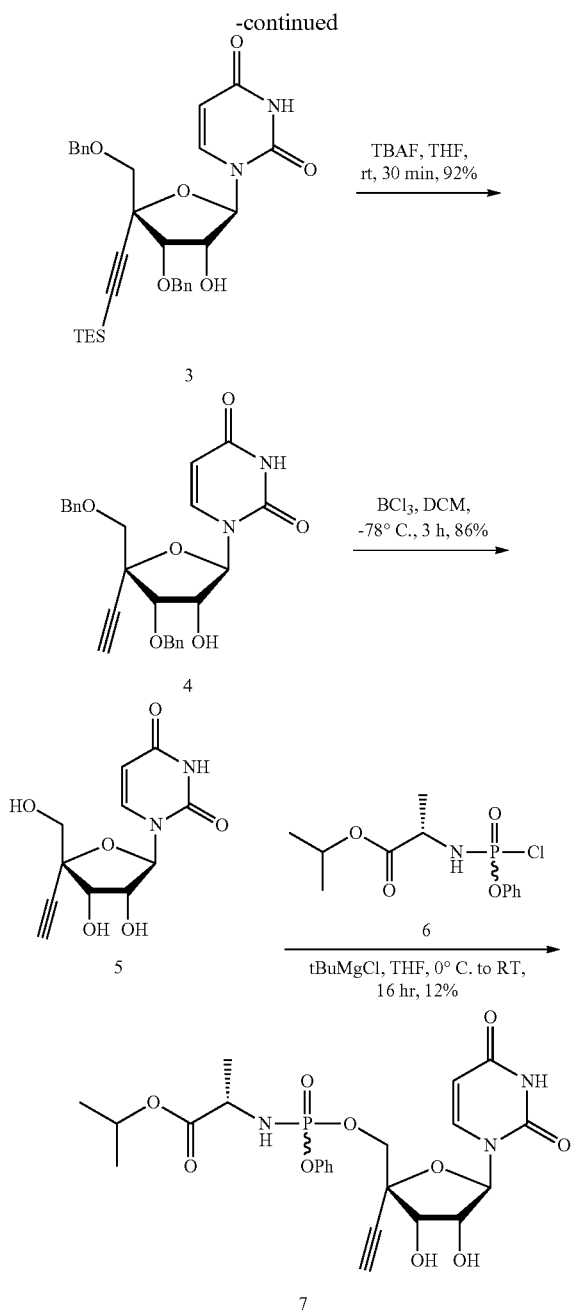

saturated NaHCO$_3$ (15 ml) and brine (10 ml), and dried over MgSO4. The solvent was removed and the residue was purified by flash column chromatography (hexane:ethyl acetate) to obtain compound 2 (0.460 g, 60% yield) as a white solid.

$^1$H NMR (400 MHz, Methanol-d$_4$) δ 7.64 (d, J=8.1 Hz, 1H), 7.27-7.17 (m, 10H), 6.03 (d, J=4.3 Hz, 1H), 5.49-5.10 (m, 2H), 4.58-4.32 (m, 5H), 3.71 (d, J=10.7 Hz, 1H), 3.59 (d, J=10.7 Hz, 1H), 1.93 (s, 3H), 0.89 (t, J=7.9 Hz, 9H), 0.50 (q, J=7.8 Hz, 6H).

1-((2R,3R,4S,5R)-4-(benzyloxy)-5-((benzyloxy)methyl)-3-hydroxy-5-((triethylsilyl)ethynyl)tetrahydrofuran-2-yl)pyrimidine-2,4(1H,3H)-dione (3)

A solution of 2 (0.611 g, 1.01 mmol) in methanol containing 10% trimethylamine (40 ml) was stirred for 48 h at room temperature. The solvents were evaporated and the residue was purified by flash column chromatography (hexane:ethyl acetate) to obtain compound 3 (0.467 g, 82% yield) as a white solid.

$^1$H NMR (400 MHz, Methanol-d$_4$) δ 7.72 (d, J=8.1 Hz, 1H), 7.48-7.30 (m, 10H), 6.13 (d, J=6.5 Hz, 1H), 5.41 (d, J=8.1 Hz, 1H), 4.86 (m, 2H), 4.57 (d, J=3.6 Hz, 2H), 4.32 (dd, J=6.5, 5.6 Hz, 1H), 4.16 (d, J=5.6 Hz, 1H), 3.80 (d, J=10.3 Hz, 1H), 3.73 (d, J=10.3 Hz, 1H), 1.01 (t, J=7.9 Hz, 9H), 0.65-0.59 (m, 6H). LCMS Cacld for C$_{31}$H$_{39}$N$_2$O$_6$Si (M+H) 563.7; found 563.6

1-((2R,3R,4S,5R)-4-(benzyloxy)-5-((benzyloxy)methyl)-5-ethynyl-3-hydroxytetrahydrofuran-2-yl)pyrimidine-2,4(1H,3H)-dione (4)

To a stirred solution of compound 3 (0.467 g, 0.83 mmol) in THF (10 mL) was added dropwise a solution of TBAF (1M in THF, 1.17 mL, 1.17 mmol) at 0° C. The reaction is stirred at 0° C. for 30 min. The reaction was quenched with few drops of methanol. The reaction mixture was concentrated and the residue was purified by flash chromatography (dichloromethane-methanol) to obtain compound 4 (0.342 g, 92%) as a white solid.

$^1$H NMR (400 MHz, Methanol-d$_4$) δ 7.72 (d, J=8.1 Hz, 1H), 7.48-7.29 (m, 10H), 6.08 (d, J=5.5 Hz, 1H), 5.35 (d, J=8.1 Hz, 1H), 4.81 (d, J=2.2 Hz, 2H), 4.52 (s, 2H), 4.31 (t, J=5.6 Hz, 1H), 4.18 (d, J=5.7 Hz, 1H), 3.81 (d, J=10.5 Hz, 1H), 3.71 (d, J=10.4 Hz, 1H), 3.18 (s, 1H).

1-((2R,3R,4S,5R)-5-ethynyl-3,4-dihydroxy-5-(hydroxymethyl)tetrahydrofuran-2-yl)pyrimidine-2,4(1H,3H)-dione (5) or 4'-C-Ethynyluridine To a solution of compound 4 (0.078 g, 0.17 mmol) in dichloromethane (3 ml) was added boron trichloride (1M in dichloromethane solution, 1.74 ml, 1.74 mmol) at −78° C. under inert atmosphere and mixture was stirred at same temperature for 3 h. Reaction was quenched with 2:1 mixture of methanol:pyridine (1.5 ml) and was stirred for 10 min at −78° C. Solvents were evaporated and purified by column chromatography. The product eluted along with some pyridinium salt. Another column purification leads to the pure compound 5 (40 mg, 86%).

$^1$H NMR (400 MHz, Methanol-d$_4$) δ 7.85 (d, J=8.1 Hz, 1H), 5.99 (d, J=5.1 Hz, 1H), 5.68 (d, J=8.1 Hz, 1H), 4.49-4.04 (m, 2H), 3.75 (d, J=12.1 Hz, 1H), 3.69 (d, J=12.0 Hz, 1H), 3.03 (s, 1H).

(2R,3R,4S,5R)-4-(benzyloxy)-5-((benzyloxy)methyl)-2-(2,4-dioxo-3,4-dihydropyrimidin-1(2H)-yl)-5-((triethylsilyl)ethynyl)tetrahydrofuran-3-yl acetate (2)

A mixture of 1 (0.703 g, 1.27 mmol), uracil (0.356 g, 3.17 mmol) and bis(trimethylsilyl)acetamide (2.17 ml, 8.90 mmol) in dichloroethane (5 ml) was stirred under reflux for 1 h and then cooled to 0° C. To this mixture, trimethylsilyl trifluoromethanesulfonate (0.46 ml, 2.54 mmol) was added and the mixture was stirred under reflux for 24 h. Reaction mixture was cooled to room temperature, quenched with an ice-cold saturated solution of NaHCO$_3$ (15 ml) and filtered through sintered funnel. The filtrate was extracted with chloroform (3×15 ml). The organic layer was washed with

Isopropyl ((((2R,3S,4R,5R)-5-(2,4-dioxo-3,4-dihydropyrimidin-1(2H)-yl)-2-ethynyl-3,4-dihydroxytetrahydrofuran-2-yl)methoxy)(phenoxy)phosphoryl)-L-alaninate (7)

The nucleoside 5 (30 mg, 0.11 mmol) was dried at 50° C. under high vacuum for 4 h before adding anhydrous THF (0.5 mL) at 25° C. The mixture was cooled to 0° C. and tert-butylmagnesium chloride (0.28 mL, 0.28 mmol, 1M in THF) was introduced dropwise. After stirring at 0° C. for 30 min, (2S)-isopropyl 2-((chloro(phenoxy)phosphoryl)amino)propanoate, 6 (85 mg, 0.28 mmol) in 0.28 mL of anhydrous THF was added slowly. The reaction mixture was allowed to attain rt and stirred for 16 h. The reaction was quenched with 1M HCl (0.1 mL). The solvent was removed under reduced pressure and the residue was purified by flash chromatography using 0-10% MeOH/CH$_2$Cl$_2$ to afford 7 (7 mg, 12%) as a diastereomeric (R$_p$/S$_p$) mixture.

$^1$H NMR (400 MHz, Methanol-d$_4$) δ 7.61 (2d merged, each J=8.1 Hz, 1H), 7.41-7.37 (m, 2H), 7.33-7.21 (m, 3H), 6.04-6.0 (m, 1H), 5.68 (2d merged, each J=8.1 Hz, 1H), 5.03-4.94 (m, 1H), 4.37-4.20 (m, 4H), 3.99-3.89 (m, 1H), 3.23 (2s merged, 1H), 1.37-1.23 (m, 9H). $^{31}$P NMR (162 MHz, MeOD) δ 3.51, 3.29. LCMS Cacld for C$_{23}$H$_{29}$N$_3$O$_{10}$P (M+H) 538.4; found 538.4

Synthesis of 4'-C-Ethynyl-β-D-ribo-pentafuranosyl-thymine

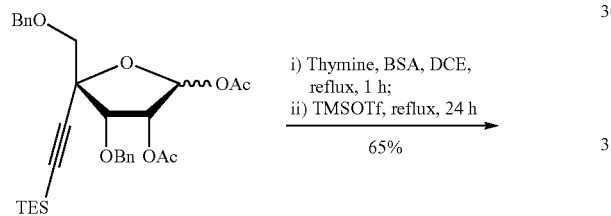

1

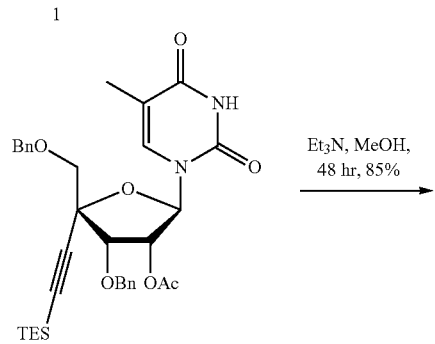

8

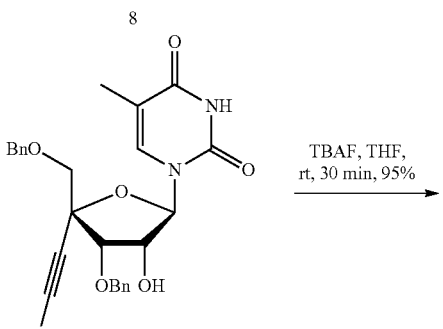

9

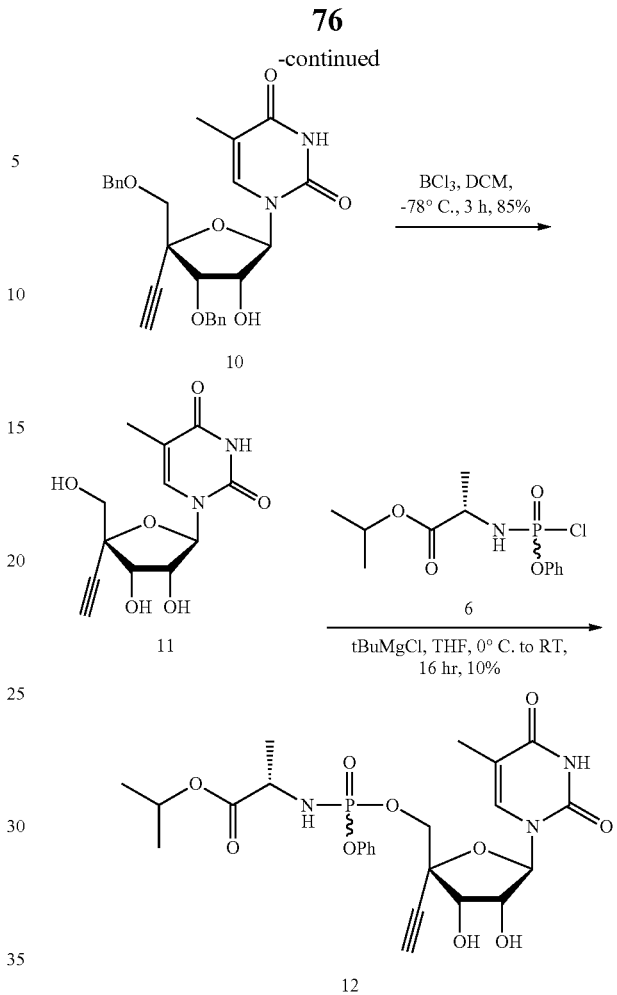

(2R,3R,4S,5R)-4-(benzyloxy)-5-((benzyloxy)methyl)-2-(5-methyl-2,4-dioxo-3,4-dihydropyrimidin-1(2H)-yl)-5-((triethylsilyl)ethynyl)tetrahydrofuran-3-yl acetate (8)

A mixture of 1 (0.574 g, 1.04 mmol), thymine (0.327 g, 2.59 mmol) and bis(trimethylsilyl)acetamide (1.77 ml, 7.26 mmol) in 1,2-dichloroethane (5 ml) was stirred under reflux for 1 h and then cooled to 0° C. To this mixture, trimethylsilyl trifluoromethanesulfonate (0.39 ml, 2.18 mmol) was added and the mixture was stirred under reflux for 24 h. Reaction mixture was cooled to room temperature, quenched with ice-cold saturated solution of NaHCO$_3$ (15 ml) and filtered through sintered funnel. The filtrate was extracted with chloroform (3×15 ml). The organic layer was washed with saturated NaHCO$_3$ (15 ml) and brine (10 ml), and dried over MgSO4. The solvent was removed and the residue was purified by flash column chromatography (hexane:ethyl acetate) to obtain compound 8 (0.416 g, 65% yield) as a white solid.

$^1$H NMR (400 MHz, Chloroform-d) δ 8.81 (s, 1H), 7.37-7.28 (m, 11H), 6.34 (d, J=5.3 Hz, 1H), 5.26 (dd, J=6.0, 5.4 Hz, 1H), 4.74 (d, J=11.7 Hz, 1H), 4.58 (d, J=11.7 Hz, 1H), 4.54 (d, J=1.4 Hz, 2H), 4.39 (d, J=6.0 Hz, 1H), 3.87 (d, J=10.6 Hz, 1H), 3.67 (d, J=10.6 Hz, 1H), 2.05 (s, 3H), 1.54 (s, 3H), 0.97 (t, J=7.9 Hz, 9H), 0.62-0.56 (m, 6H).

1-((2R,3R,4S,5R)-4-(benzyloxy)-5-((benzyloxy) methyl)-3-hydroxy-5-((triethylsilyl)ethynyl)tetrahydrofuran-2-yl)-5-methylpyrimidine-2,4(1H,3H)-dione (9)

A solution of 8 (0.404 g, 0.65 mmol) in methanol containing 10% trimethylamine (25 ml) was stirred for 40 h at room temperature. The solvents were evaporated and the residue was purified by flash column chromatography (hexane:ethyl acetate) to obtain compound 9 (0.319 g, 85% yield) as a white solid.

$^1$H NMR (400 MHz, Chloroform-d) δ 8.89 (s, 1H), 7.40-7.27 (m, 11H), 6.12 (d, J=5.9 Hz, 1H), 4.98 (d, J=11.4 Hz, 1H), 4.67 (d, J=11.4 Hz, 1H), 4.58 (s, 2H), 4.33-4.27 (m, 1H), 4.20 (d, J=5.9 Hz, 1H), 3.87 (d, J=10.5 Hz, 1H), 3.73 (d, J=10.5 Hz, 1H), 3.12 (d, J=9.3 Hz, 1H), 1.57 (s, 3H), 0.96 (t, J=7.9 Hz, 9H), 0.62-0.56 (m, 6H).

1-((2R,3R,4S,5R)-4-(benzyloxy)-5-((benzyloxy) methyl)-5-ethynyl-3-hydroxytetrahydrofuran-2-yl)-5-methylpyrimidine-2,4(1H,3H)-dione (10)

To a stirred solution of compound 9 (0.310 g, 0.54 mmol) in THF (10 mL) was added dropwise a solution of TBAF (1M in THF, 1.07 mL, 1.07 mmol) at 0° C. The reaction is stirred at 0° C. for 30 min. The reaction was quenched with few drops of methanol. The reaction mixture was concentrated and the residue was purified by flash chromatography (dichloromethane-methanol) to obtain compound 10 (0.238 g, 95%) as white solid.

$^1$H NMR (400 MHz, Chloroform-d) δ 9.18 (bs, 1H), 7.42-7.25 (m, 11H), 6.08 (d, J=5.3 Hz, 1H), 4.88 (d, J=11.5 Hz, 1H), 4.70 (d, J=11.5 Hz, 1H), 4.55 (s, 2H), 4.33-4.28 (m, 1H), 4.23 (d, J=5.9 Hz, 1H), 3.85 (d, J=10.5 Hz, 1H), 3.69 (d, J=10.5 Hz, 1H), 3.43 (d, J=8.2 Hz, 1H), 2.70 (s, 1H), 1.57 (s, 3H).

1-((2R,3R,4S,5R)-5-ethynyl-3,4-dihydroxy-5-(hydroxymethyl)tetrahydrofuran-2-yl)-5-methylpyrimidine-2,4(1H,3H)-dione (11)

To a solution of compound 10 (0.064 g, 0.14 mmol) in dichloromethane (3 ml) was added boron trichloride (1M in dichloromethane, 1.38 ml, 1.38 mmol) at −78° C. under inert atmosphere. The mixture was stirred at this temperature for 3 h. Reaction was quenched with a 2:1 mixture of methanol:pyridine (1.5 ml) and was stirred for 10 min at −78° C. Solvents were evaporated and the residue purified by column chromatography. To give 11 (33 mg, 85

$^1$H NMR (400 MHz, Methanol-d$_4$) δ 7.61 (d, J=1.2 Hz, 1H), 5.93 (d, J=4.9 Hz, 1H), 4.22-4.17 (m, 2H), 3.71 (d, J=12.1 Hz, 1H), 3.64 (d, J=12.1 Hz, 1H), 2.98 (s, 1H), 1.78 (d, J=1.2 Hz, 3H).

Isopropyl ((((2R,3S,4R,5R)-2-ethynyl-3,4-dihydroxy-5-(5-methyl-2,4-dioxo-3,4-dihydropyrimidin-1(2H)-yl)tetrahydrofuran-2-yl)methoxy)(phenoxy)phosphoryl)-L-alaninate (12)

Nucleoside 11 (50 mg, 0.18 mmol) was dried at 50° C. under high vacuum for 4 h before addition of anhydrous THF (0.5 mL) at 25° C. The mixture was cooled to 0° C. and tert-butylmagnesium chloride (0.44 mL, 0.44 mmol, 1M in THF) was introduced dropwise. After stirring at 0° C. for 30 min, (2S)-isopropyl 2-((chloro(phenoxy)phosphoryl)amino) propanoate, 6 (135 mg, 0.44 mmol) in 0.44 mL of anhydrous THF was added slowly to the solution. The reaction mixture was warmed up to rt and stirred for 16 h. The reaction was quenched with 1M HCl (0.1 mL). The solvent was removed under reduced pressure and the residue was purified by flash chromatography using 0-10% MeOH/CH$_2$Cl$_2$ to afford 12 (10 mg, 10%) as a diastereomeric (R$_p$/S$_p$) mixture.

$^1$H NMR (400 MHz, Methanol-d$_4$) δ 7.49-7.47 (m, 1H), 7.40-7.36 (m, 2H), 7.29-7.20 (m, 3H), 6.06-6.03 (m, 1H), 5.04-4.94 (m, 1H), 4.37-4.25 (m, 4H), 3.94-3.89 (m, 1H), 3.22 (2s merged, 1H), 1.84 (2s merged, 3H), 1.38-1.17 (m, 9H). $^{31}$P NMR (162 MHz, Methanol-d$_4$) δ 3.47, 3.29.

Scheme 13. Reagents and Conditions: (i) AlMe$_3$, DCM, reflux, overnight, 64% (ii) PIFA, DCM, TFA, 0° C. to rt, 12 h, 55%.

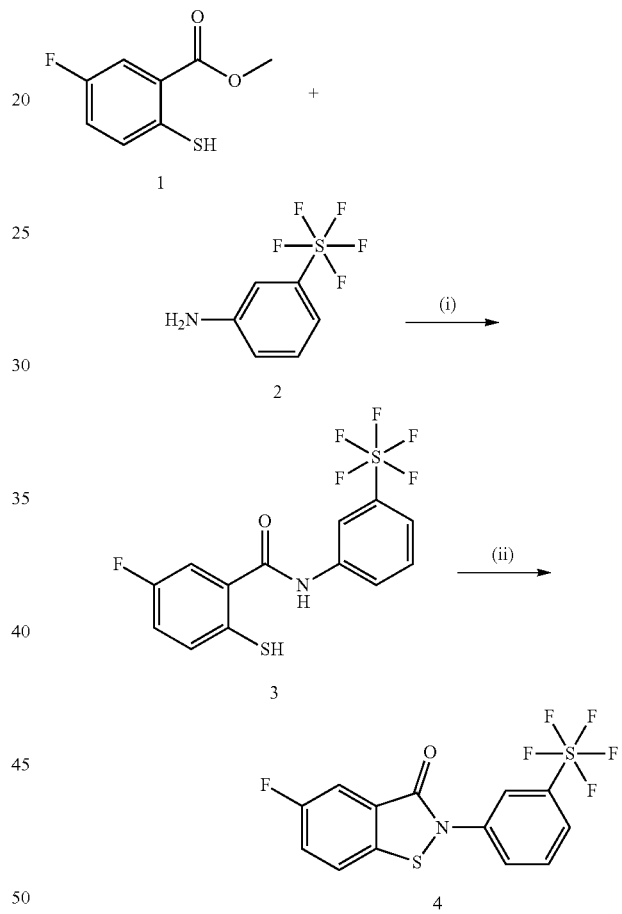

5-Fluoro-N-(3-pentafluorothiophenyl)-2-mercaptobenzamide-3

To a solution of 3-(Pentafluorothio)aniline (142 mg, 0.64 mmol) in dichloromethane (2 mL) was added dropwise a solution of trimethylaluminum in toluene (2M, 0.4 mL, 0.8 mmol) at 0° C. The reaction mixture was stirred at room temperature for 45 min. Methyl 5-fluoro-2-sulfanylbenzoate (100 mg, 0.53 mmol) in dichloromethane (1 mL) was added and the reaction mixture refluxed overnight. The reaction mixture was cooled to room temperature and carefully quenched with 5% aq HCl solution (5 mL). The solid material was filtered through a celite plug. The filtrate was extracted with dichlomethane (2×20 mL), combined organic layers were washed with saturated NaHCO$_3$, water, brine and then dried over Na$_2$SO$_4$, filtered and concentrated under reduced pressure. The crude residue was purified by silica gel chromatography using 0-50% ethyl acetate in hexane to give intermediate 3 (129 mg, 64%) as a white solid. $^1$H-NMR (400 MHz, CD3OD) δ 8.27 (s, 1H), 7.83 (m, 2H), 7.61 (m, 2H), 7.46 (dd, J=8.8, 2.2 Hz, 1H), 7.18 (m, 1H) $^{13}$C NMR (101 MHz, CD3OD) δ 166.1, 163.0, 160.5, 153.8, 153.6, 138.8, 138.0, 137.9, 132.4, 132.3, 131.5, 129.0, 123.1, 121.5, 121.4, 118.2, 117.9, 117.5, 117.4, 78.2, 77.8, 77.5 $^{19}$F NMR (376 MHz, CD3OD) δ −115.2 (m) LCMS Cacld for C$_{13}$H$_9$F$_6$NOS$_2$ (M+H) 374.3; found 374.3

5-Fluoro-2-(3-pentafluorothiophenyl)benzo[d]isothi-azol-3(2H)-one-4

To a solution of compound 3 (113 mg, 0.3 mmol) in dichloromethane (3 mL) was added TFA (46 µL, 0.6 mmol) at 0° C. A solution of bis(trifluoroacetoxy)iodo)benzene (PIFA) (130 mg, 0.3 mmol) in dichloromethane (2 mL) was slowly added to the above reaction mixture over 10 min. After being stirred at room temperature for 12 h, the reaction mixture was concentrated to dryness and the crude residue was purified by silica gel chromatography using 0-2% methanol in dichloromethane to give compound 4 (62 mg, 55%) as a white solid. $^1$H-NMR (400 MHz, DMSO-d6) δ 8.15 (t, J=4.4 Hz, 1H), 7.94 (m, 1H), 7.83 (d, J=8.4 Hz, 2H), 7.75 (m, 3H) $^{13}$C NMR (101 MHz, DMSO-d6) δ 163.3, 162.5, 160.1, 153.6, 153.4, 153.3, 138.1, 136.3, 131.2, 128.4, 126.1, 125.9, 125.0, 124.9, 124.6, 122.1, 122.0, 121.8, 112.5, 112.2, 79.7, 79.4, 79.1 $^{19}$F NMR (376 MHz, DMSO-d6) δ −116.1 (m). LCMS Cacld for C$_{13}$H$_7$F$_6$NOS$_2$ (M+H) 372.3; found 372.3

Example 3

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. Antimicrob. Agents Chemother. 1990, 34, 1061-67). Cycloheximide was included as positive cytotoxic control, and untreated cells exposed to solvent were included as negative controls. The cytotoxicity IC$_{50}$ was obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11). The results are shown in Tables 8, 8A, and 8B below:

TABLE 8

| | Cytotoxicity (IC$_{50}$, µM) | | | |
|---|---|---|---|---|
| Structure | Macrophages | PBM | CEM | Vero |
| [structure 1] | 2.4 | 1.1 | 6.8 | ≥100 |
| [structure 2] | 0.7 | 3.2 | 52.0 | >100 |
| [structure 3] | >10 | >100 | | |

TABLE 8-continued
| Structure | Cytotoxicity (IC$_{50}$, μM) | | | |
|---|---|---|---|---|
| | Macrophages | PBM | CEM | Vero |
|  | >10 | >100 | | |
|  | >10 | >100 | | |
TABLE 8A
| Structure | Cytotoxicity: MTT IC$_{50}$ (μM) | | | | | | |
|---|---|---|---|---|---|---|---|
| | PBM | CEM | Vero | Huh7 | Bone Marrow (GM Lineage) | Bone Marrow (Erythroid Lineage) | Macrophages |
| 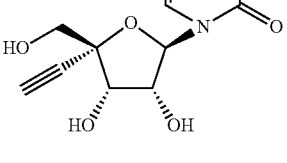 | >100 | >100 | >100 | >100 | >100 (0) | >100 (18) | >100 (28.6) |
| 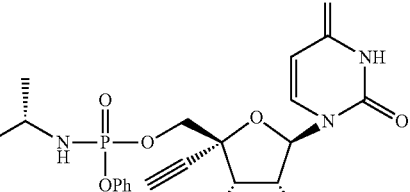 | >100 | >100 | >100 | >100 | >100 (10) | >100 (6) | >100 (9.9) |
| 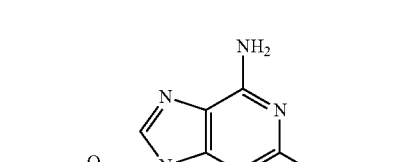 | 2.9 | 1.7 | 3.2 | Not Tested | 1.9/22.4 | 2.4/8.6 | 21/9.2 |

TABLE 8A-continued

| | Cytotoxicity: MTT IC$_{50}$ (μM) | | | | | | |
|---|---|---|---|---|---|---|---|
| Structure | PBM | CEM | Vero | Huh7 | Bone Marrow (GM Lineage) | Bone Marrow (Erythroid Lineage) | Macrophages |
| [structure: 2-fluoro-adenine nucleoside with 4'-ethynyl ribose] | 2.2 | 1.9 | 12.9 | 11.4 | 0.4/12.7 | 0.7/5.4 | 3.2 ± 0.3 |
| [structure: cyclohexanone-piperidinedione compound] | 2.5 | 0.06 | 0.7 | 0.9 | Not performed | Not performed | 6.9 ± 0.9 |

TABLE 8B

| | Cytotoxicity: IC50 (μM) | | | |
|---|---|---|---|---|
| | MTS | MTT | | MTT/MTS |
| Structure | PBM | CEM | Vero | Huh7 |
| [structure: fluoro-benzisothiazolone with benzodioxole] | 58.3 ± 10.9† | 3.7 | 20.1 | 378.8 ± 19.2 |

Example 4

Mitochondrial Toxicity Assays in HepG2 Cells:
  i) Effect of Compounds on Cell Growth and Lactic Acid Production: The effect on the growth of HepG2 cells can be determined by incubating cells in the presence of 0 μM, 0.1 μM, 1 μM, 10 μM and 100 μM drug. Cells (5×10$^4$ per well) can be plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number can be determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells," Antimicrob. Agents Chemother. 2000; 44: 496-503.

To measure the effects of the compounds on lactic acid production, HepG2 cells from a stock culture can be diluted and plated in 12-well culture plates at 2.5×10$^4$ cells per well. Various concentrations (0 μM, 0.1 μM, 1 μM, 10 μM and 100 μM) of compound can be added, and the cultures can be incubated at 37° C. in a humidified 5% CO$_2$ atmosphere for 4 days. At day 4, the number of cells in each well can be determined and the culture medium collected. The culture medium can then be filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of test compounds indicates a drug-induced cytotoxic effect.

ii) Effect on Compounds on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay can be used in all studies described in this application that determine the effect of compounds on mitochondrial DNA content. In this assay, low-passage-number HepG2 cells are seeded at 5,000 cells/well in collagen-coated 96-well plates. Test compounds are added to the medium to obtain final concentrations of 0 μM, 0.1 μM, 10 μM and 100 μM. On culture day 7, cellular nucleic acids can be prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the ß-actin or rRNA gene can be amplified from 5 µl of the eluted nucleic acids using a multiplex Q-PCR protocol with suitable primers and probes for both target and reference amplifications. For COXII the following sense, probe and antisense primers can be used, respectively: 5'-TGCCCGC-CATCATCCTA-3' (SEQ ID 1), 5'-tetrachloro-6-carboxyfluorescein-TCCTCATCGCCCTCCCATCCC-TAMRA-3' (SEQ ID 2) and 5'-CGTCTGTTATGTAAAGGATGCGT-3' (SEQ ID 3). For exon 3 of the B-actin gene (GenBank accession number E01094) the sense, probe, and antisense primers are 5'-GCGCGGCTACAGCTTCA-3' (SEQ ID 4), 5'-6-FAM-CACCACGGCCGAGCGGGATAMRA-3' (SEQ ID 5) and 5'-TCTCCTTAATGTCACGCACGAT-3' (SEQ ID 6), respectively. The primers and probes for the rRNA gene are commercially available from Applied Biosystems. Since equal amplification efficiencies are obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where Δ Δ CT is (CT for average target test sample–CT for target control)–(CT for average reference test–CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug indicates mitochondrial toxicity.

Example 5

Mitochondrial Toxicity—Glu/Gal
Protocol Summary
HepG2 cells are plated on 96 or 384 well tissue culture polystyrene plates. After 24 hr the cells are dosed with test compound at a range of concentrations and incubated for 72 hr in medium supplemented with either galactose or glucose. Test compounds are said to cause mitochondrial toxicity if the cells grown in galactose-containing medium are more sensitive to the test compound than the cells grown in glucose-containing medium.
Objective: To measure the sensitivity of HepG2 cells grown in medium containing either galactose or glucose to the test compound.
Experimental Procedure
HepG2 human hepatocellular carcinoma cells are plated on 96 or 384-well tissue culture polystyrene plates containing either galactose or glucose containing medium supplemented with 10% fetal bovine serum and antibiotics and incubated overnight. The cells are dosed with increasing concentrations of the test compound (final DMSO concentration 0.5%; typical final test compound concentrations of 100, 30, 10, 3, 1, 0.3, 0.1, 0.03 µM for an eight point dose response curve; n=3 replicates per concentration) and the cells are incubated for 72 hr. Appropriate controls are simultaneously used as quality controls. Cell viability is measured using Hoechst staining and cell counting by a HCS reader.

Example 6

Mitochondrial Toxicity Assays in Neuro2A Cells
To estimate the potential of the compounds of this invention to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% (CC50) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. ddC and AZT can be used as control nucleoside analogs.

Example 7

Assay for Bone Marrow Cytotoxicity
Primary human bone marrow mononuclear cells can be obtained commercially from Cambrex Bioscience (Walkersville, MD). CFU-GM assays is carried out using a bilayer soft agar in the presence of 50 units/mL human recombinant granulocyte/macrophage colony-stimulating factor, while BFU-E assays used a ethylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, JP, Schinazi, RF, Chu, C K, and Xie, M Y. Comparison of cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT is used as a positive control. Cells can be incubated in the presence of the compound for 14-18 days at 37° C. with 5% $CO_2$, and colonies of greater than 50 cells can be counted using an inverted microscope to determine the $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 8

HIV Assay
PBM cells or macrophages were incubated with various concentrations of antiviral agents for 6 days PBM cells) or 1 days (macrophages), followed by harvest of supernatants and quantification of extracellular HIV using the RT assay or p24 assays as previously described (Gavegnano and Schinazi et al, 2012, AAC). AZT (positive control), no drug controls, or virus alone were also performed in each assay. Assays were performed in 8 independent experiments. The Chou and Tallalay method was used to calculate the effective inhibitory concentration 50/90 as previously described (Gavegnano and Schinazi et al, 2012, AAC). The Median Effective Concentration ($EC_{50}$) ranges of compound 7 against HIV in PBM cells and macrophages are shown in Table 5:

TABLE 5

| Drug | PBM Cells | | Macrophages | |
|---|---|---|---|---|
| | EC$_{50}$ (μM) | EC$_{90}$ (μM) | EC$_{50}$ (μM) | EC$_{90}$ (μM) |
| EFdA | 0.000000001 | 0.0000001 | 0.00000007 | 0.00001 |
| EFrA | 3.2 | 19.1 | 0.001 | 0.02 |
| (pyrazolo-pyridinedione compound) | >100 | | 0.03 | 0.3 |
| (acetyl phenothiazine) | >100 | | 0.02 | 0.2 |
| (methoxyphenyl-aminophenyl urea) | >100 | | 0.001 | 0.1 |
| AZT | 0.003 | 0.03 | 0.002 | 0.09 |

The Median Effective Concentration (EC$_{50}$) ranges of a series of compounds against HIV in PBM cells and macrophages are shown in Table 5A:

TABLE 5A

| Compound | Antiviral Potency | |
|---|---|---|
| | PBM Cells - EC$_{50/90}$ (μM) | Macrophages - EC$_{50/90}$ (μM) |
| (structure 1) | >10 (12) | 16.6 +/− 3.2/ >100 (86) |
| (structure 2) | >10 (14) | 0.0001 +/− 0.006/0.009 +/− 0.007 |
| (structure 3) | 0.000000001/0.0000001 | 0.00000003/0.000000007 |
| (structure 4) | 1.8 +/− 0.4 | 0.001 +/− 0.002/0.02 +/− 0.01 |
| (structure 5) | N/A | Not performed |
| (structure 6) | 0.7/12.9 | 0.009/0.3 |

Example 9

Assay for NTP Incorporation and Block of NTP Incorporation by NTP Chain Terminators During DNA Synthesis of HIV-1 RT Using [µ-32P]UTP Ext-T DNA 23-mer primer annealed to the RNA 40-mer template (10 nM complex) can be extended by 200 nM HIV-1 RT for 45 min in the 1-α Reaction Buffer with the macrophage and T cell dNTP or NTP using the identical non-radioactive UTP and radioactive [α-32P]UTP ratio (690:1), in the presence of varying concentrations of triphosphorylated nucleoside. Following a quench with 10 mM EDTA, the reaction products can be further purified with a Qiagen nucleotide removal column. The reaction products with [α-32P]UTP can be normalized with a 5-prime-end 32P-labeled 17-mer loading control primer, which can be added in an equal amount after the reactions are terminated as described (Aggarwal, S., Bradel-Tretheway, B., Takimoto, T., Dewhurst, S., and Kim, B. PloS One 5, e10372). To monitor the entire DNA polymerization under the conditions described in this experiment, the identical reactions can be conducted with the 5-prime-end 32P-labeled 23-mer Ext-T DNA template annealed to the 40-mer RNA template with non-radioactive dNTPs in both negative (no enzyme) and positive (250 mM dNTP substrate) controls, generating no primer extension and full primer extension, respectively.

Example 10

In Vitro Human Mitochondrial RNA Polymerase (POLRMT) Assay

In vitro RNA nucleotide incorporation assays with POLRMT (INDIGO Biosciences) can be performed as previously described (Arnold et al. 2012). Briefly, $^{32}$P-radiolabeled RNA primer (5'-UUUUGCCGCGCC) (SEQ ID No. 7) can be hybridized to 3 molar excess of the appropriate DNA template (5'-GGGAATGCANGGCGCGGC (SEQ ID No. 8) where position N can be replaced by A, T, or C). 125 nM of POLRMT can be incubated with 500 nM of 5'-radiolabeled RNA/DNA hybrid, 10 mM MgCl$_2$ and 100 µM of the corresponding nucleoside triphosphate. For non-nucleoside analogs, 100 µM of inhibitor can be added at the same time as 100 µM UTP. Incorporation can be allowed to proceed for 2 h at 30° C. and reactions are stopped by the addition of 10 mM EDTA and formamide. Samples are visualized on 20% denaturing polyacrylamide gel. Data can be analyzed by normalizing the product fraction for each nucleoside triphosphate analog to that of the corresponding natural nucleoside triphosphate.

Example 11

Effect of Nucleotide Analogs on the DNA Polymerase and Exonuclease Activities of Mitochondrial DNA Polymerase γ i) Purification of Human Polymerase γ: The recombinant large and small subunits of polymerase γ can be purified as described previously (see Graves S W, Johnson A A, Johnson K A. Expression, purification, and initial kinetic characterization of the large subunit of the human mitochondrial DNA polymerase. *Biochemistry*. 1998, 37, 6050-8; Johnson A A, Tsai Y, Graves S W, Johnson K A. Human mitochondrial DNA polymerase holoenzyme: reconstitution and characterization. Biochemistry 2000; 39: 1702-8). The protein concentration can be determined spectrophotometrically at 280 nm, with extinction coefficients of 234,420, and 71,894 M-1 cm-1 for the large and the small subunits of polymerase γ, respectively.

ii) Kinetic Analyses of Nucleotide Incorporation: Pre-steady-state kinetic analyses can be performed to determine the catalytic efficiency of incorporation (k/K) for DNA polymerase γ for nucleoside-TP and natural dNTP substrates. This allowed determination of the relative ability of this enzyme to incorporate modified analogs and predict toxicity. Pre-steady-state kinetic analyses of incorporation of nucleotide analogs by DNA polymerase γ would be carried out essentially as described previously (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. *Antiviral Res.* 2004, 62, 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. *Antimicrob Agents Chemother.* 2004, 48, 1300-6). Briefly, a pre-incubated mixture of large (250 nM) and small (1.25 mM) subunits of polymerase γ and 60 nM DNA template/primer in 50 mM Tris-HCl, 100 mM NaCl, pH 7.8, can be added to a solution containing MgCl$_2$ (2.5 mM) and various concentrations of nucleotide analogs. Reactions can be quenched and analyzed as described previously. Data can be fit to the same equations as described above.

iii) Assay for Human Polymerase γ 3' 5' Exonuclease Activity: The human polymerase γ exonuclease activity can be studied by measuring the rate of formation of the cleavage products in the absence of dNTP. The reaction can be initiated by adding MgCl$_2$ (2.5 mM) to a pre-incubated mixture of polymerase γ large subunit (40 nM), small subunit (270 nM), and 1,500 nM chain-terminated template/primer in 50 mM Tris-HCl, 100 mM NaCl, pH 7.8, and quenched with 0.3M EDTA at the designated time points. All reaction mixtures would be analyzed on 20% denaturing polyacrylamide sequencing gels (8M urea), imaged on a Bio-Rad GS-525 molecular image system, and quantified with Molecular Analyst (Bio-Rad). Products formed from the early time points would be plotted as a function of time. Data would be fitted by linear regression with Sigma Plot (Jandel Scientific). The slope of the line can be divided by the active enzyme concentration in the reaction to calculate the kexo for exonuclease activity (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004; 62: 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004; 48: 1300-6).

Example 12

Synthesis of Nucleoside Analog Triphosphates

Nucleoside analog triphosphates can be synthesized from the corresponding nucleosides, using the Ludwig and Eckstein's method. (Ludwig J, Eckstein F. "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one" *J. Org. Chem.* 1989, 54 631-5) The crude nucleoside analog triphosphates can be purified, for example, by FPLC using a HiLoad 26/10 Q Sepharose Fast Flow Pharmacia column and gradient of TEAB buffer (pH 7.0). The product can be characterized by one or more of UV spectroscopy, proton NMR, phosphorus NMR, mass spectroscopy and/or HPLC.

The resulting triphosphates can be used as controls for the cellular pharmacology assays described above and for kinetic work with HIV and human Pols.

Example 13

Inhibition of Human DNA Polymerases by NTP's
Study Objectives

To determine whether a nucleoside-triphosphate analog inhibits human DNA polymerases Alpha, Beta and Gamma and to calculate $IC_{50}$ values.

Materials and Methods

Human DNA Polymerase Alpha—Enzyme can be purchased from Chimerx (cat #1075) and assayed based on their recommendations with some modifications. The 2'-Me-UTP was treated with Inorganic Pyrophosphatase (Sigma) to remove any pyrophosphate contamination. A final concentration of 500 µM 2'-Me-UTP can be incubated with 1 mM DTT, 50 mM Tris, 50 mM NaCl, 6 mM $MgCl_2$, and 1 unit of pyrophosphatase for 1 hour at 37° C. followed by inactivation at 95° C. for 10 minutes. A mixture of 0.05 units of Human DNA Polymerase Alpha and a 5'end radiolabeled 24nt DNA primer (5'-TCAGGTCCCTGTTCGGGCGC-CACT) (SEQ ID 9) anneal to a 48nt DNA template (5'-CAGTGTG-GAAAATCTCTAGCAGTGGCGCCCGAACAGGGACCT-GAAAGC) (SEQ ID 10) can be mixed with increasing concentrations of compound from 0 to 100 µM in 60 mM Tris-HCl (pH 8.0), 5 mM magnesium acetate, 0.3 mg/ml bovine serum albumin, 1 mM dithiothreitol, 0.1 mM spermine, 0.05 mM of each dCTP, dGTP, dTTP, dATP in a final reaction volume of 20 µl for 5 min at 37° C. (all concentrations represent final concentrations after mixing). The reactions can be stopped by mixing with 0.3 M (final) EDTA. Products are separated on a 20% polyacrylamide gel and quantitated on a Bio-Rad Molecular Imager FX. Results from the experiments can be fit to a dose response equation, (y min+((y max)−(y min)))/(1+(compound concentration)/$IC_{50}$Ŷslope) to determine $IC_{50}$ values using Graphpad Prism or SynergySoftware Kaleidagraph. Data can be normalized to controls. Human DNA Polymerase Beta—Enzyme can be purchased from Chimerx (cat #1077) and assayed based on their recommendations with some modifications. A mixture of 0.1 units of Human DNA Polymerase Beta and a 5'end radiolabeled 24nt DNA primer (5'-TCAGGTCCCTGTTCGGGCGCCACT) (SEQ ID 11) anneal to a 48nt DNA template (5'-CAGTGTG-GAAAATCTCTAGCAGTGGCGCCCGAACAGGGACCT-GAAAGC) (SEQ ID 12) can be mixed with increasing concentrations of compound from 0 to 100 µM in 50 mM Tris-HCl (pH 8.7), 10 mM KCl, 10 mM $MgCl_2$, 0.4 mg/ml bovine serum albumin, 1 mM dithiothreitol, 15% (v/v) glycerol, and 0.05 mM of each dCTP, dGTP, dTTP, dATP in a final reaction volume of 20 µl for 5 min at 37° C. (all concentrations represent final concentrations after mixing).

The reactions can be stopped by mixing with 0.3 M (final) EDTA. Products can be separated on a 20% polyacrylamide gel and quantitated on a Bio-Rad Molecular Imager FX. Results from the experiments can be fit to a dose response equation, (y min+((y max)−(y min)))/(1+(compound concentration)/$IC_{50}$)1'slope) to determine $IC_{50}$ values using Graphpad Prism or SynergySoftware Kaleidagraph. Data can be normalized to controls. Human DNA Polymerase Gamma—Enzyme can be purchased from Chimerx (cat #1076) and assayed based on their recommendations with some modifications. A mixture of 0.625 units of Human DNA Polymerase Gamma and a 5'end radiolabeled 24nt DNA primer (5'-TCAGGTCCCTGTTCGGGCGCCACT) (SEQ ID 13) anneal to a 36nt DNA template (5'-TCTCTAGAAGTGGCGCCCGAACAGGGACCT-GAAAGC) (SEQ ID 14) can be mixed with increasing concentrations of compound from 0 to 100 µM in 50 mM Tris-HCl (pH 7.8), 100 mM NaCl, 5 mM MgCh, and 0.05 mM of each dCTP, dGTP, dTTP, dATP in a final reaction volume of 20 µl for 200 min at 37° C. (all concentrations represent final concentrations after mixing). The reactions can be stopped by mixing with 0.3 M (final) EDTA. Products can be separated on a 20% polyacrylamide gel and quantitated on a Bio-Rad Molecular Imager FX. Results from the experiments can be fit to a dose response equation, (y min+((y max)−(y min)))/(1+(compound concentration)/$IC_{50}$)^slope) to determine $IC_{50}$ values using Graphpad Prism or SynergySoftware Kaleidagraph. Data can be normalized to controls.

Example 14

Cellular Pharmacology in HepG2 Cells

HepG2 cells are obtained from the American Type Culture Collection (Rockville, MD), and are grown in 225 $cm^2$ tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of $2.5 \times 10^6$ cells per well in a 6-well plate and exposed to 10 µM of [$^3$H] labeled active compound (500 dpm/pmol) for the specified time periods.

The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 pal of cold methanol for one hour in an ice bath. The extracts are then combined, dried under gentle filtered air flow and stored at −20° C. until HPLC analysis.

Example 15

Cellular Pharmacology in PBM Cells

Test compounds are incubated in PBM cells at 50 µM for 4 h at 37° C. Then the drug containing media is removed and the PBM cells are washed twice with PBS to remove extracellular drugs. The intracellular drugs are extracted from $10 \times 10^6$ PBM cells using 1 mL 70% ice-cold methanol (containing 10 nM of the internal standard ddATP). Following precipitation, the samples are maintained at room temperature for 15 min followed by vortexing for 30 sec, and then stored 12 h at −20° C. The supernatant is then evaporated to dryness. Dry samples would be stored at −20° C. until LC-MS/MS analysis. Prior to analysis, each sample is reconstituted in 100 µL mobile phase A, and centrifuged at 20,000 g to remove insoluble particulates.

Gradient separation is performed on a Hypersil GOLD column (100×1.0 mm, 3 µm particle size; Thermo Scientific, Waltham, MA, USA). Mobile phase A consists of 2 mM ammonium phosphate and 3 mM hexylamine. Acetonitrile is increased from 10 to 80% in 15 min, and kept at 80% for 3 min. Equilibration at 10% acetonitrile lasts 15 min.

The total run time is 33 min. The flow rate is maintained at 50 µL/min and a 10 µL injection is used. The autosampler and the column compartment are typically maintained at 4.5 and 30° C., respectively.

The first 3.5 min of the analysis is diverted to waste. The mass spectrometer is operated in positive ionization mode with a spray voltage of 3.2 kV.

Example 16

Analysis of the Efficacy of the Compounds Described Herein Against HIV-1 Infection in Macrophages The ability of the compounds to treat HIV-1 infection in macrophages, specifically, can be assessed, for example, using the procedures described in Koppensteiner et al., "Macrophages and their relevance in Human Immunodeficiency Virus Type I infection," Retrovirology 20129:82 (2012).

Example 17

Chikungnya Virus Antiviral Activity Assay

Methods for evaluating the efficacy of the compounds described herein against Chikungunya virus is shown, for example, in Ehteshami, M., Tao, S., Zandi, K., Hsiao, H. M., Jiang, Y., Hammond, E., Amblard, F., Russell, O. O., Mertis, A., and Schinazi, R. F.: Characterization of β-D-N4-hydroxycytidine as a novel inhibitor of chikungunya virus. Antimirob Agents Chemother, 2017 April; 61(4): e02395-16.

Anti-Chikungunya Activity can also be evaluated as outlined in "Anti-Chikungunya Viral Activities of Aplysiatoxin-Related Compounds from the Marine Cyanobacterium *Trichodesmium erythraeum*" Gupta, D. K.; Kaur, P.; Leong, S. T.; Tan, L. T.; Prinsep, M. R.; Chu, J J. H. Mar Drugs. January 2014; 12(1): 115-127; 10.3390/md12010115 and references cited therein.

Example 18

Assaying Compounds for Efficacy Against Mayaro Virus Infection:

A representative assay for determining the efficacy of the compounds described herein against the Mayaro virus is disclosed in Cavalheiro et al., "Macrophages as target cells for Mayaro virus infection: involvement of reactive oxygen species in the inflammatory response during virus replication," Anais da Academia Brasileira de Ciencias (2016) 88(3): 1485-1499, (Annals of the Brazilian Academy of Sciences). The procedures are summarized below.

Cell Culture and Virus Propagation

RAW 264.7, a mouse leukaemic macrophage cell line, and J774, a mouse reticulum sarcoma cell line, can be maintained in RPMI-1640 medium (LGC) supplemented with 10% fetal bovine serum (FBS; Invitrogen Life Technologies) in a humidified incubator at 37° C. with 5% $CO_2$. Mouse peritoneal macrophages can be obtained from C57B1/6 animals by the intraperitoneal injection of 1 mL of sterile 3% thioglycollate. After 96 h, the peritoneal macrophages can be harvested, washed with RPMI and centrifuged at 1,500 rpm for five minutes. Then, the macrophages can be plated at a density of $2 \times 10^6$ cells/well in a 6-well plate with RPMI-1640 supplemented with 10% FBS and incubated at 37° C. with 5% $CO_2$. After 24 h, the plates can be washed with RPMI to remove non-adherent cells before the assays.

MAYV (ATCC VR 66, strain TR 4675) and SINV (AR339) can be propagated in BHK-21 cells grown in α-Minimum Essential Medium (α-MEM; Invitrogen Life Technologies) supplemented with 10% FBS. The cells can be infected with a multiplicity of infection (MOI) of 0.1. After 16 h for SINV and 30 h for MAYV, the culture media can be harvested and cell debris can be removed by centrifugation at 2,000×g for 10 min and the supernatant can be stored at −80° C. Virus stocks titers can be determined by plaque assay in BHK-21 cells.

Macrophage Infection Assays

Cells can be incubated with MAYV or SINV at a MOI of 1 (for RAW 264.7 and J774) or 5 (for primary peritoneal macrophages), for 1 h at 37° C. in 5% $C_{O2}$. Then, the medium containing the non-adsorbed virus can be removed, the cells can be washed with serum-free medium and cultured in RPMI supplemented with 5% FBS, at 37° C. in 5% $C_{O2}$. After the desired periods of infection, conditioned media can be collected for virus titration, LDH assay and cytokine quantification. Cellular extracts can be used for MTT and flow cytometry assays. Virus inactivated by heating at 65° C. for 30 min can be used as control. In some experiments, cells can be treated with 10 mM N-acetyl-L-cysteine (NAC; Sigma-Aldrich) or 50 µM apocynin (Sigma-Aldrich) for 15 h after infection with MAYV.

Virus Titration by Plaque Assay

BHK-21 cells can be seeded, for example, at a density of $1.25 \times 10^5$ cells per well in 12-wells plates and incubated at 37° C. overnight. Ten-fold serial dilutions of the virus samples can be prepared in α-MEM and incubated with the cells for 1 h at 37° C. (0.2 mL per well). After 1 h adsorption, 2 mL of 1% carboxymethylcellulose (w/v) (Sigma-Aldrich) in α-MEM supplemented with 2% FBS can be layered onto the infected monolayers and the cells can be incubated at 37° C. for 30 h or 48 h, for SINV or MAYV, respectively. Plaques can be visualized by staining the monolayer with 1 mL 1% crystal violet in 20% ethanol.

Cell Viability Assays

Determination of macrophage viability during infection can be assessed by 3-(4,5-dimethylthiazol-2-yl)-2,5-diphenyltetrazolium bromide (MTT) or lactate dehydrogenase (LDH) release assays. For the MTT assay, cells can be incubated with 0.5 mL 0.5 mg/mL MTT (USB Corporation) in PBS solution for 90 min at 37° C. Then, unreacted dye can be discarded and formazan crystals can be An Acad Bras Cienc (2016) 88 (3) 1488 Mariana G. Cavalheiro et al. solubilized in 0.04 M HCl solution in isopropanol (1 mL per well). The absorbance of samples can be measured at 570 nm and 650 nm for background correction. Lactate dehydrogenase (LDH) release from infected macrophages can be determined by using an LDH detection kit (Promega Cyto-Tox 96 assay kit). The procedures can be performed according to manufacturer's instructions.

Quantitation of Infected Cells by Flow Cytometry

Flow cytometry analysis can be performed to assess the frequency of MAYV- or SINV-infected cells by detecting intracellular viral antigens. After the desired periods of infection, cells can be washed with PBS, detached by scraping, harvested and fixed in 4% formaldehyde in PBS at room temperature for 15 min. After washing, cells can be permeabilized with 0.1% saponin in PBS and incubated with blocking solution (PBS supplemented with 2% FBS and 0.1% bovine serum albumin) for 20 min, at room temperature. Then, cells can be incubated for 1 h with mouse anti-Eastern Equine Encephalitis virus monoclonal antibody (Chemicon International, Millipore), which reacts with an E1 epitope shared by all alphaviruses. Then, cells can be washed and stained with anti-mouse IgG conjugated to Alexa Fluor 488 (Invitrogen) for 30 min. The percentage of infected cells can be analyzed by FACScan Flow Cytometer and CellQuest software (Becton Dickinson).

Characterization of Cell Death

Apoptosis/necrosis after infection can be quantified by a double staining method using The Vybrant Apoptosis Assay Kit #2 (Molecular Probes). After the infection period, RAW 264.7 cells can be washed with PBS, detached by scraping, harvested and stained with Annexin V Alexa Fluor 488 (0.5 µg/mL) and propidium iodide (PI, 0.25 µg/mL). To further characterize MAYV-induced cell death, the activity of caspases 3 and 7 can be measured using the Muse™ Caspase-3/7 Kit (Millipore) adapted to flow cytometry. Cells can be washed with PBS, detached by scraping, harvested and incubated with Muse™ Caspase-3/7 Reagent 1:8 and Muse™ Caspase 7-AAD, according to the manufacturer's protocol. For both assays, the percentage of apoptotic and necrotic cells can be analyzed by FACScan Flow Cytometer using the CellQuest software (Bectan Dickinson). UV radiated cells and cells subjected to a freeze-thaw procedure can be used as controls.

Quantitation of Reactive Oxygen Species (ROS)

The amount of intracellular reactive oxygen species (ROS) can be measured by the formation of the oxidized derivative of 5-(and 6-)-chloromethyl-2',7'-dichlorodihydrofluorescein diacetate (DCF, Molecular Probes). After 15 h of infection with MAYV, adherent cells can be washed with PBS and incubated with DCF 0.5 µM for 45 minutes. Then, the cells can be washed again, detached by scraping and harvested and analyzed by FACScan Flow Cytometer using the CellQuest software (Bectan Dickinson).

Quantitation of Cytokines The concentrations of cytokines in the conditioned medium of macrophage cultures can be determined by ELISA. TNF concentration can be quantified using the Standard ELISA Development kit (Pepro-Tech), according to the manufacturer's protocol.

Example 19

Yellow Fever Virus (YFV) Antiviral Activity Assay: Primary Assay for Antiviral Activity A monolayer of Human Rhabdomyosarcoma (RD) cells will be grown in 96-well plate in MEM containing 2% inactivated FBS. The tested compounds will be added to the wells in triplicate together with YFV at an MOI=1. The plate will then be incubated at 37° C. with 5% $CO_2$ for 72 hours. The assay will be conducted in triplicate for each concentration of each compound. After three days, the plate will be viewed under the microscope and the degree of cytopathic effect (CPE) as measure of virus replication inhibition will be expressed as the percent yield of virus control. The results will be evaluated by performing the MTS assay (Promega, WI, USA) according to the manufacturer's protocols. All experiments will be repeated three times independently.

Focus Forming Unit Reduction Assay (FFURA)

Antiviral activity of each compound will be determined by measuring the reduction in the number of YFV infectious foci in RD cells following treatment with increasing concentrations of each compound. Briefly, infected RD cells which will be treated with different concentrations of each compound will be incubated for 2 days post infection using conditioned-growth medium supplemented with 2% FBS and 1.5% carboxymethyl cellulose (CMC). Antiviral activity of each compound will be determined after visualizing and counting viral foci. The number of YFV foci will be counted using Elispot machine and the virus titer will be expressed as Foci Forming-Unit (FFU). Antiviral activities of the compounds will be determined by calculating the percentage of foci reduction (% RF) against the controls maintained in parallel using the following formula; RF (%)=(C−T)×100/C, where, C is the mean of the number of foci from triplicates treatment without compound added (vehicle control) and T is the mean of the number of foci from triplicates of each treatment measures with the respective compound. Results will represent as the means±standard error of the mean (SEM) from triplicate assay from three independent experiments. Results were confirmed by virus yield reduction assay using quantitative RT-PCR.

Virus Yield Reduction Assay

Monolayers of RD cells will be prepared in 96-well cell culture microplate and overlaid with YFV (moi=0.1) for 1 hour. After virus adsorption, cells will be washed 3 times with cold sterile PBS to remove unattached viruses and then the cells will be treated for 2 days with increasing concentrations of the tested compounds. After 2 days, the YFV RNA will be extracted from the infected/treated cells and supernatant separately and the yield of YFV will be quantified using a one-step specific quantitative RT-PCR for YFV. Nevertheless, the antiviral activity of each nucleoside analogues will be investigated using focus forming unit reduction assay (FFURA) as described previously Time-of-Drug-Addition Assay Confluent monolayers of RD cells will be prepared in 96-well cell culture plate and will be pre-treated with $EC_{90}$ of each effective drug for 2 h before infection with YFV at MOI=1, concurrently with infection as well as 1, 2, 4 and 6 h post-infection. The cells will then be incubated in the presence of compound for 48 h. At the end of the incubation period, viral load for each time point of treatment will be determined using qRT-PCR as mentioned above.

Statistical Analysis

Graph Pad Prism for Windows, Version 5 (Graph Pad Software Inc., San Diego, CA, 2005) will be used to determine the half maximal effective concentration $EC_{50}$ values and also $EC_{90}$ of each effective compound. All $EC_{50}$ and $EC_{90}$ values will be calculated as the means±standard error of the mean (SEM) from triplicate assay from three independent experiments.

Example 20

HCV Replicon Assay I

Huh 7 Clone B cells containing HCV Replicon RNA can be seeded in a 96-well plate at 5000 cells/well, and the compounds tested at 10 μM in triplicate immediately after seeding. Following five days incubation (37° C., 5% $CO_2$) total cellular RNA can be isolated by using versaGene RNA purification kit from Gentra. Replicon RNA and an internal control (TaqMan rRNA control reagents, Applied Biosystems) can be amplified in a single step multiplex Real Time RT-PCR Assay. The antiviral effectiveness of the compounds can be calculated by subtracting the threshold RT-PCR cycle of the test compound from the threshold RT-PCR cycle of the no-drug control (ACt HCV). A ACt of 3.3 equals a 1-log reduction (equal to 90% less starting material) in Replicon RNA levels. The cytotoxicity of the compounds can also be calculated by using the ACt rRNA values. 2'-C-Me-C can be used as the positive control. To determine $EC_{90}$ and $IC_{50}$ values, ACt: values can first be first converted into fraction of starting material and then can be used to calculate the % inhibition.

Example 21

Efficacy of the Compounds Described Herein Against Dengue

The essential role of a particular viral protein (Dengue virus envelope protein (E)) in viral propogation. Mondotte et al., J. Virol. July 2007, vol. 81 no. 13 7136-7148 discloses an assay useful for identifying compounds for treating infections caused by the Dengue virus, and this assay can be used to identify those compounds described herein which are active against Dengue.

Another assay is described in Levin, 14th International Symposium on Hepatitis C Virus & Related Viruses, Glasgow, UK, 9-13 Sep. 2007. The assay relates to human and Dengue virus polymerase, where putative compounds can be tested against the enzymes, preferably in duplicate, over a range of concentrations, such as from 0.8 mM to 100 mM. The compounds can also be run alongside a control (no inhibitor), a solvent dilution (0.016% to 2% DMSO) and a reference inhibitor.

A suitable high throughput assay for Dengue is described in Lim et al., Antiviral Research, Volume 80, Issue 3, December 2008, Pages 360-369. Dengue virus (DENV) NS5 possesses methyltransferase (MTase) activity at its N-terminal amino acid sequence and is responsible for formation of a type 1 cap structure, m7GpppAm2' —O in the viral genomic RNA. Optimal in vitro conditions for DENV2 2' —O-MTase activity can be characterized using purified recombinant protein and a short biotinylated GTP-capped RNA template. Steady-state kinetics parameters derived from initial velocities can be used to establish a robust scintillation proximity assay for compound testing. Preincubation studies by Lim et al., Antiviral Research, Volume 80, Issue 3, December 2008, Pages 360-369, showed that MTase-AdoMet and MTase-RNA complexes can be equally catalytically competent and the enzyme supports a random bi kinetic mechanism. Lim validated the assay with competitive inhibitory agents, S-adenosyl-homocysteine and two homologues, sinefungin and dehydrosinefungin. A GTP-binding pocket present at the N-terminal of DENV2 MTase can be previously postulated to be the cap-binding site. This assay allows rapid and highly sensitive detection of 2'-O-MTase activity, and can be readily adapted for high-throughput screening for inhibitory compounds.

Example 22

Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473).

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay may be useful for screening entry inhibitors.

Diagnosis of Norovirus Infection

One can diagnose a norovirus infection by detecting viral RNA in the stools of affected persons, using reverse transcription-polymerase chain reaction (RT-PCR) assays. The virus can be identified from stool specimens taken within 48 to 72 hours after onset of symptoms, although one can obtain satisfactory results using RT-PCR on samples taken as long as 7 days after the onset of symptoms. Other diagnostic methods include electron microscopy and serologic assays for a rise in titer in paired sera collected at least three weeks apart. There are also commercial enzyme-linked immunoassays available, but these tend to have relatively low sensitivity, limiting their use to diagnosis of the etiology of outbreaks. Clinical diagnosis of norovirus infection is often used, particularly when other causative agents of gastroenteritis have been ruled out.

Example 23

Anti-RSV Activity

Anti-RSV activity may be evaluated as outlined in the references below:

"Polyadenylation-dependent screening assay for respiratory syncytial virus RNA transcriptase activity and identification of an inhibitor" Stephen W. Mason, Carol Lawetz, Yvon Gaudette, Florence Dô, Erika Scouten, Lisette Lagacé, Bruno Simoneaul Michel Liuzzi. Nucl. Acids Res. (2004) 32 (16): 4758-4767; doi: 10.1093/nar/gkh809.

"Screening and evaluation of anti-respiratory syncytial virus compounds in cultured cells" Lundin A1, Bergström T, Trybala E. Methods Mol Biol. 2013; 1030: 345-63. doi: 10.1007/978-1-62703-484-5_27.

"A fluorescence-based high-throughput antiviral compound screening assay against respiratory syncytial virus" Kwanten L1, De Clerck B, Roymans D. Methods Mol Biol. 2013; 1030:337-44. doi: 10.1007/978-1-62703-484-5_26.

Example 24

Anti-Influenza Activity

Anti-influenza activity may be evaluated as outlined in the references below: Schmidtke et al., "A rapid assay for evaluation of antiviral activity against coxsackie virus B3, influenza virus A, and herpes simplex virus type 1," J Virol Methods. 2001 June; 95(1-2):133-43.

Ching-Yao Su, "High-throughput identification of compounds targeting influenza RNA-dependent RNA polymerase activity," PNAS, vol. 107 no. 45, 19151-19156 (Nov. 9, 2010).

"In vitro and in vivo assay systems for study of influenza virus inhibitors" Robert W. Sidwell; Donald F. Smee. Antiviral Research 48(1) 2000, Pages 1-16.

"A cell-based luminescence assay is effective for high-throughput screening of potential influenza antivirals" James W. Noah; William Severson; Diana L. Noah; Lynn Rasmussen; E. Lucile White; Colleen B. Jonsson. Antiviral Research 73(1) 2007, Pages 50-59.

"High-Throughput Screening of a 100,000-Compound Library for Inhibitors of Influenza A Virus (H3N2)" William E. Severson; Michael McDowell; Subramaniam Ananthan; Dong-Hoon Chung; Lynn Rasmussen; Melinda I. Sosa; E. Lucile White; James Noah; Colleen B. Jonsson. J Biomol Screen 2008 13: 879-887, doi:10.1177/1087057108323123.

Example 25

Anti-HEV Activity

Hepatitis E virus (HEV) is a major cause of hepatitis. Hepatitis E virus (HEV) is the principal cause of acute hepatitis on the Indian subcontinent, in southeastern and central Asia, in the Middle East, in Mexico, and in parts of Africa. It is associated with the consumption of fecally contaminated drinking water. Although HEV is associated with a low case fatality rate in the general population, pregnant women in the second and third trimesters are at greater risk (case fatality rates of 10 to 24%) for fulminant hepatitis and fetal loss.

There are several commercial HEV diagnostic assays that can be used to identify infection with HEV (Myint et al., J Clin Microbiol. 2006 April; 44(4): 1581-1583). Myint determined that HEV viremia is universal and has the highest diagnostic score (sensitivity, 85%). The viremia also appears prolonged, starting from the onset of illness and lasting for ≥2 weeks. Given these findings, and in the absence of reference serological assays, HEV RT-PCR can be used as a reference assay for HEV detection.

As viremia does not always coincide with the antibody response in the natural course of HEV infection, detection of IgA alone or together with IgM can provide better specificity and a longer duration of positivity for diagnosis of HEV infection (Takahashi, M., S. Kusakai, H. Mizuo, K. Fujimura, K. Masuko, Y. Sugai T. Aikawa, T. Nishizawa, and H. Okamoto. 2005. Simultaneous detection of immunoglobulin A (IgA) and IgM antibodies against hepatitis E virus (HEV) is highly specific for diagnosis of acute HEV infection. J. Clin. Microbiol. 43:49-56).

Commercial IgM anti-HEV assays can be used, such as the WRAIR assay (Walter Reed Army Institute of Research) and the Genelabs IgM assay (Genelabs Diagnostics (GLD) Pty. Ltd., Singapore).

Commercial enzyme immunoassays (EIAs) for detecting total Ig or IgG anti-HEV can be used, including the Abbott IgG anti-HEV EIA (Abbott Diagnostika, Wiesbaden-Delkenheim, Germany), the GLD IgG (Genelabs Diagnostics (GLD) Pty. Ltd., Singapore), and the WRAIR total Ig anti-HEV EIA (Walter Reed Army Institute of Research).

Of these screens, Myint noted that the Abbott immunoglobulin G (IgG), Genelabs IgG, and Walter Reed Army Institute of Research (WRAIR) IgM assays were about 90% sensitive, and the Abbott IgG and WRAIR total Ig and IgM assays were more than 90% specific.

All HEV strains identified to date appear to belong to the same serotype, and recombinant HEV antigens react well with sera from all geographical origins. However, the Myint study noted that the sensitivity of the serological assays was greater for symptomatic than for asymptomatic HEV infections.

Example 26

Anti-HBV Assay

The anti-HBV activity of the compounds can be determined by treating the AD-38 cell line carrying wild type HBV under the control of tetracycline (see Ladner S. K., Otto M. J., Barker C. S., Zaifert K., Wang G. H., Guo J. T., Seeger C. & King R. W. Antimicrob. Agents Chemother. 1997, 41, 1715-20). Removal of tetracycline from the medium [Tet (−)] results in the production of HBV. The levels of HBV in the culture supernatant fluids from cells treated with the compounds can be compared with that of the untreated controls. Control cultures with tetracycline [Tet (+)] can also be maintained to determine the basal levels of HBV expression. 3TC can be included as positive control.

Example 27

Efficacy of the Compounds Against Herpes Simplex

The efficacy of the compounds against Herpes Simplex 1 or 2 (i.e., HSV1 and HSV2) can be evaluated according to the techniques described in Belshe, et al., N Engl J Med 2012; 366:34-43, which related to a herpes vaccine trial, known as the "Herpevac" trial. Briefly, the efficacy of the compounds in providing prophylaxis can be determined by administering the compound(s) before exposure to HSV1 or HSV2, and, after an appropriate incubation period, determining whether the patient is or is not antibody-negative for HSV-1 and HSV-2. The efficacy of the compounds in treating an HSV1 or HSV2 infection can be determined by administering the compounds to a patient who has previously tested positive for HSV-1 and/or HSV-2, and measuring the response by determining, after administration of the compounds, whether the patient is or is not antibody-negative for HSV-1 and HSV-2.

Example 28

Efficacy Against Ebola Virus

The efficacy of the compounds against the Ebola virus can be determined using an assay similar to that described in Clinical Trial NCT02329054, entitled Efficacy of Favipiravir Against Ebola (JIKI) (JIKI). Briefly, following administration of a compound to a patient infected with Ebola, the following can be evaluated:

Outcome Measures

Primary Outcome Measures: 1. Mortality [Time Frame: Day-14]

Day-0 is the day of the first dose of the compound

Secondary Outcome Measures: 1. Evolution of EBOV plasma RNA and infectious loads [Time Frame: routine care venepuncture (Day-0; end of symptoms (EOS)+72 h and EOS+96 h if EOS>Day-9; or Day-12 and Day-13 if EOS<Day-9); (ii) additional trial venepuncture at: Day-2, Day-4 and Day-30 in group A1; Day-2 and Day-30 in group A2]

2. Occurrence of grade 3 or 4 clinical or biological adverse events (Common Terminology Criteria for Adverse Events, CTAE, v3.0) [Time Frame: participants will be followed for the duration of hospital stay up to Day-14]

3. Evolution of viral micro-diversity of EBOV (including potential resistance mutations) [Time Frame: routine care venepuncture (Day-0; end of symptoms (EOS)+72 h and EOS+96 h if EOS>Day-9; or Day-12 and Day-13 if EOS<Day-9); (ii) additional trial venepuncture at: Day-2, Day-4 and Day-30 in group A1; Day-2 and Day-30 in group A2]

4. Plasma trough concentrations of the administered compound [Time Frame: routine care venepuncture (Day-0; end of symptoms (EOS)+72 h and EOS+96 h if EOS>Day-9; or Day-12 and Day-13 if EOS<Day-9);

(ii) additional trial venepuncture at: Day-2, Day-4 and Day-30 in group A1; Day-2 and Day-30 in group A2]
5. Criteria for cure [Time Frame: Day-30]
Composite criteria for cure are the following:
4 days without fever or significant symptoms and;
able to feed and walk independently and;
two consecutive negative qualitative PCR.
6. Mortality [Time Frame: Day-14 according to the second group definition (AC1, AC2, YC)]
Day-0 is the day of the first dose of the compound.

Example 29

Determining the Efficacy of the Compounds Against ZIKV and DENV Infection

Material and methods for ZIKV and DENV (serotypes 1-4) infections assays:

Viruses: ZIKV PRVABC59 strain (NCBI accession KU501215) was obtained from the Centers for Diseases Control and Prevention. Virus stocks were generated on C6/36 or Vero cells and viral titers are determined by endpoint titration in Vero (African Green monkey kidney) or human cells, including neuroblastoma (U251), and hepatoblastoma (Huh7). DENV stocks (kindly provided by Dr. Guey Chuen Perng (Emory University & National Cheng Kung University, Taiwan) were generated in Vero or Baby Hamster Kidney cells (BHK) (Clark et al., 2016).

Cytopathic-reduction assay for ZIKV or DENV: For the cytopathic-reduction assay, cells (Vero, U251 or Huh7) are seeded in 96-well plates at $1\times10^4$ cells/well and incubated overnight. The next day, culture medium containing 50% cell culture infectious doses of ZIKV or DENV (tested in Vero or BHK cells) are added after which 2-fold serial dilutions of the compounds are added. Cell cytopathic effect (CPE) is measured by MTS readout system (CellTiter 96 AQueous One Solution Proliferation kit, Promega) four (Vero) or five (U251 or Huh7) days after compound addition to determine the levels of ZIKV replication inhibition (Zmurko et al., 2016; Gavegnano et al., 2017). For DENV serotypes 1-4, CPE is measured four to five days after compound addition in Vero or BHK cells.

Focus formation assay: For the focus formation assay (FFA), Vero cells are routinely seeded in 96-well plates at $1.5\times10^4$ cells/well and incubated overnight. Next, culture medium containing 70-100 focus forming units of ZIKV or DENV (serotypes 1-4) plus 2-fold serial dilutions of the compounds are added to the cells and incubated for 2 h followed by the addition of overlay methylcellulose medium. Following 2-3 days of incubation, foci are stained using anti-Flavivirus group antigen (4G2, Millipore), followed by HRP-anti-mouse IgG and TrueBlue substrate, and imaged using CTL-Immunospot S6 Micro Analyzer (Priyamvada et al., 2016).

Real-time RT-PCR assay: For the RT-PCR assays, Vero, U251, or Huh7 cells (15,000/well) are seeded in 96-well microplates, and cultured overnight prior to use for infections with ZIKV (MOI=0.001 for Vero or MOI-0.5 for U251 or Huh7) or DENV (with MOI varying from 0.001 to 0.1 for different stocks of serotypes 1-4 for Vero cells). Compounds are added at a dose-dependent manner 1-2 h after ZIKV or DENV. After four days incubation, purified RNA are reverse transcribed into cDNA and amplified in a one-step RT-PCR multiplex reaction with LightCycler 480 RNA Master Hydrolysis Probe (Roche, Indianapolis, IN) using highly conserved sequences complementary to a 76 bp fragment from the ZIKV envelope gene as previously described by Lanciotti (Lanciotti et al., 2008), and an endogenous control (TaqMan Ribosomal RNA Control or beta globin reagents; Applied Biosystems) by using the LightCycler 480 Instrument II (Roche). For detection of dengue viruses, we utilized oligonucleotides primers and probes serotype-specific that rapidly detects all four serotypes in a fourplex RT-PCR assay (Johnoson et al., 2005). For all virological tests, percent inhibition and $EC_{50}$ value (compound concentration that inhibits viral antigen expression or viral replication by 50%) are determined using CalcuSyn software (Biosoft).

Combination Studies for ZIKV or DENV.

One goal is to focus on compounds with sub-µM concentrations for hit to lead development, with cell selectivity index (SI)≥100. Hit compounds that demonstrate antiviral potency with no apparent cytotoxicity can be selected for drug-drug combinations with compounds that exhibit different mechanism of action, including viral entry and host inhibitors, among others; These combinations can result in synergistic effects and optimal low doses to rapidly eliminate ZIKV or DENV from infected individuals.

One can use the Chou and Talalay method (Chou & Talalay 1984) for determining synergy, antagonism or additivity (Bassit et al., 2008; Schinazi et al., 2012), particularly with respect to combinations.

Material and Methods for DENV2 (Serotype 2) Replicon Assay:

Baby hamster kidney (BHK-21) stable cell lines expressing dengue virus serotype 2 [DENV2, New Guinea C strain, Qing et al., 2010)] was kindly provided by Mehul S. Suthar (Emory University).

DENV2 replicon-harboring baby hamster kidney (BHK) cells are exposed to test compounds at concentrations varying from 0.2 to 20 µM to assessment of antiviral activity. *Renilla* luciferase levels (Promega) are quantified 48 hours after test compounds addition to determine the levels of replication inhibition ($EC_{50}$, µM).

REFERENCES

1. Clark, K. B., Hsiao, H. M., Bassit L., Crowe J. E. Jr., Schinazi R. F., Perng G. C., Villinger F. Characterization of dengue virus 2 growth in megakaryocyte-erythrocyte progenitor cells. Virology. 493, 162-72 (2016).
2. Zmurko, J., Marques, R. E., Schols, D., Verbeken, E., Kaptein, S. J. F. & Neyts, J. The Viral Polymerase Inhibitor 7-Deaza-2'-C-Methyladenosine Is a Potent Inhibitor of In Vitro Zika Virus Replication and Delays Disease Progression in a Robust Mouse Infection Model. PLoS Neglected Tropical Diseases 10, e0004695, doi: 10.1371/journal.pntd.0004695 (2016).
3. Gavegnano C, Bassit L C, Cox B D, Hsiao H-M, Johnson E L, Suthar M, Chakraborty R, Schinazi R F. Jak inhibitors modulate production of replication-competent Zika Virus in Human Hofbauer, Trophoblasts, and Neuroblastoma cells. Pathogens & immunity. 2, 199-218 (2017).
4. Priyamvada L, Quicke K M, Hudson W H, Onlamoon N, Sewatanon J, Edupuganti S, Pattanapanyasat K, Chokephaibulkit K, Mulligan M J, Wilson P C, Ahmed R, Suthar M S, Wrammert J. Human antibody responses after dengue virus infection are highly cross-reactive to Zika virus. PNAS 113, 7852-7857, (2016).
5. Lanciotti R, Kosoy O, Laven J, Velez J, Lambert A, Johnson A, Stanfield S, Duffy M. Genetic and serologic properties of Zika virus associated with an epidemic, Yap State, Micronesia, 2007. Emerg Infect Dis. 14, 1232-1239 (2008).

6. Johnson B W, Russell B J, Lanciotti R S. Serotype-specific detection of dengue viruses in a fourplex real-time reverse transcriptase PCR assay. J Clin Microbiol 43(10), 4977-4983 (2005).
7. Chou T C, Talalay P. Quantitative analysis of dose-effect relationships: the combined effects of multiple drugs or enzyme inhibitors. Adv Enzyme Regul. 22, 27-55 (1984).
8. Bassit L, Grier J, Bennett M, Schinazi R F. Combinations of 2'-C-methylcytidine analogues with interferon-alpha2b and triple combination with ribavirin in the hepatitis C virus replicon system. Antivir Chem Chemother. 19(1), 25-31 (2008).
9. Schinazi R F, Bassit L, Clayton M M, Sun B, Kohler J J, Obikhod A, Arzumanyan A, Feitelson M A. Evaluation of single and combination therapies with tenofovir disoproxil fumarate and emtricitabine in vitro and in a robust mouse model supporting high levels of hepatitis B virus replication. Antimicrob Agents Chemother. 56(12), 6186-91 (2012).
10. Qing M, Liu W, Yuan Z et al., A high-throughput assay using dengue-1 virus like particles for drug discovery. Antiviral Res. 86(2), 163-71 (2010).

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

We claim:
1. A method of treating HIV, comprising administering one or more compounds of Formula (A) or Formula (B) to a patient in need of treatment thereof, wherein Formula (A) and Formula (B) are shown below:

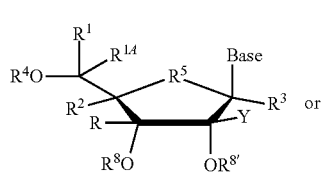

Formula A

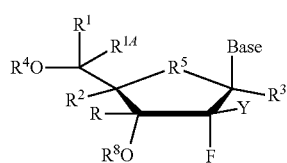

Formula B or a pharmaceutically acceptable salt thereof, wherein:
- Y is H, $C_{1-6}$ alkyl, $C_{1-6}$ haloalkyl, $C_{2-6}$ alkenyl, $C_{2-6}$ alkynyl,
- R is selected from the group consisting of H, substituted or unsubstituted $C_{1-6}$ alkyl, $C_{1-6}$ haloalkyl, $C_{1-6}$ alkoxy, substituted or unsubstituted $C_{2-6}$ alkenyl, substituted or unsubstituted $C_{2-6}$ alkynyl, substituted or unsubstituted $C_{3-6}$ cycloalkyl, aryl, heteroaryl, heterocyclic, alkylaryl, arylalkyl, hydroxyl, nitro, cyano, cyanoalkyl, azido, azidoalkyl, formyl, hydrazino, OR', SR', COOR', COR', OCOR', NHCOR', N(COR')COR', SCOR', OCOOR', and NHCOOR',
  wherein each R' is independently H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, wherein the groups can be substituted with one or more substituents selected from the group consisting of halogen, hydroxyl, amino, alkylamino, arylamino, alkoxy, aryloxy, nitro, cyano, sulfonic acid, sulfate, phosphonic acid, phosphate, or phosphonate,
- $R^1$ is and $R^{14}$ are, independently, H, $CH_3$, $CH_2F$, $CHF_2$, or $CF_3$, wherein, when $R^1$ is Me, the carbon to which it is attached may be wholly or partially R or S or any mixture thereof, or $R^1$ and $R^{14}$ can combine to form a $C_{3-7}$ cycloalkyl ring;
- $R^2$ is substituted or unsubstituted $C_{2-8}$ alkynyl;
- $R^4$ is $P(O)R^6R^7$, wherein, when chirality exists at the phosphorous center of $R^4$, it may be wholly or partially Rp or Sp or any mixture thereof,
- $R^5$ is O, $CH_2$, S, Se, CHF, $CF_2$, or $C=CH_2$,
- $R^3$ is H, substituted or unsubstituted $C_{1-8}$ alkyl, substituted or unsubstituted $C_{2-8}$ alkenyl, substituted or unsubstituted $C_{2-8}$ alkynyl, CN or $N_3$ when $R^5$ is O, and
- $R^3$ is selected from the group consisting of H, CN, substituted or unsubstituted $(C_{1-8})$alkyl, substituted or unsubstituted $(C_{2-8})$alkenyl, substituted or unsubstituted $(C_{2-8})$alkynyl, O—$(C_{1-8})$ alkyl and $N_3$ when $R^5$ is $CH_2$, CHF, $CF_2$, or $C=CH_2$,
- $R^8$ and $R^{8'}$ are independently selected from the group consisting of H, $C(O)(C_{1-8})$alkyl, $C(O)(C_{1-8})$ branched alkyl, $C(O)NH(C_{1-8})$alkyl, $C(O)NH(C_{1-8})$ branched alkyl, $C(O)$aryl $C(O)(C_{1-8})$ alkyl-aryl, $C(O)NH(C_{1-8})$alkyl-aryl $C(O)O(C_{1-8})$alkyl, $C(O)O(C_{1-8})$branched alkyl, and $C(O)O(C_{1-8})$alkyl-aryl, or $OR^8$ as it appears in Formulas A is an ester derived from an alpha amino acid,
- $R^6$ and $R^7$ are independently selected from the group consisting of:
  (a) $OR^{15}$ where $R^{15}$ is aryl, wherein aryl is optionally substituted with zero to three substituents independently selected from the group consisting of $(CH_2)_{0-6}CO_2R^{16}$ and $(CH_2)_{0-6}CON(R^{16})_2$;
  where $R^{16}$ is independently H, substituted or unsubstituted $C_{1-20}$ alkyl, the carbon chain derived from a fatty alcohol or $C_{1-20}$ alkyl substituted with a $C_{1-6}$ alkyl, $C_{1-6}$ alkoxy, di($C_{1-6}$ alkyl)-amino, fluoro, $C_{3-10}$ cycloalkyl, cycloalkyl-$C_{1-6}$ alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, alkoxy, di($C_{1-6}$ alkyl)-amino, fluoro, $C_{3-10}$ cycloalkyl, or cycloalkyl;

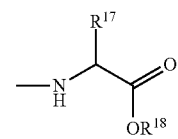

(b) the ester of a D- or L-amino acid where $R^{17}$ is restricted to those occurring in natural L-amino acids, and
- $R^{18}$ is H, $C_{1-20}$ alkyl, the carbon chain derived from a fatty alcohol or $C_{1-20}$ alkyl optionally substituted with a $C_{1-6}$ alkyl, alkoxy, di($C_{1-6}$alkyl)-amino, fluoro, $C_{3-10}$ cycloalkyl, cycloalkyl-$C_{1-6}$ alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, alkoxy, di($C_{1-6}$ alkyl)-amino, fluoro, $C_{3-10}$ cycloalkyl, or cycloalkyl;

Base is selected from the group consisting of:

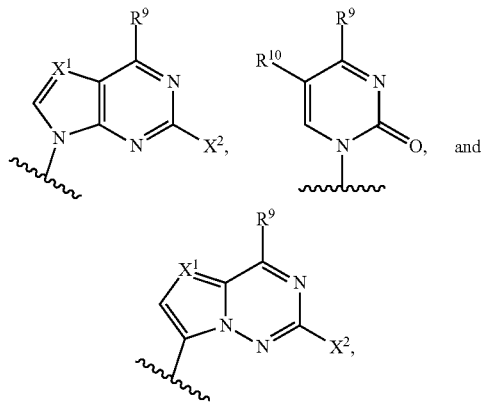

X¹ is CH, C—($C_{1-6}$)alkyl, C—($C_{2-6}$)alkenyl, C—($C_{2-6}$)alkynyl, C—($C_{3-7}$)cycloalkyl, C—($C_{1-6}$) haloalkyl, C—($C_{1-6}$)hydroxyalkyl, C—$OR^{22}$, C—N($R^{22}$)$_2$, C-halo, C—CN or N, $R^{22}$ is independently H, ($C_{1-10}$)alkyl, ($C_{1-10}$)haloalkyl or ($C_{3-7}$)cycloalkyl, $R^9$ is OH, $NH_2$, halo, O($C_{1-10}$)alkyl, O($C_{3-7}$)cycloalkyl, NH($C_{1-10}$)alkyl, N(($C_{1-10}$)alkyl)$_2$, NH($C_{3-7}$)cycloalkyl, NH(CO)($C_{1-20}$)alkyl, NH(CO)O($C_{1-20}$)alkyl, NHOH, NHO(CO)($C_{1-20}$)alkyl, or NHO(CO)NH($C_{1-20}$)alkyl, $R^{10}$ is H, F or $CH_3$ and $X^2$ is H, F, Cl, Br, I, ($C_{1-6}$)alkyl, ($C_{2-6}$)alkenyl, ($C_{2-6}$)alkynyl, C—($C_{3-7}$)cycloalkyl, C—($C_{1-6}$) haloalkyl, ($C_{1-6}$)haloalkyl, ($C_{3-7}$)cycloalkyl, ($C_{1-6}$)hydroxyalkyl, $OR^{22}$, N($R^{22}$)$_2$, NHC(O)$OR^{22}$, NHC(O)N($R^{22}$)$_2$, NHC(O)$R^{22}$, CN or $NH_2$;

or Base is

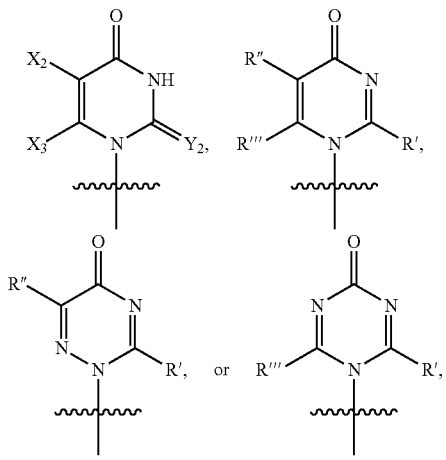

wherein:
each R', R", and R'" are independently selected from the group consisting of H, OH, substituted or unsubstituted $C_{1-6}$ alkyl, substituted or unsubstituted $C_{2-6}$ alkenyl, substituted or unsubstituted $C_{2-6}$ alkynyl, $C_{3-6}$ cycloalkyl, Br-vinyl, —O—$C_{1-6}$ alkyl, O—$C_{2-6}$ alkenyl, O—$C_{2-6}$ alkynyl, O-aryl, O-aralkyl, —O-acyl, O—$C_{3-6}$ cycloalkyl, $NH_2$, $NHC_{1-6}$ alkyl, N-di-$C_{1-6}$-alkyl, NH-acyl, N-aryl, N-aralkyl, $NHC_{3-6}$ cycloalkyl, F, Cl, Br, I, CN, COOH, $CONH_2$, $CO_2C_{1-6}$ alkyl, $CONHC_{1-6}$ alkyl, CON-di-$C_{1-6}$ alkyl, OH, $CF_3$, $CH_2OH$, $(CH_2)_mOH$, $(CH_2)_mNH_2$, $(CH_2)_mCO_2H$, $(CH_2)_mCN$, $(CH_2)_mNO_2$, and $(CH_2)_mCONH_2$;

m is 0 or 1;

$X^2$ is H, straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^{1B}$B, COO-alkyl, COO-aryl, CO—Oalkoxyalkyl, $CONH_2$, $CONHR^{1B}$, $CON(R^{1B})_2$, chloro, bromo, fluoro, iodo, CN, $N_3$, OH, $OR^{1B}$, $NH_2$, $NHR^{1B}$, $NR^{1B}{}_2$, each $X^3$ is independently a straight chained, branched or cyclic optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted $C_{2-6}$ alkenyl, $C_{2-6}$ haloalkenyl, Br-vinyl, optionally substituted alkynyl, $C_{2-6}$ haloalkynyl, $N_3$, CN, —C(O)OH, —C(O)$OR^{1B}$, —C(O)O($C_{1-6}$ alkyl), —C(O)$NH_2$, —C(O)$NHR^{1B}$, —C(O)NH($C_{1-6}$ alkyl), —C(O)N($R^{1B}$)$_2$, —C(O)N($C_{1-6}$ alkyl)$_2$, OH, $OR^{1B}$, —O(acyl), —O($C_{1-6}$ acyl), —O(alkyl), —O($C_{1-6}$ alkyl), —O($C_{2-6}$ alkenyl), —O($C_{2-6}$ alkynyl), —O(aralkyl), —O(cycloalkyl), chloro, bromo, fluoro, iodo, $NH_2$, —NH($C_{1-6}$ alkyl), —$NHR^{1B}$, —$NR^{1B}{}_2$, —NH(acyl), —N($C_{1-6}$ alkyl)$_2$, —NH(alkenyl), —NH(alkynyl), —NH(aralkyl), —NH(cycloalkyl), or —N(acyl)$_2$;

each $Y^2$ is independently O, S, Se, NH, or $NR^{1B}$;

each $Y^3$ is independently H, F, Cl, Br, or I; and each $R^{1B}$ is independently hydrogen, acyl, alkyl, $C_{1-6}$ alkyl, $C_{2-6}$ alkenyl, $C_{2-6}$ alkynyl, or $C_{3-6}$ cycloalkyl;

wherein, in each occurrence, $C_{1-6}$ alkyl, $C_{2-6}$ alkenyl, or $C_{2-6}$ alkynyl, are optionally substituted with from 1-3 substituents selected from the group consisting of halogen, hydroxyl, nitrile, amino, alkylamino, arylamino, alkoxy, thioalkoxy, aryloxy, nitro, cyano, sulfonic acid, sulfate, phosphonic acid, phosphate, or phosphonate, deuterated analogs thereof, and pharmaceutically-acceptable salts thereof.

2. The method of claim 1, wherein the compounds have the formula:

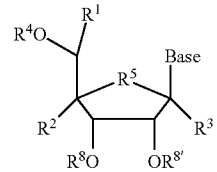

and deuterated analogs thereof.

3. The method of claim 2, wherein $R^2$ is ethynyl.

4. The method of claim 1, wherein $R^4$ is a phosphoramidate prodrug.

5. The method of claim 1, wherein $R^{15}$ is phenyl or pyridinyl.

6. The method of claim 1, wherein the compounds are deuterated at one or more positions on the base, $R^1$, $R^2$, $R^3$, $R^4$, R or Y.

7. The method of claim 1, wherein $R^8$ and $R^{8'}$ are H.

8. The method of claim 1, wherein Y is H.

9. The method of claim 1, wherein Y is Me.

10. The method of claim 1, wherein one or both of $R^8$ and $R^{8'}$ are H.
11. The method of claim 1, wherein the compound has one of the following formulas:
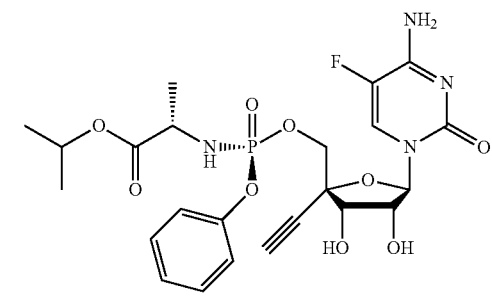
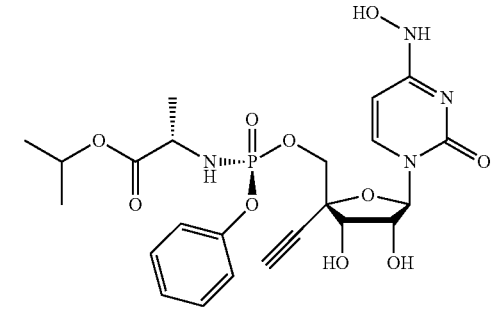
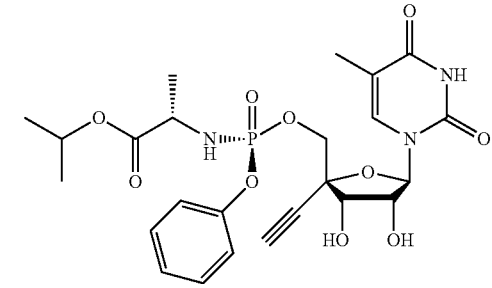
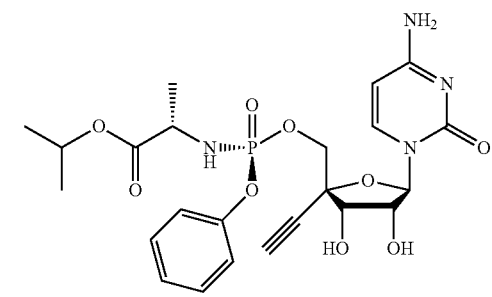
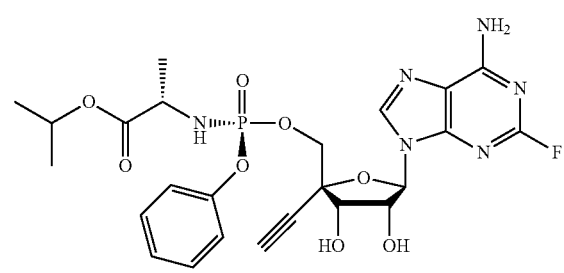
-continued
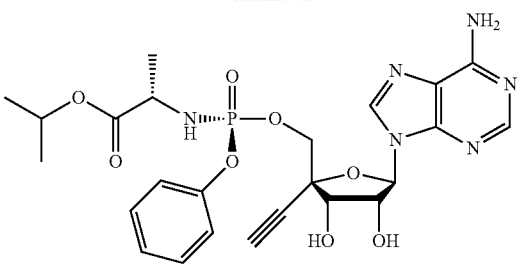
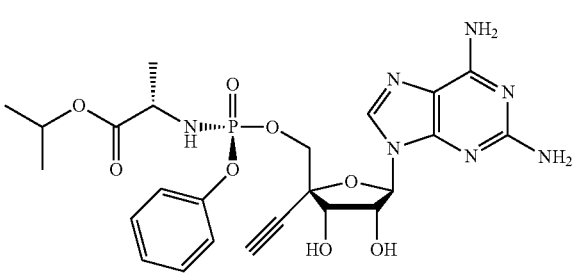
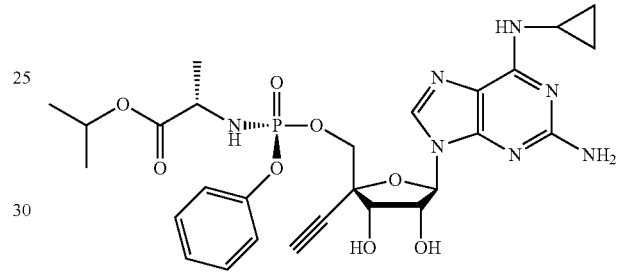
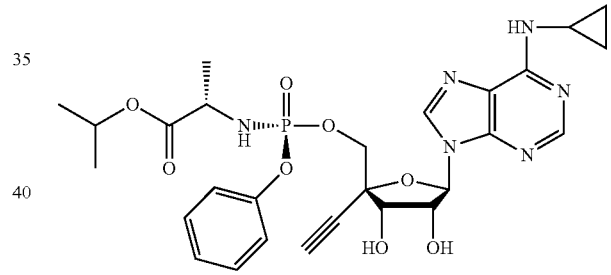
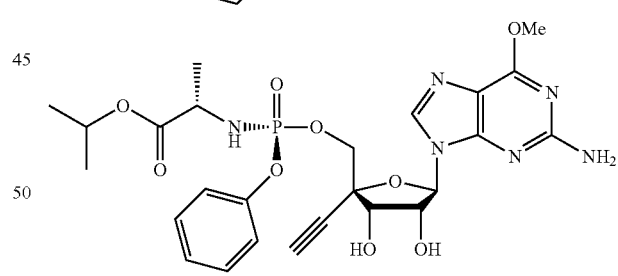
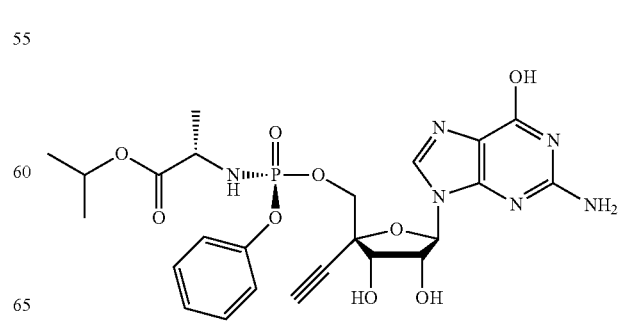

115
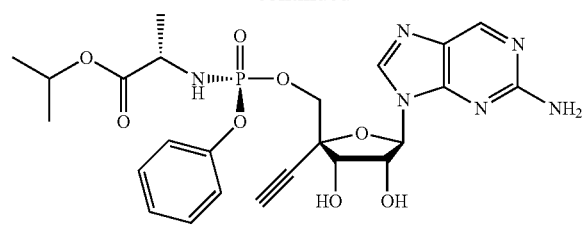
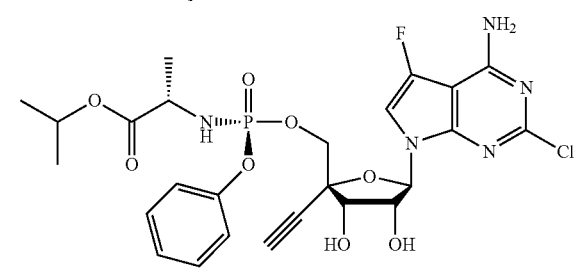
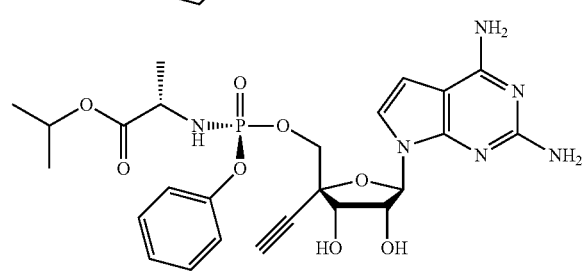
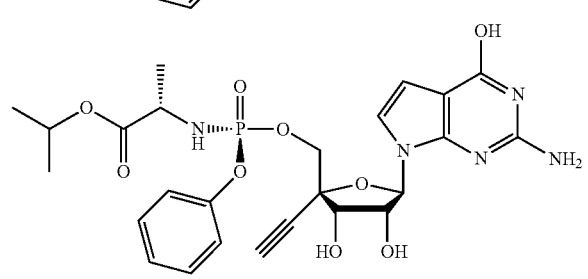
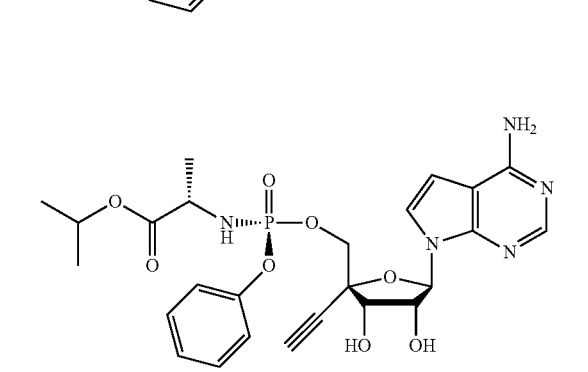
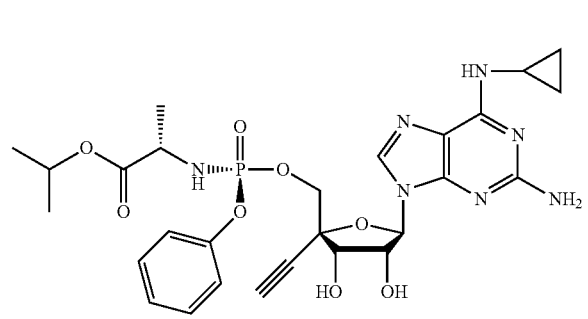
116
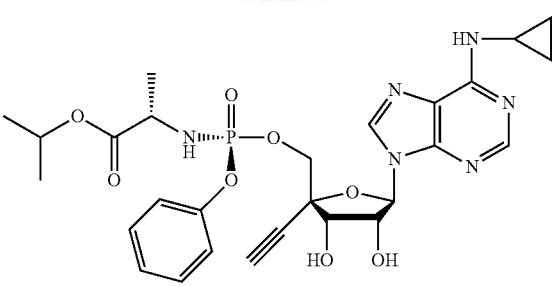
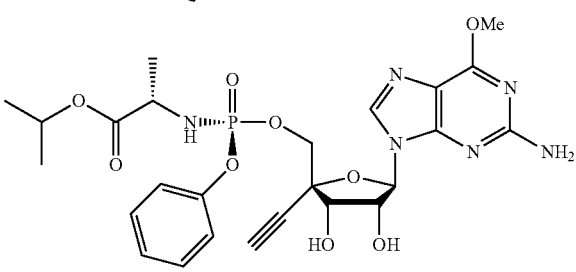
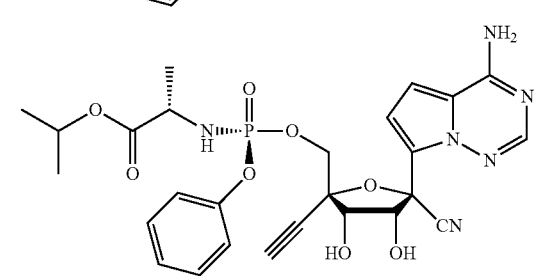
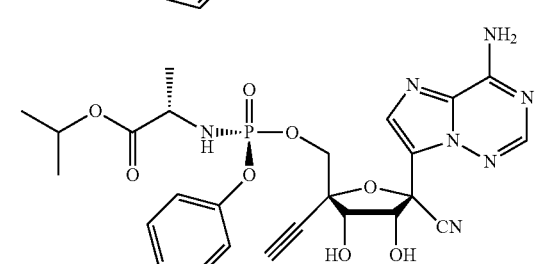
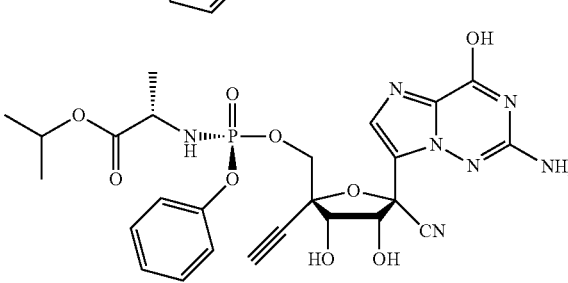
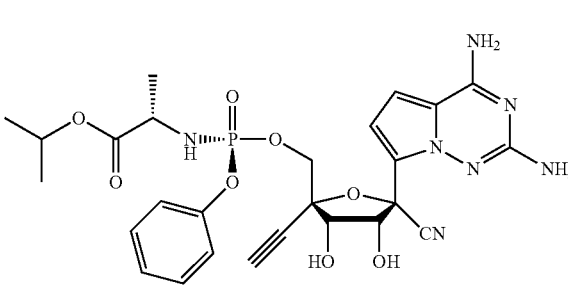

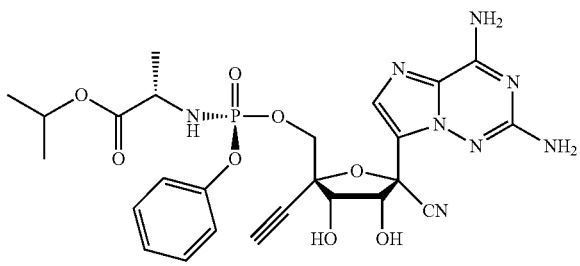

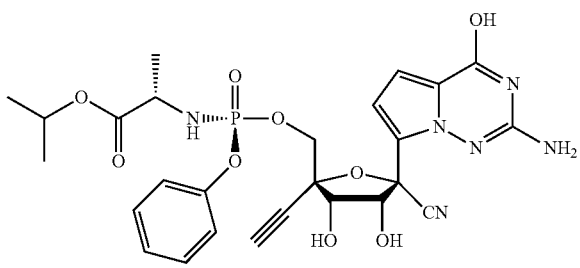

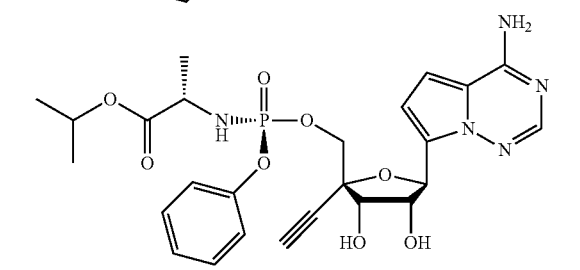

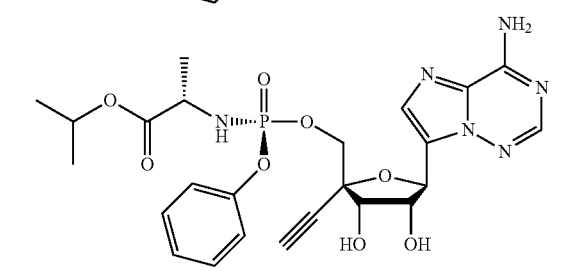

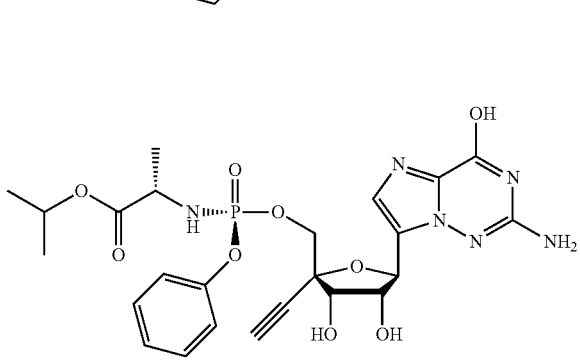

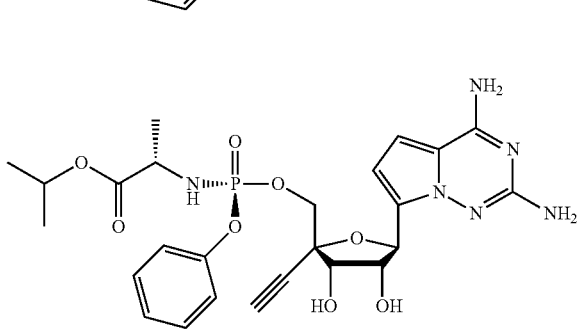

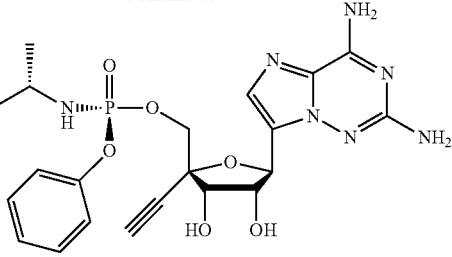

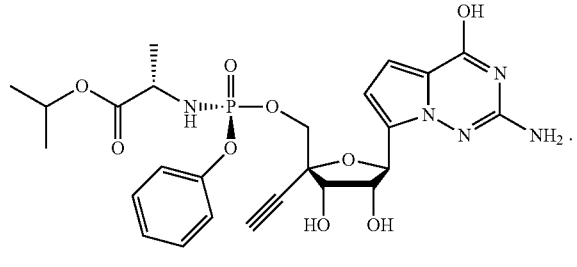

12. The method of claim 1, wherein the compound has the formula:

(A)

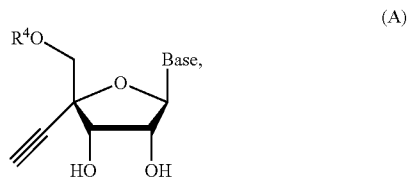

deuterated analogs thereof, or a pharmaceutically-acceptable salt thereof.

13. The method of claim 1, wherein the compounds can be present in the β-D or β-L configuration.

14. The method of claim 1, wherein the compound is administered in combination with a pharmaceutically-acceptable carrier or excipient.

15. The method of claim 14, wherein the compound is administered in the form of a transdermal composition or a nanoparticulate composition.

16. The method of claim 14, wherein the compound is administered in combination with a second antiviral agent.

17. The method of claim 16, wherein the second antiviral agent is selected from the group consisting of EFdA, Nucleoside Reverse Transcriptase Inhibitors (NRTIs), Non-nucleoside Reverse Transcriptase Inhibitors (NNRTIs), Protease Inhibitors, Fusion Inhibitors, Entry Inhibitors, CCR5 co-receptor antagonists, HIV integrase strand transfer inhibitors, JAK inhibitors, immunomodulators, dasatinib, MAPK inhibitors, mTOR inhibitors, β-catenin inhibitors, interferon inhibitors, interferon, HDAC inhibitors, PKC agonists, TLR4 agonists, reactivation agents, and combinations thereof.

18. The method of claim 17, wherein the JAK inhibitor is selected from the list consisting of tofacitinib, baricitinib, and ruxolitinib.

19. The method of claim 1, further comprising administering a NOX inhibitor.

20. The method of claim 19, wherein the NOX inhibitor is selected from the group consisting of AEBSF, Apocyanin, DPI, GK-136901 (4-methyl-5-pyridin-2-ylmethyl-2-o-tolyl-1,2-dihydro-5H-pyrazolo[4.3-c]pyridine-3,6-dione), ML171 (2-acetylphenothazine), Plumbagin, S17834 ([6,8- diallyl 5,7-dihydroxy 2-(2-allyl 3-hydroxy 4-methoxyphenyl)$_1$-H benzo(pyran-4-one]), VAS2870 (1,3-benzoxazol-2-yl-3-benzyl-3H-[1, 2, 3,]triazolo]4,5-d]pyrimidin-7-yl sulfide), VAS3947 (7-(2-Oxazolylthio)-3-(phenylmethyl)-3H-1, 2, 3-triazolo[4,5-d]pyrimidine), GKT-831 (Setanaxib), an amido thiadiazole derivative, a bi-aromatic or tri-aromatic compound, a methoxyflavone derivative, a peptide, a piperazine derivative, a pyrazole derivative, a pyrazoline dione derivative, a pyrazolo pyridine derivative, a quinazoline or quinoline derivative, a tetrahydroindole derivative, a tetrahydroisoquinoline derivative, Scopoletin, or a 2,5-disubstituted benzoxazole or benzothiazole derivative.

21. The method of claim 20, wherein the peptide is NOX2ds-tat (NOX2 docketing sequence-tat) or PR-39 (Proline-Arginine-39).

22. The method of claim 20, wherein the NOX inhibitor is selected from the group consisting of Ebselen, Neopterin, APBA, Diapocynin, deuterated analogs thereof, and pharmaceutically-acceptable salts thereof.

\* \* \* \* \*

```
                        SEQUENCE LISTING

<160> NUMBER OF SEQ ID NOS: 14

<210> SEQ ID NO 1
<211> LENGTH: 17
<212> TYPE: DNA
<213> ORGANISM: Human

<400> SEQUENCE: 1
tgcccgccat catccta                                                  17

<210> SEQ ID NO 2
<211> LENGTH: 21
<212> TYPE: DNA
<213> ORGANISM: Human

<400> SEQUENCE: 2
tcctcatcgc cctcccatcc c                                             21

<210> SEQ ID NO 3
<211> LENGTH: 23
<212> TYPE: DNA
<213> ORGANISM: Human

<400> SEQUENCE: 3
cgtctgttat gtaaaggatg cgt                                           23

<210> SEQ ID NO 4
<211> LENGTH: 17
<212> TYPE: DNA
<213> ORGANISM: Human

<400> SEQUENCE: 4
gcgcggctac agcttca                                                  17

<210> SEQ ID NO 5
<211> LENGTH: 20
<212> TYPE: DNA
<213> ORGANISM: Human

<400> SEQUENCE: 5
caccacggcc gagcgggata                                               20

<210> SEQ ID NO 6
<211> LENGTH: 22
<212> TYPE: DNA
<213> ORGANISM: Human
```

-continued

```
<400> SEQUENCE: 6
tctccttaat gtcacgcacg at                                              22

<210> SEQ ID NO 7
<211> LENGTH: 12
<212> TYPE: RNA
<213> ORGANISM: Human

<400> SEQUENCE: 7
uuuugccgcg cc                                                         12

<210> SEQ ID NO 8
<211> LENGTH: 18
<212> TYPE: DNA
<213> ORGANISM: Human
<220> FEATURE:
<221> NAME/KEY: misc_feature
<222> LOCATION: (10)..(10)
<223> OTHER INFORMATION: n is a, c, g, or t

<400> SEQUENCE: 8
gggaatgcan ggcgcggc                                                   18

<210> SEQ ID NO 9
<211> LENGTH: 24
<212> TYPE: DNA
<213> ORGANISM: Human

<400> SEQUENCE: 9
tcaggtccct gttcgggcgc cact                                            24

<210> SEQ ID NO 10
<211> LENGTH: 48
<212> TYPE: DNA
<213> ORGANISM: Human

<400> SEQUENCE: 10
cagtgtggaa aatctctagc agtggcgccc gaacagggac ctgaaagc                  48

<210> SEQ ID NO 11
<211> LENGTH: 24
<212> TYPE: DNA
<213> ORGANISM: Human

<400> SEQUENCE: 11
tcaggtccct gttcgggcgc cact                                            24

<210> SEQ ID NO 12
<211> LENGTH: 48
<212> TYPE: DNA
<213> ORGANISM: Human

<400> SEQUENCE: 12
cagtgtggaa aatctctagc agtggcgccc gaacagggac ctgaaagc                  48

<210> SEQ ID NO 13
<211> LENGTH: 24
<212> TYPE: DNA
<213> ORGANISM: Human

<400> SEQUENCE: 13
tcaggtccct gttcgggcgc cact                                            24
```

```
<210> SEQ ID NO 14
<211> LENGTH: 36
<212> TYPE: DNA
<213> ORGANISM: Human

<400> SEQUENCE: 14
tctctagaag tggcgcccga acagggacct gaaagc                           36
```